(12) United States Patent
Emery et al.

(10) Patent No.: US 8,372,009 B2
(45) Date of Patent: Feb. 12, 2013

(54) SYSTEM AND METHOD FOR TREATING A THERAPEUTIC SITE

(75) Inventors: Charles Emery, Issaquah, WA (US);
Larry Augustine, Bothell, WA (US);
Robyn Lahman, Redmond, WA (US);
David M Perozek, Mercer Island, WA (US); Jimin Zhang, Bellevue, WA (US)

(73) Assignee: Kona Medical, Inc., Palo Alto, CA (US)

( * ) Notice: Subject to any disclaimer, the term of this patent is extended or adjusted under 35 U.S.C. 154(b) by 0 days.

(21) Appl. No.: 13/245,703

(22) Filed: Sep. 26, 2011

(65) Prior Publication Data

US 2012/0059259 A1 Mar. 8, 2012

Related U.S. Application Data

(63) Continuation of application No. 13/118,245, filed on May 27, 2011, which is a continuation of application No. 11/583,569, filed on Oct. 19, 2006, now Pat. No. 8,167,805.

(60) Provisional application No. 60/728,783, filed on Oct. 20, 2005, provisional application No. 60/808,665, filed on May 26, 2006.

(51) Int. Cl.
*A61B 8/00* (2006.01)

(52) U.S. Cl. ............... 600/439; 600/437; 601/2; 601/3; 601/4

(58) Field of Classification Search .................. 600/437, 600/439; 601/2–4
See application file for complete search history.

(56) References Cited

U.S. PATENT DOCUMENTS

| | | |
|---|---|---|
| 385,256 A | 6/1888 | Eggers |
| 3,274,437 A | 9/1966 | Mastrup |
| 3,499,437 A | 3/1970 | Balamuth |
| 3,552,382 A | 1/1971 | Mount |
| 3,847,016 A | 11/1974 | Ziedonis |
| 3,927,662 A | 12/1975 | Ziedonis |
| 4,059,098 A | 11/1977 | Murdock |
| 4,167,180 A | 9/1979 | Kossoff |
| 4,197,856 A | 4/1980 | Northrop |
| 4,206,763 A | 6/1980 | Pendersen |

(Continued)

FOREIGN PATENT DOCUMENTS

| | | |
|---|---|---|
| DE | 4230415 | 3/1994 |
| EP | 0420758 | 4/1991 |

(Continued)

OTHER PUBLICATIONS

Accord et al., "The Issue of Transmurality in Surgical Ablation for Atrial Fibrillation." Cardiothoracic Surgery Network: 3pp, Feb. 8, 2007.

(Continued)

*Primary Examiner* — Peter Luong
(74) *Attorney, Agent, or Firm* — Knobbe Martens Olson & Bear, LLP

(57) ABSTRACT

A targeting catheter is used to locate an arteriotomy, such as is formed during a femoral artery catheterization procedure. The targeting catheter includes one or more targeting aids, such as an inflatable balloon or sensor (e.g., Doppler or temperature sensor), to locate the arteriotomy. The targeting aid may be positioned at the arteriotomy. An ultrasonic beacon on the catheter may then be located relative to a therapeutic ultrasonic applicator (e.g., by using acoustic time-of-flight) so that the focus of ultrasonic energy from the applicator can be aligned with the arteriotomy.

13 Claims, 48 Drawing Sheets

U.S. PATENT DOCUMENTS

| | | | |
|---|---|---|---|
| 4,237,901 A | 12/1980 | Taenzer | |
| 4,273,127 A | 6/1981 | Auth et al. | |
| 4,315,514 A | 2/1982 | Drewes et al. | |
| 4,469,099 A | 9/1984 | McEwen | |
| 4,479,494 A | 10/1984 | McEwen | |
| 4,484,569 A | 11/1984 | Driller et al. | |
| 4,545,386 A | 10/1985 | Hetz et al. | |
| 4,594,895 A | 6/1986 | Fujii | |
| 4,601,296 A | 7/1986 | Yerushalmi | |
| 4,605,010 A | 8/1986 | McEwen | |
| 4,688,578 A | 8/1987 | Takano et al. | |
| 4,708,836 A | 11/1987 | Gain et al. | |
| 4,748,985 A | 6/1988 | Nagasaki | |
| 4,757,820 A | 7/1988 | Itoh | |
| 4,770,175 A | 9/1988 | McEwen | |
| 4,773,865 A | 9/1988 | Baldwin | |
| 4,784,148 A | 11/1988 | Dow et al. | |
| 4,841,979 A | 6/1989 | Dow et al. | |
| 4,850,363 A | 7/1989 | Yanagawa | |
| 4,858,613 A | 8/1989 | Fry et al. | |
| 4,905,672 A | 3/1990 | Schwarze et al. | |
| 4,913,155 A | 4/1990 | Dow et al. | |
| 4,929,246 A | 5/1990 | Sinofsky | |
| 4,931,047 A | 6/1990 | Broadwin et al. | |
| 4,938,216 A | 7/1990 | Lele | |
| 4,938,217 A | 7/1990 | Lele | |
| 4,957,099 A | 9/1990 | Hassler | |
| 5,005,579 A | 4/1991 | Wurster et al. | |
| RE33,590 E | 5/1991 | Dory | |
| 5,026,387 A | 6/1991 | Thomas | |
| 5,036,855 A | 8/1991 | Fry et al. | |
| 5,039,774 A | 8/1991 | Shikinami et al. | |
| 5,042,486 A | 8/1991 | Pfeiler et al. | |
| 5,065,742 A | 11/1991 | Belikan et al. | |
| 5,080,101 A | 1/1992 | Dory | |
| 5,080,102 A | 1/1992 | Dory | |
| 5,150,712 A | 9/1992 | Dory | |
| 5,170,790 A | 12/1992 | Lacoste et al. | |
| 5,178,135 A | 1/1993 | Uchiyama et al. | |
| 5,178,148 A | 1/1993 | Lacoste et al. | |
| 5,181,522 A | 1/1993 | McEwen | |
| 5,194,291 A | 3/1993 | D'Aoust et al. | |
| 5,211,160 A | 5/1993 | Talish et al. | |
| 5,215,680 A | 6/1993 | D'Arrigo | |
| 5,219,401 A | 6/1993 | Cathignol et al. | |
| 5,230,334 A | 7/1993 | Klopotek | |
| 5,230,921 A | 7/1993 | Waltonen et al. | |
| 5,233,994 A | 8/1993 | Shmulewitz | |
| 5,243,988 A | 9/1993 | Sieben et al. | |
| 5,254,087 A | 10/1993 | McEwen | |
| 5,263,957 A | 11/1993 | Davison | |
| 5,290,278 A | 3/1994 | Anderson | |
| 5,307,816 A * | 5/1994 | Hashimoto et al. | 600/439 |
| 5,311,869 A | 5/1994 | Okazaki | |
| 5,312,431 A | 5/1994 | McEwen | |
| 5,352,195 A | 10/1994 | McEwen | |
| 5,364,389 A | 11/1994 | Anderson | |
| 5,383,896 A | 1/1995 | Gershony et al. | |
| 5,391,140 A | 2/1995 | Schaetzle et al. | |
| 5,391,197 A | 2/1995 | Burdette et al. | |
| 5,394,877 A | 3/1995 | Orr et al. | |
| 5,415,657 A | 5/1995 | Taymor-Luria | |
| 5,439,477 A | 8/1995 | McEwen | |
| 5,453,576 A | 9/1995 | Krivitski | |
| 5,454,373 A | 10/1995 | Koger et al. | |
| 5,454,831 A | 10/1995 | McEwen | |
| 5,471,988 A | 12/1995 | Fujio et al. | |
| 5,474,071 A | 12/1995 | Chapelon et al. | |
| 5,492,126 A | 2/1996 | Hennige et al. | |
| 5,503,152 A | 4/1996 | Oakley et al. | |
| 5,507,744 A | 4/1996 | Tay et al. | |
| 5,507,790 A | 4/1996 | Weiss | |
| 5,515,853 A | 5/1996 | Smith et al. | |
| 5,520,188 A | 5/1996 | Hennige et al. | |
| 5,522,878 A | 6/1996 | Montecalvo et al. | |
| 5,524,620 A | 6/1996 | Rosenschein | |
| 5,526,815 A | 6/1996 | Granz et al. | |
| 5,534,232 A | 7/1996 | Denes et al. | |
| 5,536,489 A | 7/1996 | Lohrmann et al. |
| 5,553,618 A | 9/1996 | Suzuki et al. |
| 5,556,415 A | 9/1996 | McEwen et al. |
| 5,558,092 A | 9/1996 | Unger et al. |
| 5,573,497 A | 11/1996 | Chapelon |
| 5,578,055 A | 11/1996 | McEwen |
| 5,584,853 A | 12/1996 | McEwen |
| 5,601,526 A | 2/1997 | Chapelon et al. |
| 5,607,447 A | 3/1997 | McEwen et al. |
| 5,609,485 A | 3/1997 | Bergman et al. |
| 5,626,601 A | 5/1997 | Gershony et al. |
| 5,630,837 A | 5/1997 | Crowley |
| 5,638,823 A | 6/1997 | Akay et al. |
| 5,643,179 A | 7/1997 | Fujimoto |
| 5,649,954 A | 7/1997 | McEwen |
| 5,655,538 A | 8/1997 | Lorraine et al. |
| 5,657,760 A | 8/1997 | Ying et al. |
| 5,665,073 A | 9/1997 | Bulow et al. |
| 5,666,954 A | 9/1997 | Chapelon et al. |
| 5,681,339 A | 10/1997 | McEwen et al. |
| 5,685,307 A | 11/1997 | Holland et al. |
| 5,695,493 A | 12/1997 | Nakajima et al. |
| 5,697,897 A | 12/1997 | Buchholtz et al. |
| D389,574 S | 1/1998 | Emerson et al. |
| 5,711,058 A | 1/1998 | Frey et al. |
| 5,716,374 A | 2/1998 | Francese et al. |
| 5,720,286 A | 2/1998 | Chapelon et al. |
| 5,720,287 A | 2/1998 | Chapelon et al. |
| 5,726,066 A | 3/1998 | Choi |
| 5,735,796 A | 4/1998 | Granz et al. |
| 5,738,635 A | 4/1998 | Chapelon et al. |
| 5,741,295 A | 4/1998 | McEwen |
| 5,755,228 A | 5/1998 | Wilson et al. |
| 5,762,066 A | 6/1998 | Law et al. |
| 5,769,790 A | 6/1998 | Watkins et al. |
| 5,788,636 A | 8/1998 | Curley |
| 5,807,285 A | 9/1998 | Vaitekunas |
| 5,810,007 A | 9/1998 | Holupka et al. |
| 5,810,810 A | 9/1998 | Tay et al. |
| 5,817,021 A | 10/1998 | Reichenberger |
| 5,823,962 A | 10/1998 | Schaetzle et al. |
| 5,824,015 A | 10/1998 | Sawyer |
| 5,824,277 A | 10/1998 | Campos |
| 5,827,204 A | 10/1998 | Grandia et al. |
| 5,827,268 A | 10/1998 | Laufer |
| 5,833,647 A | 11/1998 | Edwards |
| 5,840,028 A | 11/1998 | Chubachi et al. |
| 5,846,517 A | 12/1998 | Unger |
| 5,852,860 A | 12/1998 | Lorraine et al. |
| 5,853,752 A | 12/1998 | Unger et al. |
| 5,855,589 A | 1/1999 | McEwen et al. |
| 5,873,828 A | 2/1999 | Fujio et al. |
| 5,879,314 A | 3/1999 | Peterson et al. |
| 5,882,302 A | 3/1999 | Driscoll, Jr. et al. |
| 5,895,356 A | 4/1999 | Andrus |
| 5,904,659 A | 5/1999 | Duarte |
| 5,906,580 A | 5/1999 | Kline-Schoder et al. |
| 5,911,735 A | 6/1999 | McEwen et al. |
| 5,919,139 A | 7/1999 | Lin |
| 5,921,994 A | 7/1999 | Andreas et al. |
| 5,922,945 A | 7/1999 | Allmaras et al. |
| 5,931,786 A | 8/1999 | Whitmore, III et al. |
| 5,931,853 A | 8/1999 | McEwen |
| 5,935,144 A | 8/1999 | Estabrook |
| 5,935,146 A | 8/1999 | McEwen |
| 5,935,339 A | 8/1999 | Henderson et al. |
| 5,951,476 A | 9/1999 | Beach |
| 5,957,849 A | 9/1999 | Munro |
| 5,964,782 A | 10/1999 | Lafontaine et al. |
| 5,976,092 A | 11/1999 | Chinn |
| 5,979,453 A | 11/1999 | Savage et al. |
| 5,993,389 A | 11/1999 | Driscoll, Jr. et al. |
| 5,997,481 A | 12/1999 | Adams et al. |
| 6,007,499 A | 12/1999 | Martin et al. |
| 6,013,031 A | 1/2000 | Mendlein et al. |
| 6,014,473 A | 1/2000 | Hossack et al. |
| 6,033,506 A | 3/2000 | Klett |
| 6,036,650 A | 3/2000 | Wu et al. |
| 6,037,032 A | 3/2000 | Klett et al. |

| Patent | Type | Date | Inventors |
|---|---|---|---|
| 6,039,694 | A | 3/2000 | Larson et al. |
| 6,042,556 | A | 3/2000 | Beach et al. |
| 6,050,943 | A | 4/2000 | Slayton et al. |
| 6,067,371 | A | 5/2000 | Gouge et al. |
| 6,068,596 | A | 5/2000 | Weth et al. |
| 6,071,239 | A | 6/2000 | Cribbs et al. |
| 6,071,277 | A | 6/2000 | Farley et al. |
| 6,078,831 | A | 6/2000 | Belef et al. |
| 6,083,159 | A | 7/2000 | Driscoll, Jr. et al. |
| 6,087,761 | A | 7/2000 | Lorraine et al. |
| 6,102,860 | A | 8/2000 | Mooney |
| 6,106,463 | A | 8/2000 | Wilk |
| 6,120,453 | A | 9/2000 | Sharp |
| 6,128,522 | A | 10/2000 | Acker et al. |
| 6,179,831 | B1 | 1/2001 | Bliweis |
| 6,182,341 | B1 | 2/2001 | Talbot et al. |
| 6,200,539 | B1 | 3/2001 | Sherman et al. |
| 6,206,843 | B1 | 3/2001 | Iger et al. |
| 6,213,939 | B1 | 4/2001 | McEwen |
| 6,217,530 | B1 | 4/2001 | Martin et al. |
| 6,221,015 | B1 | 4/2001 | Yock |
| 6,231,507 | B1 | 5/2001 | Zikorus et al. |
| 6,233,477 | B1 | 5/2001 | Chia et al. |
| 6,246,156 | B1 | 6/2001 | Takeuchi et al. |
| 6,254,601 | B1 | 7/2001 | Burbank et al. |
| 6,259,945 | B1 | 7/2001 | Epstein et al. |
| 6,261,233 | B1 | 7/2001 | Kantorovich |
| 6,263,551 | B1 | 7/2001 | Lorraine et al. |
| 6,267,734 | B1 | 7/2001 | Ishibashi et al. |
| 6,270,458 | B1 | 8/2001 | Barnea |
| 6,277,077 | B1 | 8/2001 | Brisken et al. |
| 6,311,692 | B1 | 11/2001 | Vaska et al. |
| 6,315,441 | B2 | 11/2001 | King |
| 6,332,089 | B1 | 12/2001 | Acker et al. |
| 6,361,496 | B1 | 3/2002 | Zikorus et al. |
| 6,361,548 | B1 | 3/2002 | McEwen |
| 6,399,149 | B1 | 6/2002 | Klett et al. |
| 6,406,759 | B1 | 6/2002 | Roth |
| 6,409,720 | B1 | 6/2002 | Hissong et al. |
| 6,419,669 | B1 | 7/2002 | Frazier et al. |
| 6,425,867 | B1 | 7/2002 | Vaezy et al. |
| 6,425,876 | B1 | 7/2002 | Frangi et al. |
| 6,432,067 | B1 | 8/2002 | Martin et al. |
| 6,443,894 | B1 | 9/2002 | Sumanaweera et al. |
| 6,453,526 | B2 | 9/2002 | Lorraine et al. |
| 6,488,639 | B1 | 12/2002 | Ribault et al. |
| 6,491,672 | B2 | 12/2002 | Slepian et al. |
| 6,494,848 | B1 | 12/2002 | Sommercorn et al. |
| 6,500,133 | B2 | 12/2002 | Martin et al. |
| 6,520,915 | B1 | 2/2003 | Lin et al. |
| 6,522,926 | B1 | 2/2003 | Kieval et al. |
| 6,548,047 | B1 | 4/2003 | Unger |
| 6,551,576 | B1 | 4/2003 | Unger et al. |
| 6,559,644 | B2 | 5/2003 | Froundlich et al. |
| 6,562,037 | B2 | 5/2003 | Paton et al. |
| 6,565,557 | B1 | 5/2003 | Sporri et al. |
| 6,576,168 | B2 | 6/2003 | Hardcastle et al. |
| 6,584,360 | B2 | 6/2003 | Francischelli et al. |
| 6,595,934 | B1 | 7/2003 | Hissong et al. |
| 6,599,256 | B1 | 7/2003 | Acker et al. |
| 6,599,288 | B2 | 7/2003 | Maguire et al. |
| 6,602,251 | B2 | 8/2003 | Burbank et al. |
| 6,612,988 | B2 | 9/2003 | Maor et al. |
| 6,616,624 | B1 | 9/2003 | Kieval |
| 6,626,855 | B1 | 9/2003 | Weng et al. |
| 6,633,658 | B1 | 10/2003 | Dabney et al. |
| 6,652,461 | B1 | 11/2003 | Levkovitz |
| 6,656,131 | B2 | 12/2003 | Alster et al. |
| 6,656,136 | B1 | 12/2003 | Weng et al. |
| 6,676,601 | B1 | 1/2004 | Lacoste et al. |
| 6,682,483 | B1 | 1/2004 | Abend et al. |
| 6,685,639 | B1 | 2/2004 | Wang et al. |
| 6,706,892 | B1 | 3/2004 | Ezrin et al. |
| 6,709,392 | B1 | 3/2004 | Salgo et al. |
| 6,709,407 | B2 | 3/2004 | Fatemi |
| 6,716,184 | B2 | 4/2004 | Vaezy et al. |
| 6,719,694 | B2 | 4/2004 | Weng et al. |
| 6,719,699 | B2 | 4/2004 | Smith |
| 6,726,627 | B1 | 4/2004 | Lizzi et al. |
| 6,735,461 | B2 | 5/2004 | Vitek et al. |
| 6,755,789 | B2 | 6/2004 | Stringer et al. |
| 6,764,488 | B1 | 7/2004 | Burbank et al. |
| 6,846,291 | B2 | 1/2005 | Smith et al. |
| 6,868,739 | B1 | 3/2005 | Krivitski et al. |
| 6,875,176 | B2 | 4/2005 | Mourad et al. |
| 6,875,420 | B1 | 4/2005 | Quay |
| 6,905,498 | B2 | 6/2005 | Hooven |
| 6,932,771 | B2 | 8/2005 | Whitmore et al. |
| 6,955,648 | B2 | 10/2005 | Mozayeni et al. |
| 6,978,174 | B2 | 12/2005 | Gelfand et al. |
| 7,022,077 | B2 | 4/2006 | Mourad et al. |
| 7,052,463 | B2 | 5/2006 | Peszynski et al. |
| 7,063,666 | B2 | 6/2006 | Lee et al. |
| 7,128,711 | B2 | 10/2006 | Medan et al. |
| 7,149,564 | B2 | 12/2006 | Vining et al. |
| 7,162,303 | B2 | 1/2007 | Levin et al. |
| 7,211,060 | B1 | 5/2007 | Talish et al. |
| 7,260,250 | B2 | 8/2007 | Summers et al. |
| 7,285,093 | B2 | 10/2007 | Anisimov et al. |
| 7,445,599 | B2 | 11/2008 | Kelly et al. |
| 7,470,241 | B2 | 12/2008 | Weng et al. |
| 7,499,748 | B2 | 3/2009 | Moffitt et al. |
| 7,510,536 | B2 | 3/2009 | Foley et al. |
| 7,530,958 | B2 | 5/2009 | Slayton et al. |
| 7,534,209 | B2 | 5/2009 | Abend |
| 7,553,284 | B2 | 6/2009 | Vaitekunas |
| 7,617,005 | B2 | 11/2009 | Demarais et al. |
| 7,620,451 | B2 | 11/2009 | Demarais et al. |
| 7,628,764 | B2 | 12/2009 | Duarte et al. |
| 7,684,865 | B2 | 3/2010 | Aldrich et al. |
| 7,697,972 | B2 | 4/2010 | Verard et al. |
| 2001/0014775 | A1 | 8/2001 | Koger et al. |
| 2001/0014805 | A1 | 8/2001 | Burbank et al. |
| 2001/0032382 | A1 | 10/2001 | Lorraine et al. |
| 2001/0041910 | A1 | 11/2001 | McEwen |
| 2001/0044636 | A1 | 11/2001 | Pedros et al. |
| 2002/0032394 | A1 | 3/2002 | Brisken et al. |
| 2002/0055736 | A1 | 5/2002 | Horn et al. |
| 2002/0095164 | A1 | 7/2002 | Andreas et al. |
| 2002/0193831 | A1 | 12/2002 | Smith, III |
| 2003/0009194 | A1 | 1/2003 | Saker et al. |
| 2003/0018255 | A1 | 1/2003 | Martin et al. |
| 2003/0036771 | A1 | 2/2003 | McEwen |
| 2003/0050665 | A1 | 3/2003 | Ginn |
| 2003/0069569 | A1 | 4/2003 | Burdette et al. |
| 2003/0114756 | A1 | 6/2003 | Li |
| 2003/0120204 | A1 | 6/2003 | Unger et al. |
| 2003/0153849 | A1 | 8/2003 | Huckle et al. |
| 2003/0195420 | A1 | 10/2003 | Mendlein et al. |
| 2003/0208101 | A1 | 11/2003 | Cecchi |
| 2003/0216792 | A1 | 11/2003 | Levin et al. |
| 2004/0002654 | A1 | 1/2004 | Davidson et al. |
| 2004/0030227 | A1 | 2/2004 | Littrup et al. |
| 2004/0030268 | A1 | 2/2004 | Weng et al. |
| 2004/0054287 | A1 | 3/2004 | Stephens |
| 2004/0054289 | A1 | 3/2004 | Eberle et al. |
| 2004/0078034 | A1 | 4/2004 | Acker et al. |
| 2004/0078219 | A1 | 4/2004 | Kaylor |
| 2004/0082978 | A1 | 4/2004 | Harrison et al. |
| 2004/0097840 | A1 | 5/2004 | Holmer |
| 2004/0106880 | A1 | 6/2004 | Lee et al. |
| 2004/0113524 | A1 | 6/2004 | Baumgartner et al. |
| 2004/0122493 | A1 | 6/2004 | Ishibashi et al. |
| 2004/0127798 | A1 | 7/2004 | Dala-Krishna et al. |
| 2004/0153126 | A1 | 8/2004 | Okai |
| 2004/0158154 | A1 | 8/2004 | Hanafy et al. |
| 2004/0234453 | A1 | 11/2004 | Smith |
| 2004/0254620 | A1 | 12/2004 | Lacoste et al. |
| 2004/0267252 | A1 | 12/2004 | Washington et al. |
| 2005/0043625 | A1 | 2/2005 | Oliver et al. |
| 2005/0046311 | A1 | 3/2005 | Baumgartner et al. |
| 2005/0054955 | A1 | 3/2005 | Lidgren |
| 2005/0065436 | A1 | 3/2005 | Ho et al. |
| 2005/0070790 | A1 | 3/2005 | Niwa et al. |
| 2005/0085793 | A1 | 4/2005 | Glossop |
| 2005/0090104 | A1 | 4/2005 | Yang et al. |
| 2005/0096542 | A1 | 5/2005 | Lee et al. |
| 2005/0154299 | A1 | 7/2005 | Hoctor et al. |

| | | |
|---|---|---|
| 2005/0165298 A1 | 7/2005 | Larson et al. |
| 2005/0182297 A1 | 8/2005 | Gravenstein et al. |
| 2005/0182319 A1 | 8/2005 | Glossop |
| 2005/0240102 A1 | 10/2005 | Rachlin et al. |
| 2005/0240103 A1 | 10/2005 | Byrd et al. |
| 2005/0240126 A1 | 10/2005 | Foley et al. |
| 2005/0240170 A1 | 10/2005 | Jimin et al. |
| 2006/0025756 A1 | 2/2006 | Francischelli et al. |
| 2006/0058678 A1 | 3/2006 | Vitek et al. |
| 2006/0122514 A1 | 6/2006 | Byrd et al. |
| 2006/0184069 A1 | 8/2006 | Vaitekunas |
| 2006/0235300 A1 | 10/2006 | Lee et al. |
| 2007/0004984 A1 | 1/2007 | Crum et al. |
| 2007/0055155 A1 | 3/2007 | Owen et al. |
| 2007/0106339 A1 | 5/2007 | Errico et al. |
| 2007/0129720 A1 | 6/2007 | Demarais et al. |
| 2007/0142879 A1 | 6/2007 | Greenberg et al. |
| 2007/0149880 A1 | 6/2007 | Willis |
| 2007/0167806 A1 | 7/2007 | Wood et al. |
| 2007/0179379 A1 | 8/2007 | Lee et al. |
| 2007/0213616 A1 | 9/2007 | Anderson et al. |
| 2007/0233185 A1 | 10/2007 | Anderson et al. |
| 2007/0239000 A1 | 10/2007 | Emery et al. |
| 2007/0265687 A1 | 11/2007 | Deem et al. |
| 2008/0033292 A1 | 2/2008 | Shafran |
| 2008/0039746 A1 | 2/2008 | Hissong et al. |
| 2008/0045864 A1 | 2/2008 | Candy et al. |
| 2008/0045865 A1 | 2/2008 | Kislev |
| 2008/0047325 A1 | 2/2008 | Bartlett |
| 2008/0200815 A1 | 8/2008 | Van Der Steen et al. |
| 2008/0234569 A1 | 9/2008 | Tidhar et al. |
| 2008/0255498 A1 | 10/2008 | Houle |
| 2008/0255642 A1 | 10/2008 | Demarais et al. |
| 2008/0312561 A1 | 12/2008 | Chauhan |
| 2008/0317204 A1 | 12/2008 | Sumanaweera et al. |
| 2008/0319375 A1 | 12/2008 | Hardy |
| 2009/0012098 A1 | 1/2009 | Jordan et al. |
| 2009/0036948 A1 | 2/2009 | Levin et al. |
| 2009/0054770 A1 | 2/2009 | Daigle |
| 2009/0062697 A1 | 3/2009 | Zhang et al. |
| 2009/0062873 A1 | 3/2009 | Wu et al. |
| 2009/0076409 A1 | 3/2009 | Wu et al. |
| 2009/0088623 A1 | 4/2009 | Vortman et al. |
| 2009/0112095 A1 | 4/2009 | Daigle |
| 2009/0112133 A1 | 4/2009 | Deisseroth et al. |
| 2009/0163982 A1 | 6/2009 | deCharms |
| 2009/0221939 A1 | 9/2009 | Demarais et al. |
| 2009/0247911 A1 | 10/2009 | Novak et al. |
| 2009/0264755 A1 | 10/2009 | Chen et al. |
| 2009/0306644 A1 | 12/2009 | Mayse et al. |
| 2009/0326379 A1 | 12/2009 | Daigle et al. |
| 2010/0092424 A1 | 4/2010 | Sanghvi et al. |
| 2010/0125269 A1 | 5/2010 | Emmons et al. |
| 2010/0174188 A1 | 7/2010 | Wang et al. |
| 2011/0028867 A1 | 2/2011 | Choo et al. |
| 2011/0118602 A1 | 5/2011 | Weng et al. |
| 2011/0178403 A1 | 7/2011 | Weng et al. |
| 2011/0178445 A1 | 7/2011 | Weng et al. |
| 2011/0230763 A1 | 9/2011 | Emery et al. |
| 2011/0230796 A1 | 9/2011 | Emery et al. |

FOREIGN PATENT DOCUMENTS

| | | |
|---|---|---|
| EP | 1265223 | 12/2002 |
| EP | 1874192 A1 | 10/2006 |
| EP | 2181342 A1 | 2/2009 |
| EP | 2303131 | 12/2009 |
| FR | 2672486 | 8/1992 |
| WO | WO 9731364 | 8/1997 |
| WO | WO 99/48621 | 9/1999 |
| WO | WO 0072919 | 12/2000 |
| WO | WO 01/34018 | 5/2001 |
| WO | WO 02069805 | 9/2002 |
| WO | WO 2005/030295 | 4/2005 |
| WO | WO 2006/113445 | 10/2006 |
| WO | WO 2009/018394 | 2/2009 |
| WO | WO 2009/026534 | 2/2009 |
| WO | WO 2009/158399 | 12/2009 |
| WO | WO 2011/053757 | 5/2011 |
| WO | WO 2011/053772 | 5/2011 |

OTHER PUBLICATIONS

Amenta et al., "A New Voronoi-Based Surface Reconstruction Algorithm." Computer Graphics: 7pp, 1998.

American Red Cross., "Blood 101." 4pp., Dec. 11, 2007.

Anand et al., "Monitoring formation of high intensity focused ultrasound (HIFU) induced lesions using backscattered ultrasound." Acoustical Society of America; Mar. 10, 2004.

Anand et al., "Using the ATL 1000 to Collect Domodulated RF Data for Monitoring HIFU Lesion Formation." Presented at SPIE Medical Imaging 2003. 11pp, 2003.

Aurenhammer, F. "Voronoi diagrams—A Survey of a Fundamental Geometric Data Structure." ACM Computing Surveys, vol. 23, No. 3: 345-405, Sep. 1991.

Bachmann et al., "Targeting Mucosal Addressin Cellular Adhesion Molecule (MAdCAM)-1 to Noninvasively Image Experimental Crohn's Disease." Gastroenterology; vol. 130: 8-16, 2006.

Barthe et al. "Efficient Wideband Linear Arrays for Imaging and Therapy" IEEE Ultrasonics Symposium. pp. 1249-1252 (1999).

Bauer et al., "Ultrasound Imaging with SonoVue: Low Mechanical Index Real-Time Imaging." Acad. Radiol.; vol. 9, Suppl. 2: S282-S284, 2002.

Beard et al., "An Annular Focus Ultrasonic Lens for Local Hyperthermia Treatment of Small Tumors." Ultrasound in Medicine & Biology; vol. 8, No. 2: 177-184, 1982.

Bokarewa et al., "Tissue factor as a proinflammatory agent." Arthritis Research, vol. 4: 190-195, Jan. 10, 2002.

Bots et al., "Intima Media Thickness as a Surrogate Marker for Generalised Atherosclerosis." Cardiovascular Drugs and Therapy, ProQuest Medical Library; vol. 16, No. 4: 341-351, Jul. 2002.

Brayman et al., "Erosion of Artificial Endothelia In Vitro by Pulsed Ultrasound: Acoustic Pressure, Frequency, Membrane Orientation and Microbubble Contrast Agent Dependence." Ultrasound in Medicine & Biology; vol. 25, No. 8: 1305-1320, 1999.

Buller et al., "Accurate Three-dimensional Wall Thickness Measurement From Multi-Slice Short-Axis MR Imaging." Computers in Cardiology, 245-248, 1995.

Byram et al., "3-D Phantom and In Vivo Cardiac Speckle Tracking Using a Matrix Array and Raw Echo Data." IEEE Transactions on Ultrasonics, Ferroelectrics, and Frequency Control, vol. 57, No. 4; 839-854, Apr. 2010.

Campese, V., Krol, E. Neurogenic Factors in Renal Hypertension. Current Hypertension Reports 2002, 4:256-260.

Canadian Examination Report dated Nov. 14, 2007 in CA Patent Application 2,387,127, filed Oct. 25, 2000.

Chao et al., "Aspheric lens design." Ultrasonics Symposium, 2000 IEEE, vol. 2: Abstract Only, Oct. 2000.

Chelule et al., "Fabrication of Medical Models From Scan Data via Rapid Prototyping Techniques." 9 pp., Feb. 7, 2007.

Chen et al., "A comparison of the fragmentation thresholds and inertial cavitation doses of different ultrasound contrast agents." Journal of the Acoustical Society of America, vol. 113, No. 1: 643-665, Jan. 2003.

Chen et al., "Inertial Cavitation Dose and Hemolysis Produced In Vitro With or Without Optison." Ultrasound in Medicine & Biology, vol. 29, No. 5: 725-737, 2003.

Chen et al., DC-Biased Electrostrictive Materials and Transducers for Medical Imaging, 1997 IEEE Ultrasonics Symposium, IEEE, Aug. 1997.

Chong et al., "Tissue Factor and Thrombin Mediate Myocardial lschemia-Reperfusion Injury." The Society of Thoracic Surgeons, vol. 75: S649-655, 2003.

Damianou, et al., "Application of the Thermal Dose Concept for Predicting the Necrosed Tissue Volume During Ultrasound Surgery", IEEE Ultrasonic Symposium, (1993) 1199-1202.

Dayton et al., "The magnitude of radiation force on ultrasound contrast agents." Journal of the Acoustical Society of America, vol. 112, No. 5, Part 1: 2183-2192, Nov. 2002.

Dempsey et al., "Thickness of Carotid Artery Atherosclerotic Plaque and Ischemic Risk." Neurosurgery, vol. 27, No. 3: 343-348, 1990.

Dewhirst, et al., "Basic principles of thermal dosimetry and thermal thresholds for tissue damage from hyperthermia", Int. J. Hyperthermia, (2003) 19(3):267-294.

Dibona, G. F., et al., Chaotic behavior of renal sympathetic nerve activity: effect of baroreceptor denervation and cardiac failure, Am J Physiol Renal Physiol, 279:F491-501, 2000.

Dibona, G.F.: "Neural control of the kidney: functionally specific renal sympathetic nerve fibers." Am J. Physiol Regulatory Integrative Comp Physiol 279: R1517-1524, 2000.

Dibona, GF. Functionally Specific Renal Sympathetic Nerve Fibers: Role in Cardiovascular Regulation. American Journal of Hypertension. 2001 vol. 14(6) 163S-170S.

Doumas, M., et al., Renal Sympathetic Denervation: The Jury is Still Out, The Lancet, Nov. 2010, vol. 376, Issue 9756, pp. 1878-1880.

Ebbini et al., "Image-guided noninvasive surgery with ultrasound phased arrays." SPIE, vol. 3249: 230-239, Apr. 2, 1998.

Edelsbrunner, Herbert. "Geometry and Topology for Mesh Generation." Cambridge University Press: 68pp, 2001.

Esler, Murray D., et al., Renal sympathetic denervation in patients with treatmentresistant hypertension (The Symplicity HTN-2 Trial): a randomised controlled trial, Nov. 2010, The Lancet, vol. 376, Issue 9756, pp. 1903-1909.

European Examination Report dated Mar. 7, 2008 in EP Patent Application 989717.4, filed Oct. 25, 2000.

Everbach et al., "Cavitational Mechanisms in Ultrasound-Accelerated Thrombolysis at 1 MHz." Ultrasound in Medicine & Biology, vol. 26, No. 7: 1153-1160, 2000.

Ewert et al., "Anti-myeloperoxidase antibodies stimulate neutrophils to damage human endothelial cells." Kidney International, vol. 41: 375-383, 1992.

Fjield et al.; "A parametric study of the concentric-ring transducer design for MRI guided ultrasound surgery." J. Acoust. Soc. Am 100 (2) Pt. 1, Aug. 1996.

Ganapathy et al., "A New General Triangulation Method for Planar Contours." Computer Graphics vol. 16, No. 3:69-75, 1982.

Grassi, G. Role of the Sympathetic Nervous System in Human Hypertension. Journal of Hypertension. 1998, 16: 1979-1987.

Gray, Henry. "The Skull." Anatomy of the Human Body: 7pp., 1918.

Guzman et al., "Ultrasound—Mediated Disruption of Cell Membranes. I. Quantification of Molecular uptake and Cell Viability. / II. Heterogeneous effects on cells." Journal of the Acoustical Society of America, vol. 110, No. 1: 588-606, Jul. 2001.

Hachimine, K. et. al. Sonodynamic Therapy of Cancer Using a Novel Porphyrin Derivative, DCPH-P-Na(I),which is Devoid of Photosensitivity. Cancer Science 2007; 98: 916-920.

Hadimioglu et al., "High-Efficiency Fresnel Acoustic Lenses." Ultrasonics Symposium 1993 IEEE:579-582, 1993.

Han et al., "A Fast Minimal Path Active Contour Model." IEEE Transactions on Image Processing, vol. 10, No. 6: 865-873, Jun. 2001.

Hatangadi, Ram. "A Novel Dual Axis Multiplanar Transesophageal Ultrasound Probe for Three-Dimensional Echocardiograph." University of Washington, Department of Sciences and Engineering, vol. 55-11B: Abstract 1pg, 1994.

Holt et al., "Bubbles and Hifu: the Good, the Bad and the Ugly." Boston University, Department of Aerospace and Mechanical Engineering: 120-131, 2002.

Hubka et al., "Three-dimensional echocardiographic measurement of left ventricular wall thickness: In vitro and in vivo validation." Journal of the American Society of Echocardiography, vol. 15, No. 2: 129-135, 2002.

Hutchinson et al. "Intracavitary Ultrasound Phased Arrays for Noninvasive Prostate Surgery." IEEE Transactions on Ultrasonics. Ferroelectrics, and Frequency Control. 43(6):1032-1042 (1996).

Hwang et al., "Vascular Effects Induced by Combined 1-MHz Ultrasound and Microbubble Contrast Agent Treatments In Vivo." Ultrasound in Medicine & Biology, vol. 31, No. 4: 553-564, 2005.

Hynynen et al., "Potential Adverse Effects of High-Intensity Focused Ultrasound Exposure on Blood Vessels In Vivo." Ultrasound in Medicine & Biology, vol. 22, No. 2: 193-201, 1996.

Iannuzzi et al., "Ultrasonographic Correlates of Carotid Atherosclerosis in Transient Ischemic Attack and Stroke." Stroke, ProQuest Medical Library, vol. 26, No. 4: 614-619, 1995.

Idell et al., "Fibrin Turnover in Lung Inflammation and Neoplasia." American Journal of Respiratory and Critical Care Medicine, vol. 163: 578-584, 2001.

Indman, Paul. "Alternatives in Gynecology." Hysteroscopy, OBGYN.net, Oct. 14, 2004. http://www.gynalternatives.com/hsc.html.

International Preliminary Report on Patentability dated Jun. 5, 2003 for PCT Application No. PCT/US00/35262.

International Search Report and Written Opinion dated Apr. 23, 2001 for PCT Application No. PCT/US00/35262.

International Search Report and Written Opinion dated Aug. 4, 2005 for PCT Application No. PCT/US2005/001893.

International Search Report and Written Opinion dated Jul. 11, 2007 for PCT Application No. PCT/US2006/041163.

International Search Report and Written Opinion dated Jun. 30, 2008 for PCT Application No. PCT/US2007/087310.

International Search Report and Written Opinion dated Mar. 30, 2007 for Application No. PCT/US2006/027688 filed on Jul. 13, 2006.

International Search Report and Written Opinion dated May 18, 2001 for PCT Application No. PCT/US00/41606.

International Search Report and Written Opinion dated May 29, 2007 for PCT Application No. PCT/US04/31506.

Invitation to Pay Additional Fees and Partial International Search Report dated Nov. 29, 2006 for PCT Application No. PCT/US2006/027688.

Janssen, BJ and Smits, J. Renal Nerves in Hypertension. Mineral and Electrolyte Metabolism. 1090; 15:74-82, 1989.

Jolesz, F. MRI-Guided Focused Ultrasound Surgery. Annual Review of Medicine. 2009 60: 417-30.

Kaczkowski et al., "Development of a High Intensity Focused Ultrasound System for Image-Guided Ultrasonic Surgery." Ultrasound for Surgery, Oct. 14, 2004. (http://cimu.apl.washington.edu/hifusurgerysystem.html).

Kang et al., "Analysis of the Measurement Precision of Arterial Lumen and Wall Areas Using High-Resolution MRI." Magnetic Resonance in Medicine, vol. 44: 968-972, 2000.

Klibanov et al., "Detection of Individual Microbubbles of an Ultrasound contrast Agent: Fundamental and Pulse Inversion Imaging." Academy of Radiology, vol. 9, Suppl. 2: S279-S281, 2002.

Kojima, T., Matrix Array Transducer and Flexible Matrix Arry Transducer,Proceedings of the Ultrasonics Symposium, vol. 2:649-653 (1986).

Krum, H et. al. Catheter-Based Renal Sympathetic Denervation for Resistant Hypertension: a Multicentre Safety and Proof-of-Principle Cohort Study. Lancet 2009 373; 1275-81.

Krum, H. et. al. Pharmacologic Management of the Cardiorenal Syndrome in Heart FAilure. Current Heart Failure Reports 2009, 6: 105-111.

Kudo et al., "Study on Mechanism of Cell Damage Caused by Microbubbles Exposed to Ultrasound." Ultrasound in Medicine & Biology, vol. 29, Supplement: 4pp, 2003.

Lalonde et al., "Field conjugate acoustic lenses for ultrasound hyperthermia." Ultrasonics, Ferroelectrics and Frequency Control, IEEE Transactions, vol. 40, Issue 5: Abstract 1pg., Sep. 1993.

Martin et al., Hemostasis of Punctured Vessels Using Doppler-Guided High Intensity Ultrasound, Ultrasound in Med.& Biol., vol. 25, pp. 985-990, 1999, USA.

Meyers, D. "Multiresolution tiling." Computer Graphics, No. 5: 325-340, 1994.

Miller et al., "A Review of In Vitro Bioeffects of Inertial Ultrasonic Cavitation From a Mechanistic Perspective." Ultrasound in Medicine & Biology, vol. 22, No. 9: 1131-1154, 1996.

Miller et al., "Diagnostic ultrasound activation of contrast agent gas bodies induces capillary rupture in mice." PNAS, vol. 97, No. 18: 10179-10184, 2000.

Moss, Nicholas G. Renal Function and Renal Afferent and Efferent Nerve Activity. American Journal Physiology. 243 (Renal Fluid Electrolyte Physiology) 12: F425-F433, 1982.

N.a., "Breast Cancer—Insightec: focused ultrasound for non invasive treatment." FAQ, Oct. 14, 2004. (http://www.exablate2000.com/physicians_faq.html).

N.a., "Cavitation." Ultrasound TIP—U.S. Database: Dec. 12, 2007.

N.a., "Mechanical Bioeffects in the Presence of Gas-Carrier Ultrasound Contrast Agents." Journal of Ultrasound & Medicine, vol. 19: 120-142, 2000.

Ng et al., "Therapeutic Ultrasound: Its Application in Drug Delivery." Medicinal Research Reviews, vol. 22, No. 2: 204-233, 2002.
Notice of Allowance dated Mar. 25, 2003 from U.S. Appl. No. 09/696,076, filed Oct. 25, 2000.
Office Action dated Apr. 29, 2011 for U.S. Appl. No. 12/202,195.
Office Action dated Apr. 6, 2010 for U.S. Appl. No. 11/619,996.
Office Action dated Aug. 17, 2006 from U.S. Appl. No. 10/671,417, filed Sep. 24, 2003.
Office Action dated Feb. 18, 2011 for U.S. Appl. No. 11/583,656.
Office Action dated Jan. 7, 2011 for U.S. Appl. No. 12/762,938.
Office Action dated Jul. 14, 2009 for U.S. Appl. No. 11/619,996.
Office Action dated Jul. 31, 2007 from U.S. Appl. No. 10/671,417, filed Sep. 24, 2003.
Office Action dated Jul. 5, 2006 for U.S. Appl. No. 10/616,831.
Office Action dated Jul. 9, 2008 for U.S. Appl. No. 11/486,528.
Office Action dated Jun. 28, 2010 for U.S. Appl. No. 12/247,969.
Office Action dated Mar. 18, 2011 for U.S. Appl. No. 12/247,969.
Office Action dated Mar. 4, 2011 for U.S. Appl. No. 11/583,569.
Office Action dated Nov. 16, 2010 for U.S. Appl. No. 12/202,195.
Office Action dated Nov. 29, 2002 from U.S. Appl. No. 09/696,076, filed Oct. 25, 2000.
Office Action dated Oct. 19, 2009 for U.S. Appl. No. 11/486,526.
Office Action dated Oct. 19, 2009 for U.S. Appl. No. 11/583,256.
Office Action dated Sep. 16, 2010 for U.S. Appl. No. 11/583,656.
O'Leary et al., "Carotid-artery Intima and Media Thickness as a Risk Factor for Myocardial Infarction and Stroke in Older Adults." Cardiovascular Health Study Collaborative Research Group. New England Journal of Medicine, vol. 340, No. 1: 14-22, Jan. 7, 1999.
Ostensen et al., "Characterization and Use of Ultrasound Contrast Agents." Academy of Radiology, vol. 9, Suppl. 2: S276-S278, 2002.
Owaki et al., "The Ultrasonic Coagulating and Cutting System Injuries Nerve Function." Endoscopy, vol. 34, No. 7: 575-579, 2002.
Pernot, et al., "Temperature Estimation Using Ultrasonic Spatial Compound Imaging", IEEE Transactions on Ultrasonics, Ferroelectrics, and Frequency Control, (May 2004) 51(5):606-615.
Pignoli et al., "Intimal plus medial thickness of the arterial wall: a direct measurement with ultrasound imaging." Circulation, vol. 74, No. 6:1399-1406, Dec. 1986.
Poliachik et al., "Activation, Aggregation and Adhesion of Platelets Exposed to High-Intensity Focused Ultrasound." Ultrasound in Medicine & Biology, vol. 27, No. 11: 1567-1576, 2001.
Poliachik et al., "Effect of High—Intensity Focused Ultrasound on Whole Blood With or Without Microbubble Contrast Agent." Ultrasound in Medicine & Biology, vol. 25, No. 6:991-998, 1999.
Porter et al., "Ultrasound, Microbubbles and Thrombolysis." Progress in Cardiovascular Diseases, vol. 44, No. 2: 101-110, Oct. 2001.
Recchia et al., Ultrasonic Tissue Characterization of Blood during Stasis and Thrombosis with a Real-Time Linear-Array Backscatter Imaging System., Coronary Artery Disease, 1993, 4:987-994.
Rivens et al., "Vascular Occlusion Using Focused Ultrasound Surgery for Use in Fetal Medicine." European Journal of Ultrasound, vol. 9: 89-97, 1999.
Rose, Joseph, Source Influence Ultrasonic Waves in Solid Media, pp. 200-227, Cambridge University Press, 1999, USA.
Rosen et al., "Vascular Occlusive Diseases." 37pp., revised 2002.
Rosenschein et al., "Shock-Wave Thrombus Ablation, A New Method for Noninvasive Mechanical Thrombolysis." The American Journal of Cardiology, vol. 70, Issue 15: Abstract, Nov. 15, 1992.
Rosenschein et al., "Ultrasound Imaging-Guided Nonivasive Ultrasound Thrombolysis-Preclinical Results." Circulation, vol. 102: 238-245, 2000. (http://www.circulationaha.com.org).
Sanghvi et al. "High-Intensity Focused Ultrasounds." Experimental and Investigational Endoscopy. 4(2):383-395 (1994).
Schlaich, MP. Sympathetic Activation in Chronic Renal Failure. Journal American Society Nephrology 20: 933-939, 2009.
Schulte-Altedorneburg et al., "Accuracy of In Vivo Carotid B-Mode Ultrasound Compared with Pathological Analysis: Intima-Media Thickening, Lumen Diameter, and Cross-Sectional Area." Stroke, vol. 32, No. 7: 1520-1524, 2001.
Sheahan et al., Observing the Bracial Artery through a Pressure Cuff, Physiol. Meas. 14 (1993) 1-6.
Sherrit et al., The Characterisation and Modelling of Electrostrictive Ceramics for Transducers, Ferroelectrics, 228:(1-4), pp. 167-196, 1999.
Shrout et al., Classification of Electrostrictive-Based Materials for Transducers, 1993.
Shung, et al., "Ultrasonic Characterization of Blood During Coagulation", J. Clin. Ultrasound, (1984) 12:147-153.
Simon, et al, "Two-Dimensional Temperature Estimation Using Diagnostic Ultrasound", IEEE Transactions on Ultrasonics, Ferroelectrics, and Frequency Control, (Jul. 1998) 45(4):1088-1099.
Tachibana et al., "Albumin Microbubble Echo-Contrast Material as an Enhancer for Ultrasound Accelerated Thrombolysis." Circulation, vol. 92: 1148-1150, 1995.
Tachibana et al., "The Use of Ultrasound for Drug Delivery." Echocardiography, vol. 18, No. 4: 323-328, May 2001.
Tardy et al., "In Vivo Ultrasound Imaging of Thrombi Using a Target-specific Contrast Agent." Academy of Radiology, vol. 9, Suppl. 2: S294-S296, 2002.
Ter Haar. G. 'Ultrasound Focal Beam Surgery. Ultrasound in Medicine and Biology. 21(9):1089-1100 (1995).
Vaezy et al., "Hemostasis of Punctured Blood Vessels Using High Intensity Focused Ultrasound," Ultrasound in Med.& Biol., vol. 24, No. 6, pp. 903-910,1998, USA.
Vaezy et al., "Acoustic surgery." Physics World: 35-39, Aug. 2001.
Vaezy et al., "Hemostasis and Tumor Treatment using High Intensity Focused Ultrasound: Experimental Investigations and Device Development." First International Workshop on the Application of HIFU in Medicine: 46-49, 2001.
Vaezy et al., "Hemostasis using high intensity focused ultrasound." European Journal of Ultrasound, vol. 9: 79-87, 1999.
Vaezy et al., "Intra-operative acoustic hemostasis of liver: production of a homogenate for effective treatment." Ultrasonics, vol. 43: 265-269, 2005.
Vaezy et al., Use of High-Intensity Focused Ultrasound to Control Bleeding, Mar. 1999, J Vasc Surg, vol. 29, pp. 533-542.
Valente, JF et. al. Laparoscopic Renal Denervation for Intractable ADPKD Related Pain. Nephrology Dialysis and Transplantation. 2001 16:160.
Von Land et al., "Development of an Improved Centerline Wall Motion Model." IEEE: 687-690, 1991.
Watkin et al., "Multi-Modal Contrast Agents: A First Step." Academy of Radiology, vol. 9, Suppl. 2: S285-S287, 2002.
Wickline et al., "Blood Contrast Enhancement with a Novel, Non-Gaseous Nanoparticle Contrast Agent." Academy of Radiology, vol. 9, Suppl. 2: S290-S293, 2002.
Williamson et al., "Color Doppler Ultrasound Imaging of the Eye and Orbit." Survey of Ophthamology, vol. 40, No. 4: 255-267, 1996.
Yu et al., "A microbubble agent improves the therapeutic efficiency of high intensity focused ultrasound: a rabbit kidney study." Urological Research, PubMed: Abstract, 2004.
Office Action dated Dec. 30, 2011 for U.S. Appl. No. 12/896,740.
Office Action dated Dec. 15, 2011 for U.S. Appl. No. 13/026,108.
Office Action dated Dec. 8, 2011 for U.S. Appl. No. 11/955,310.
Office Action dated Nov. 30, 2011 for U.S. Appl. No 13/011,533.
Office Action dated Oct. 25, 2011 for U.S. Appl. No. 13/025,959.
International Search Report and Written Opinion dated Jun. 6, 2011 for PCT Application No. PCT/US2010/052197 (KM-003-PCT).
International Search Report and Written Opinion dated Dec. 6, 2010 for PCT Application No. PCT/US2010/052193 (KM-004-PCT).
International Search Report and Written Opinion dated Jul. 27, 2011 for PCT Application No. PCT/US2011/033337.
Office Action dated Apr. 10, 2012 for U.S. Appl. No. 12/725,450.
Office Action dated Apr. 6, 2012 for U.S. Appl. No. 12/685,655.
Office Action dated Mar. 20, 2012 for U.S. Appl. No. 13/246,775.
Office Action dated Nov. 28, 2011 for U.S. Appl. No. 13/246,763.
Office Action dated Feb. 3, 2012 for U.S. Appl. No. 13/245,689.
Final Office Action dated Jun. 13, 2012 for U.S. Appl. No. 13/245,689.
Office Action dated Jun. 11, 2012 for U.S. Appl. No. 13/346,466.
Office Action dated Jun. 7, 2012 for U.S. Appl. No. 13/344,418.
Final Office Action dated Jun. 5, 2012 for U.S. Appl. No. 12/896,740.
Office Action dated May 24, 2012 for U.S. Appl. No. 13/118,144.
Final Office Action dated May 14, 2012 for U.S. Appl. No. 12/026,108.
Final Office Action dated May 10, 2012 for U.S. Appl. No. 11/583,656.
Final Office Action dated May 2, 2012 for U.S. Appl. No. 13/011,533.

* cited by examiner

SYSTEM AND METHOD FOR TREATING A THERAPEUTIC SITE

CROSS-REFERENCE TO RELATED APPLICATIONS

This application is a continuation of co-pending U.S. application Ser. No. 13/118,245, filed May 27, 2011, which is a continuation of U.S. application Ser. No. 11/583,569, filed Oct. 19, 2006, now U.S. Pat. No. 8,167,805 which claims the benefit of U.S. Provisional Application No. 60/728,783, filed Oct. 20, 2005 and U.S. Provisional Application No. 60/808,665, filed May 26, 2006, all of which are incorporated herein by reference in their entirety.

BACKGROUND

1. Field of the Invention

This disclosure relates to systems of methods for locating arteriotomies. In some embodiments, the localization is used for therapeutic targeting (e.g., for targeting of high-intensity focused ultrasound).

2. Description of the Related Art

Certain medical procedures result in bleeding penetration wounds inside the body, for example via the insertion of devices into blood vessels and/or organs. Representative procedures include arterial and venous catheterization for cardiologic or radiologic interventional procedures, needle biopsy procedures, and minimally invasive surgery. Improved percutaneous catheterization techniques have enabled physicians to perform an ever-increasing number of diagnostic and therapeutic cardiovascular procedures using devices deployed through arteries and veins. The annual number of therapeutic and diagnostic catheterization procedures worldwide is over 14 million and it is continuously growing.

In the vast majority of these catheterization procedures, access to the vasculature is accomplished by percutaneous installation of an introducer sheath into the common femoral artery. The introducer sheath facilitates passage of a variety of diagnostic and therapeutic instruments and devices into the vessel and its tributaries. At the conclusion of the catheterization procedure, the introducer sheath is removed, leaving an arteriotomy that must be sealed. Arteriotomy hemostasis is most often (approximately two-thirds of all cases) achieved by the application of manual or mechanical compression (standard compression) on the puncture site until a stable clot forms. Several important limitations are associated with the use of standard compression. For example, a physician, nurse, or trained technician must apply digital pressure on the access site for up to 40 minutes. Patients must remain on bed rest for three or more hours so as not to disrupt clot formation in the arteriotomy. The most painful aspects of the catheterization procedure reported by patients are the standard compression procedure and lying immobile for hours. The aggressive use of anticoagulants and antiplatelet therapies to prevent thrombus formation during catheterization procedures has greatly increased the difficulty of sealing the access site using compression. Finally, complications occur, the most frequent of which are the formation of hematomas, pseudo-aneurysms, and/or arteriovenous fistulae.

Products for sealing arteriotomies based on newer technologies such as collagen plugs, sealants and mechanical suturing are being successfully marketed. However, these products are invasive, implant foreign materials, require skill and training to use, and can cause major complications. Accordingly, there is a need for improved systems and methods for sealing arteriotomies

SUMMARY OF THE INVENTION

One embodiment described herein includes an arteriotomy targeting catheter having an arteriotomy targeting aid coupled to the catheter and adapted to detect the location of an arteriotomy and one or more beacons coupled to the catheter proximal to the arteriotomy targeting aid. In one embodiment, the arteriotomy targeting aid comprises an inflatable balloon. In one embodiment, the balloon comprises an elastic polymeric material. In one embodiment, the soft elastic polymeric material is selected from the group consisting of one or more of a polyamide, a polyamide blend, a polyethylene, a polyethylene terephthalate, a polyurethane, a polyamide, and a polyamide blend. In one embodiment, the polyamide blend is PBAX. In one embodiment, the durometer of the balloon material is between 20 A and 90 D. In one embodiment, the durometer of the balloon material is between 80 A and 65 D. In one embodiment, the durometer of the balloon material is 90 A. In one embodiment, the arteriotomy targeting aid comprises a mechanical expansible device. In one embodiment, the arteriotomy targeting aid comprises an arteriotomy locating sensor. In one embodiment, the arteriotomy locating sensor comprises a temperature sensor. In one embodiment, the temperature sensor is a thermistor. In one embodiment, the arteriotomy locating sensor comprises a flow measurement sensor. In one embodiment, the arteriotomy locating sensor comprises an optical sensor. In one embodiment, the arteriotomy locating sensor comprises an impedance sensor. In one embodiment, the arteriotomy locating sensor comprises a Doppler sensor. In one embodiment, the beacon comprises an ultrasonic transmitter. In one embodiment, the beacon comprises a radio frequency transmitter. In one embodiment, the beacon comprises a magnetic field generator.

Another embodiment described herein includes a method of determining the location of a therapeutic site in a body, comprising inserting a catheter into the body, wherein the catheter comprises a targeting aid, and manipulating the catheter such that the targeting aid is adjacent to or at the therapeutic site. In one embodiment, the therapeutic site is an arteriotomy. In one embodiment, manipulating the catheter comprises moving the catheter until a Doppler signal from the targeting aid determines that the targeting aid is adjacent to or at the therapeutic site. In one embodiment, the targeting aid comprises a temperature sensor and manipulating the catheter comprises moving the catheter until the temperature sensor indicates that it is adjacent to or at the therapeutic site. In one embodiment, the targeting aid comprises a fluid flow detector and manipulating the catheter comprises moving the catheter until the fluid flow detector indicates that it is adjacent to or at the therapeutic site. In one embodiment, the targeting aid comprises an optical sensor and manipulating the catheter comprises moving the catheter until the optical sensor indicates that it is adjacent to or at the therapeutic site. In one embodiment, the targeting aid comprises a pressure sensor and manipulating the catheter comprises moving the catheter until the pressure sensor indicates that it is adjacent to or at the therapeutic site. In one embodiment, the targeting aid comprises an impedance sensor and manipulating the catheter comprises moving the catheter until the impedance sensor indicates that it is adjacent to or at the therapeutic site. In one embodiment, the targeting aid comprises a force detector and manipulating the catheter comprises moving the catheter until the force detector indicates that it is adjacent to or at the therapeutic site. In one embodiment, the targeting aid comprises a mechanically expansive device and the method comprises expanding the mechanically expansive device and moving the catheter until the device is adjacent to or at the therapeutic site. In one embodiment, the targeting aid comprises an inflatable balloon and the method comprises inflating the balloon and moving the catheter until the balloon is adjacent to or at the therapeutic site. In one embodiment, the therapeutic site is an arteriotomy created by an introducer sheath inserted into an artery, inserting the catheter into the body comprises inserting the catheter and targeting aid through the lumen of the introducer sheath past the arteriotomy and into the artery, and manipulating the catheter comprises retracting the catheter such that the targeting aid approaches the arteriotomy. In one embodiment, the introducer sheath is retracted simultaneously with retraction of the catheter. In one embodiment, the targeting aid comprises an inflatable balloon and wherein the balloon is inflated after insertion of the catheter and prior to retracting the catheter. One embodiment further includes applying compression above the arteriotomy.

Another embodiment described herein includes a method of determining the location of a therapeutic site in a body relative to a therapeutic applicator, comprising inserting a targeting catheter into the body, identifying the location of the therapeutic site using the targeting catheter, and determining the position of the targeting catheter relative to the therapeutic applicator. In one embodiment, the therapeutic site is an arteriotomy. One embodiment further comprises aligning the therapeutic applicator with the therapeutic site based on the relative position of the targeting catheter. In one embodiment, determining the position of the targeting catheter relative to the therapeutic applicator comprises using triangulation. In one embodiment, the triangulation is based on magnetic fields. In one embodiment, the triangulation is based on acoustic signals. In one embodiment, the triangulation is based on an acoustic time-of-flight determination. In one embodiment, determining the position of the targeting catheter relative to the therapeutic applicator comprises transmitting an ultrasound signal from a transmitter located on the catheter to multiple receivers located on the therapeutic applicator. In one embodiment, the transmitter comprises a piezoelectric cylinder. In one embodiment, determining the position of the targeting catheter relative to the therapeutic applicator comprises determining the acoustic time-of-flight from the transmitter to the receivers. In one embodiment, determining the position of the targeting catheter relative to the therapeutic applicator comprises transmitting ultrasound signals from multiple transmitters located on the therapeutic applicator to a receiver located on the catheter.

Another embodiment described herein includes a method for sealing a vascular opening in a blood vessel, comprising transiently substantially occluding the blood vessel, applying energy adjacent to the vascular opening such that the opening is sealed, and removing the blood vessel occlusion. In one embodiment, the blood vessel is a fermoral, brachial, or radial artery. In one embodiment, the blood vessel is transiently fully occluded. In one embodiment, occluding the blood vessel comprises applying compressive force to the blood vessel. In one embodiment, the compressive force is applied using an energy applicator that is used to apply the energy. In one embodiment, the compressive force is applied to the surface of skin located over the blood vessel. In one embodiment, applying energy adjacent to the vascular opening comprises directing energy from an energy applicator located on or near the surface of skin over the blood vessel. In one embodiment, applying energy to the vascular opening comprises energizing an energy applicator positioned inside a patient near the vascular opening. In one embodiment, the energy applied is acoustic energy. In one embodiment, the energy applied is high intensity focused ultrasound energy. In one embodiment, the energy applied is radio frequency energy. In one embodiment, the energy applied is microwave energy. In one embodiment, the energy applied is optical energy. In one embodiment, the optical energy comprises one or more of ultraviolet, visible, near—infrared, or infrared energy. In one embodiment, the energy is thermal energy. In one embodiment, the energy is cryogenic energy.

Another embodiment described herein includes a method for sealing a vascular opening in a blood vessel in a patient, comprising inserting a targeting catheter into the blood vessel, locating the vascular opening using the targeting catheter, aligning a therapeutic energy applicator relative to the targeting catheter, initiating a station keeping algorithm configured to detect relative motion between tissue in the vicinity of the vascular opening and the applicator, and applying energy from the applicator to tissue adjacent to the vascular opening to seal the opening. In one embodiment, inserting the targeting catheter comprises inserting the catheter through the vascular opening. In one embodiment, the vascular opening is created by insertion of an introducer sheath and inserting the targeting catheter comprises inserting the catheter through the sheath. In one embodiment, locating the vascular opening comprises manipulating the targeting catheter until a targeting aid on the catheter is adjacent to or at the vascular opening. In one embodiment, aligning the therapeutic energy applicator comprises detecting the position of the applicator relative to a beacon located on the catheter. In one embodiment, detecting the position of the applicator relative to the beacon comprises emitting an ultrasonic signal from the beacon to multiple receivers on the applicator. In one embodiment, the energy is high intensity focused ultrasound. One embodiment includes withdrawing the catheter from the blood vessel prior to applying energy from the applicator. In one embodiment, the targeting catheter remains in the patient's body during application of the energy. In one embodiment, the targeting catheter is removed from the patient's body prior to application of the energy. One embodiment includes applying pressure to the blood vessel to transiently partially or fully occlude the vessel prior to initiating station keeping.

Another embodiment described herein includes a method of detecting tissue movement relative to an ultrasound applicator, comprising emitting first ultrasonic pulses from at least three ultrasound transducers to a target point in the tissue, detecting first ultrasonic echoes with the ultrasound transducers, emitting second ultrasonic pulses from the ultrasound transducers, detecting second ultrasonic echoes with the ultrasound transducers, comparing the first and second ultrasonic echoes, and determining the amount of relative tissue movement using the comparison and directional vectors between the ultrasound transducers and the target point. In one embodiment, comparing the first and second ultrasonic echoes comprises determining time shifts between the echoes. In one embodiment, comparing the first and second ultrasonic echoes comprises determining phase differences between the echoes. In one embodiment, determining the amount of relative tissue movement comprises executing a recursive algorithm. In one embodiment, experimentally determining the directional vectors.

Another embodiment described herein includes a method of detecting tissue movement relative to an ultrasound applicator, comprising emitting a first ultrasonic pulse from a first ultrasound transducer to a target point in the tissue, detecting a first ultrasonic echo at a second and third ultrasound transducer, emitting a second ultrasonic pulse from either the second or third ultrasound transducer to the target point, detecting a second ultrasonic echo at the first ultrasound transducer and the non-transmitting second or third ultrasound transducer, comparing the echoes to previously recorded echoes, and determining the amount of relative tissue movement using the comparison and directional vectors between the ultrasound transducers and the target point. One embodiment includes detecting the first and second ultrasonic echoes at least one additional ultrasound transducer. In one embodiment, comparing the echoes comprises determining time shifts between the detected echoes and the previously recorded echoes. In one embodiment, comparing the echoes comprises determining phase differences between the detected echoes and the previously recorded echoes. In one embodiment, determining the amount of relative tissue movement comprises executing a recursive algorithm. One embodiment includes experimentally determining the directional vectors.

Another embodiment described herein includes a method of detecting tissue movement relative to an ultrasound applicator, comprising emitting an ultrasonic pulse from a first ultrasound transducer to a target point in the tissue, detecting an ultrasonic echo at the first ultrasound transducer and at a second and third ultrasound transducer, comparing the echo to a previously recorded echo, and determining the amount of relative tissue movement using the comparison and directional vectors between the ultrasound transducers and the target point. One embodiment comprises detecting the ultrasonic echo at least one additional ultrasound transducer. In one embodiment, comparing the echo comprises determining time shifts between the detected echo and the previously recorded echo. In one embodiment, comparing the echo comprises determining phase differences between the detected echo and the previously recorded echo. In one embodiment, determining the amount of relative tissue movement comprises executing a recursive algorithm. On embodiment includes experimentally determining the directional vectors.

BRIEF DESCRIPTION OF THE DRAWINGS

FIG. 2A illustrates a sealed ovine femoral artery. FIG. 2B illustrates a sealed swine femoral artery. FIG. 2C illustrates the same artery as FIG. 2B, but viewing it from the intimal surface.

DETAILED DESCRIPTION OF CERTAIN EMBODIMENTS

Disclosed herein are systems and methods associated with an acoustic hemostasis device. This device, designed for rapid, noninvasive sealing of femoral arteriotomies using focused ultrasound technology, requires neither the prolonged application of pressure and immobilization associated with standard compression, nor implantation of any foreign material. Thus, this system has the potential to provide a superior method of arteriotomy closure. This system has been also described in U.S. Pat. No. 6,656,136, filed Oct. 25, 2000; co-pending U.S. application Ser. No. 10/671,417 filed Sep. 24, 2003; U.S. Pat. No. 6,719,694, filed Dec. 22, 2000; and U.S. Pat. No. 6,626,855, filed Nov. 22, 2000; all of which are incorporated herein by reference in their entirety.

Figure 1:
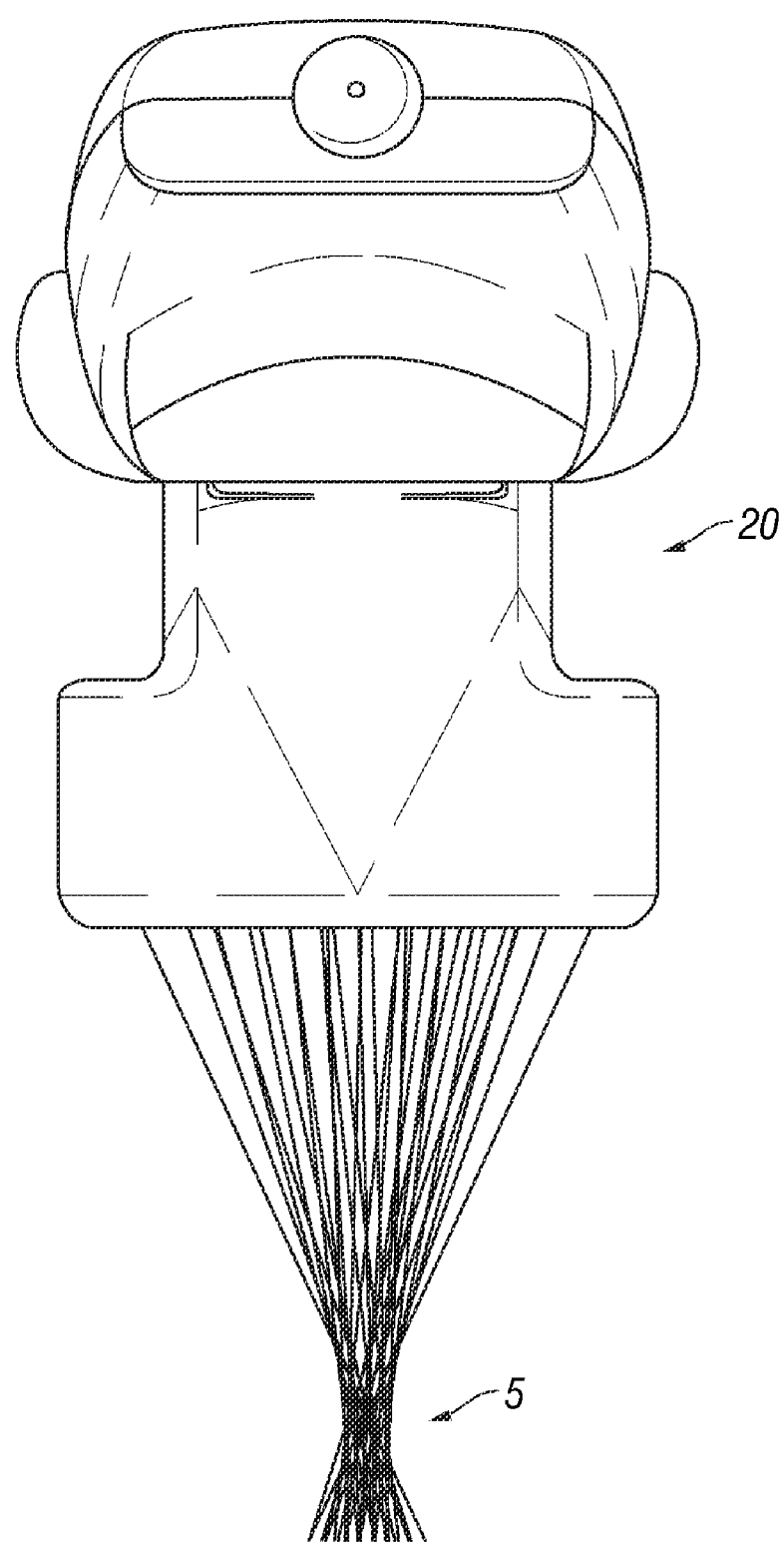
FIG. 1 depicts an ultrasound applicator and a visualization of the focused, high intensity ultrasound emitted from the applicator.

Because of its unique properties in soft tissue, medical ultrasound can be brought to a tight focus at a distance from its source. FIG. 1 depicts an ultrasound applicator 20 emitting focused ultrasound to a focal volume 5. The ultrasound energy is modeled using the Schlieren technique. FIG. 1 illustrates the ability to tightly focus ultrasound waves in soft tissue at a distance from its source. If sufficient energy is radiated from an ultrasound source (e.g. ultrasound applicator 20), tissue located in the focal volume 5 can be rapidly heated while intervening and adjacent tissues are unaffected. By precisely controlling the magnitude, location and distribution of the focused ultrasound, noninvasive therapies such as arterial puncture sealing can be rapidly and safely administered.

Animal and human studies have show that use of high-intensity focused ultrasound to locally heat punctures and lacerations in arterial and venous walls can affect rapid and durable sealing (acoustic hemostasis) of these wounds.

The acoustic hemostasis sealing mechanism relies not on blood coagulation, but rather on the formation of a thermally coagulated collagen cap that adheres to the external elastic lamina and thereby seals the arteriotomy. This method of arteriotomy closure is noninvasive, acts on collagen naturally present in the adventitial and perivascular tissues, is unaffected by periprocedural anticoagulation therapy, is effective over a spectrum of wound and vessel sizes, and occurs in a matter of seconds.

In some embodiments, successful acoustic hemostasis treatment is promoted by: (1) adequate compression of the arteriotomy to obviate bleeding, and the consequential convective heat loss, during energy delivery, and to approximate the edges of the arteriotomy; (2) accurate spatial targeting of the ultrasound energy on the arteriotomy site; and (3) sufficient ultrasound energy to coagulate (denature) native collagen in the adventitial and perivascular tissues. In some embodiments, the ultrasonic systems described herein are designed to satisfy each of these requirements over a diverse patient population and to do so while accommodating the varying skill levels of users.

In some embodiments, the ultrasonic system is intended for noninvasively sealing femoral arteriotomies and reducing time to hemostasis, ambulation and eligibility for hospital discharge in subjects who have undergone diagnostic or interventional catheterization procedures using an 8 French or smaller introducer sheath. However, the system may also be used for other purposes, with other subjects, and other catheterization procedures.

In some embodiments, the system and methods described herein may be used with other energy sources besides ultrasound sources. For example, in some embodiments, a radio frequency, microwave, optical, or thermal therapeutic applicator may be used. In some embodiments, the optical applicator may provide one or more of ultraviolet, visible, near-infrared, or infrared energy. In various embodiments, the thermal applicator may provide heating or cryogenic energy.

Histopathological examinations of extirpated ovine and porcine arteries treated with varying doses (i.e., intensity and duration of exposure) of focused ultrasound that exceeded the threshold dose for arteriotomy sealing were performed to elucidate the healing pathway subsequent to acoustic hemostasis. Generally, within 14 days post catheterization using a 5F introducer sheath, the blood clots that form in the arteriotomy, adventitia and perivascular tissue were infiltrated with spindle-shaped transformed smooth muscle cells that produced collagen matrix. There was minimal to mild neointimal proliferation lining the lumen of the artery in the areas of trauma from the catheter puncture, and the neointima was covered by intact endothelium with no evidence of mural thrombus formation in the treated areas.

The arteries examined 30 days following the acoustic hemostasis procedure were completely healed. The neointima was well organized, covered by intact endothelium, and increased only a minimal amount from the thickness at 14 days post treatment. Neovascularization of the healed tissue and neointima was more prominent than at 14 days and appeared to be stabile by 60 days post treatment.

At 60 days following catheterization, the arteries were completely healed and quiescent. The neointima was stabile, covered with endothelium and no longer proliferating. There was no morphological evidence of vessel wall weakness resulting from the focused ultrasound exposure.

Figure 2C:
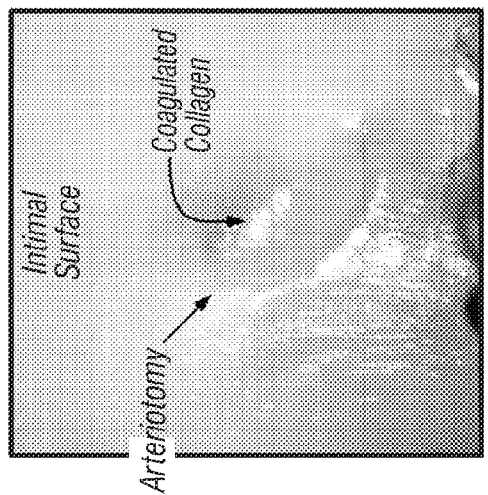
FIGS. 2A-2C are micrographs of femoral arteriotomies sealed with focused ultrasound.
Figure 2B:
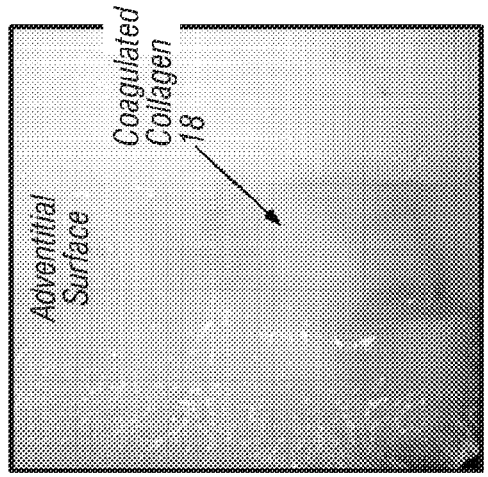
Figure 2A:
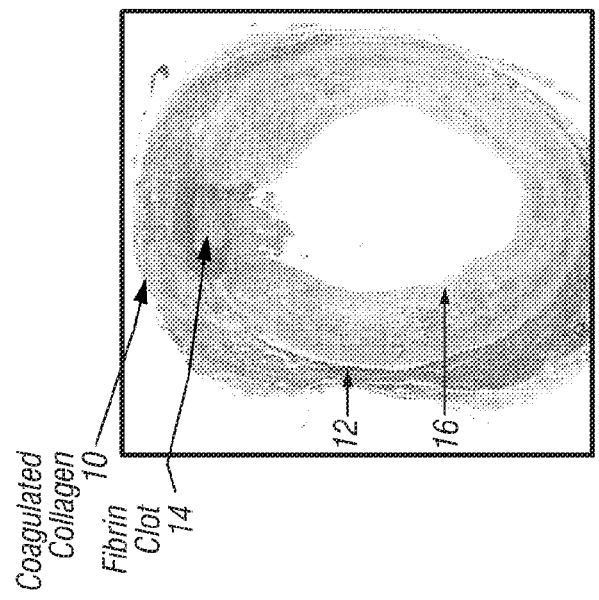

FIGS. 2A-2C illustrate microscope photographs of femoral arteriotomies sealed with focused ultrasound and then extirpated within 30 minutes of treatment. FIG. 2A is a cross-sectional photograph of an ovine femoral artery. The arteriotomy is sealed by formation of a coagulated collagen cap 10 on the external elastic lamina 12. An acute fibrin clot 14 with trapped coagulated red blood cells forms under the collagen cap and extendes partially into the vessel lumen 16. The intrinsic fibrinolytic system prevents these clots from expanding into the lumen and occluding it with an acute thrombus. FIG. 2B is a photograph of a swine femoral artery illustrating that ultrasound-induced coagulaum 18 completely covers the arteriotomy site (adventititial surface of artery) forming a robust membrane that seals the wound. FIG. 2C illustrates the same arteriotomy as FIG. 2B, but viewing it from the intimal surface. (The fibrin clot has been extracted to facilitate visualization of thermally coagulated native collagen.) Note that the coagulum typically fills about 20% of the thickness of the arterial wall from the adventitial surface.

Figure 3:
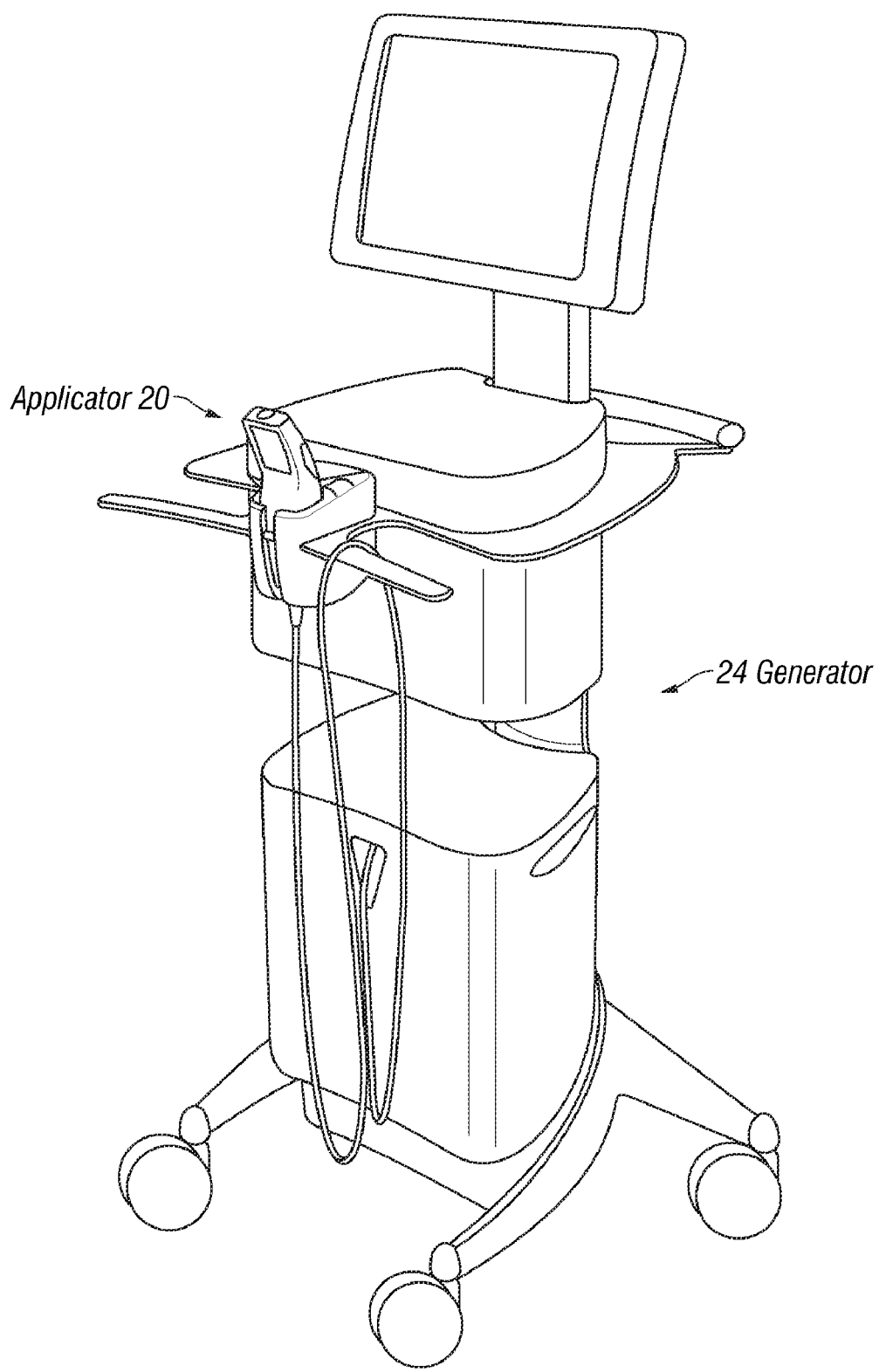
FIG. 3 is a perspective view of an acoustic hemostasis system.

In some embodiments the ultrasonic systems described herein may be a compact, mobile, self-contained, therapeutic ultrasound system. In some embodiments the ultrasonic system comprises four major components: applicator, generator, targeting catheter, and disposable patient interface (DPI). FIG. 3 illustrates one such compact system having a generator 24 on a movable cart that is connected to a hand-held ultrasound applicator 20.

Figure 4A:
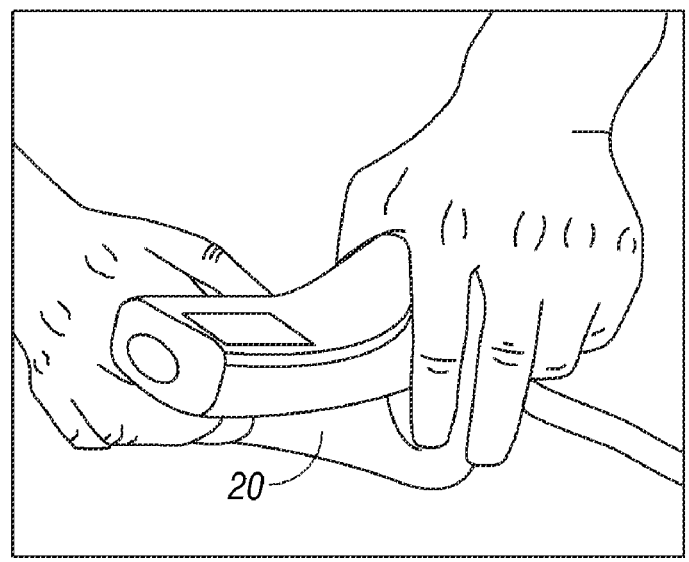
FIG. 4A depicts a hand-held therapeutic applicator being positioned onto a patient.
Figure 4B:
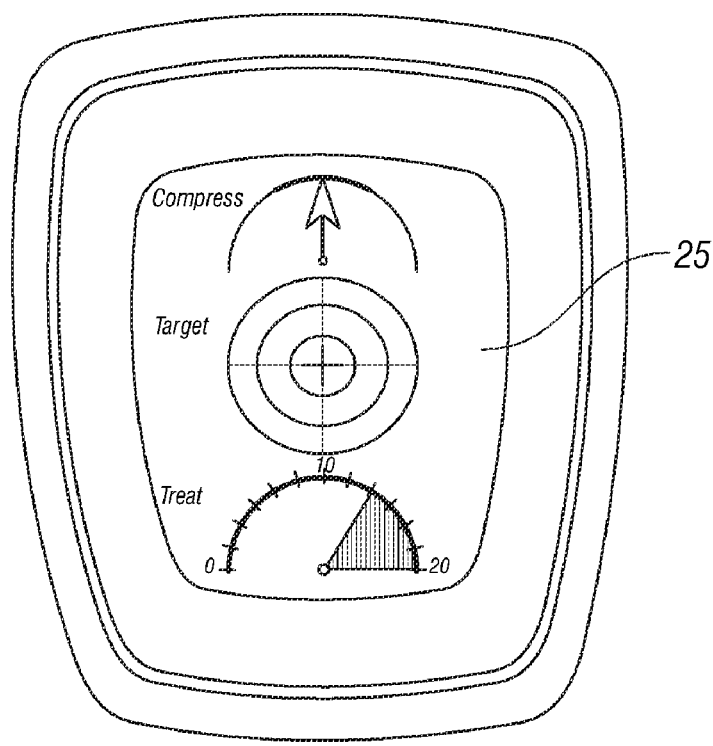
FIG. 4B is an illustration of the user interface screen located on the hand-held therapeutic applicator.

The applicator may be a handheld device that comprises an ergonomic plastic housing, a display with graphical user interface, and a multiplicity of transducers that facilitate treatment targeting, maintenance of proper arteriotomy compression during treatment, and delivery of focused ultrasound sufficient to seal the arteriotomy. As illustrated in FIG. 4A, the hand-held applicator 20 may be conveniently handled by a physician during the procedure for applying compression and properly positioning the ultrasound transducers relative to the arteriotomy. The applicator 20 may include a display 25 such as depicted in FIG. 4B to provide compression and/pr targeting feedback to the user. Although in one embodiment, the applicator provides therapeutic ultrasound, other therapeutic applications may be used (e.g., providing laser, rf, microwave, or heat energy for therapeutic use).

The generator may include a power supply; a central processing unit and operating system; and the hardware and software modules that enable the user interface, targeting, compression-monitoring, dosimetry, focused-ultrasound-energy-delivery and station-keeping functions. The generator may also provide a means to transport and maneuver the system, and to store the applicator when not in use.

The targeting catheter may include any catheter having one or more targeting aids for locating and targeting the arteriotomy. The targeting catheter may be placed down the lumen of the procedure introducer sheath or inserted in any other fashion into an artery containing an arteriotomy. In various embodiments, the targeting aid may include an inflatable balloon, force detectors, optical sensors, pressure sensors, impedance sensors, mechanically expansive devices, temperature sensors (e.g., thermisters), and/or Doppler sensors. In one embodiment, the targeting catheter features an arteriotomy locator beacon (e.g., a small ultrasound transducer) in addition to the targeting aid(s). The beacon may be used to determine the location of the beacon and/or targeting aids in reference to the therapeutic applicator. In one embodiment, the beacon is located in the catheter shaft and slightly proximal to a balloon and transmits ultrasonic pulses that serve to signal its position relative to the applicator.

The disposable patient interface, DPI, is a sterile, single-use, polymeric device that envelops the applicator and is designed to maintain the sterile field and serves as an acoustic coupling medium between the applicator and the patient's skin. Some examples of a suitable DPI are described in more detail in U.S. Application Publication No. 2005-0215901, filed Jan. 18, 2006, which is incorporated herein by reference in its entirety.

Figure 5:
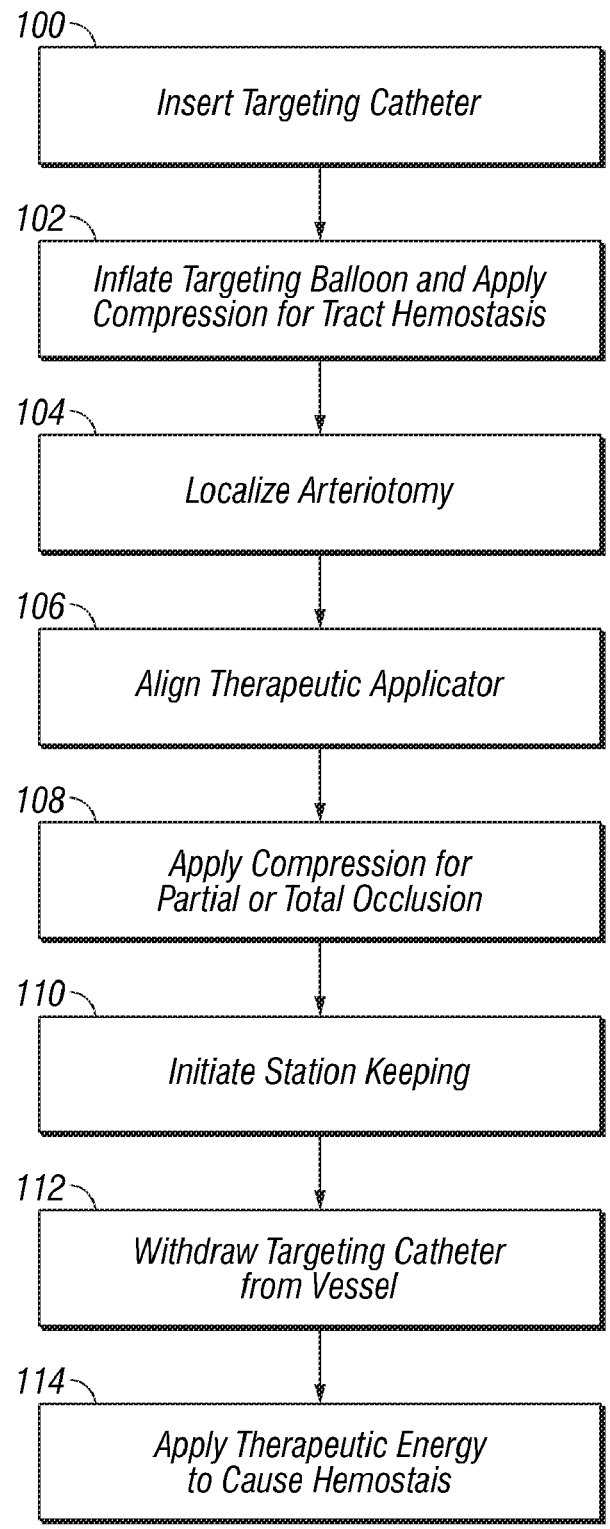
FIG. 5 is a flowchart depicting one embodiment of an overall system vascular closure procedure.

FIG. 5 is a flow chart illustrating the procedural steps for one method of performing acoustic arterial hemostasis. It will be appreciated that, depending on the embodiment, some steps may be removed or added or may be conducted in an order different from that indicted above. Each step is described in more detail below. It will also be appreciated that these steps may be used for any treatment involving focusing energy to a treatment site and not just for closing an arteriotomy.

At block 100 in FIG. 5, a targeting catheter is inserted to aid in the localization of an arteriotomy or other site where treatment is desired. In embodiments where a femoral arteriotomy is to be treated, the acoustic targeting catheter may be placed into the femoral artery through an introducer sheath prior to ultrasonic treatment. In one embodiment, this targeting catheter comprises a guidewire like device having one or more features that enable the catheter to locate an arteriotomy (e.g. using an inflatable balloon, force detectors, optical sensors, pressure sensors, impedance sensors, mechanically expansive devices, temperature sensors, and/or Doppler sensors), report the position of the arteriotomy relative to the therapy delivery device (e.g., using beacon such as an ultrasonic beacon), and/or measure blood flow properties (e.g., using sensors to measure blood velocity, volumetric flow rates, pressure, etc.).

Figure 6:
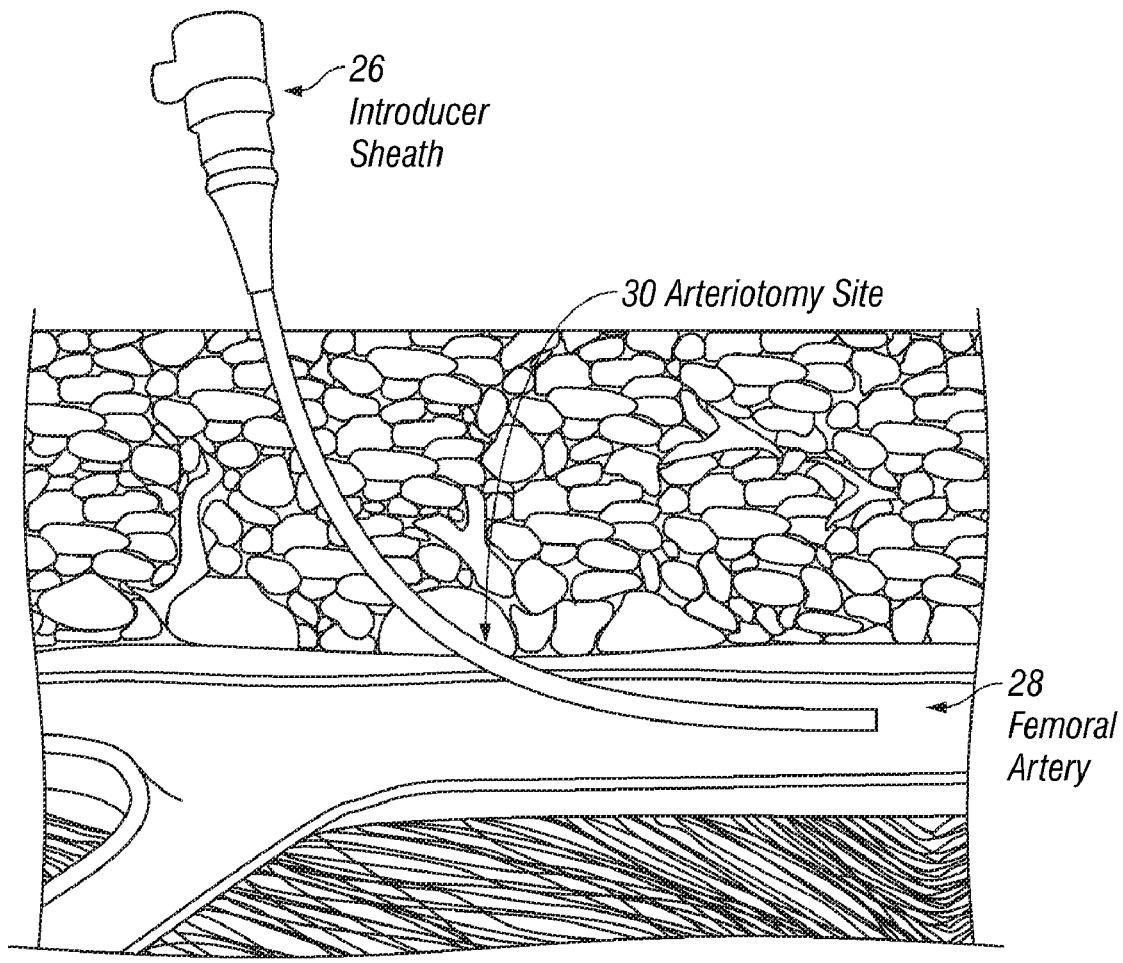
FIG. 6 is a diagram of an introducer sheath located in an femoral artery.
Figure 7A:
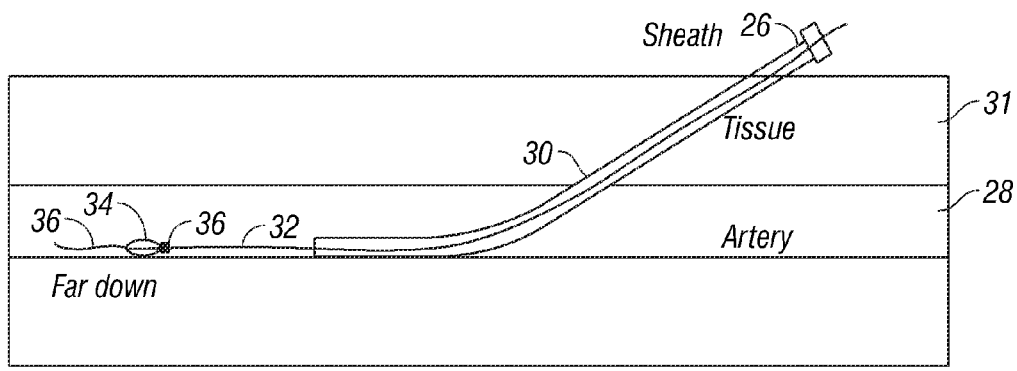
FIG. 7A is a diagram of a vascular closure procedure illustrating the insertion of a targeting catheter into a vessel through an introducer sheath.

FIG. 6 is a schematic illustrating a percutaneous catheterization procedure which involves insertion of an introducer sheath 26 into the fermoral artery 28. When the sheath is removed, the resulting arteriotomy 30 must be sealed to prevent hemorrhage. FIG. 7A is a schematic illustrating the insertion of a targeting catheter 32 through the introducer sheath 26 located in the femoral artery 28. Also depicted in the schematic is the intervening tissue 30 through which the sheath 26 extends. The targeting catheter 32 includes a targeting aid 34 (e.g., an inflatable balloon), a beacon 36, and a soft flexible tip 37 at the end of the targeting catheter 32. However, is should be noted that targeting catheters containing other features described herein may be used.

Figure 8:
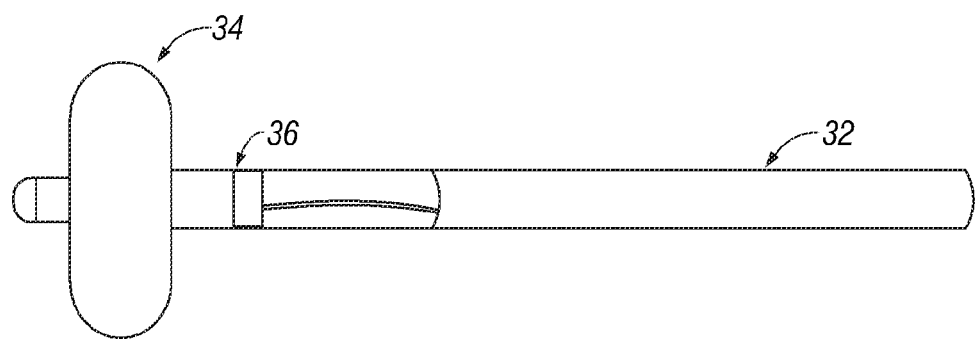
FIG. 8 is a perspective view of a balloon targeting catheter.

In one embodiment, the targeting catheter 32 includes a sterile, single-use, balloon catheter that is placed down the lumen of the procedure introducer sheath. FIG. 8 depicts a targeting catheter 32 having an inflatable balloon 34 (shown inflated) as a targeting aid and a beacon 36 (e.g., an ultrasound transducer located within the catheter shaft and slightly proximal to the balloon). As described in more detail below, the balloon 34 may be used to locate the arteriotomy. The beacon 36 may then be used to signal its position relative to the applicator, for example, by transmitting ultrasonic pulses.

In some embodiments, the catheter outside diameter is less than 4 French (1.33 mm). Thus, in some such embodiments, the beacon 36 is a micro-beacon with an outside diameter is less than 1.33 mm. In various embodiments, the beacon 36 may pass position information from inside human body to an external system using either an electromagnetic method or a mechanical (e.g. acoustic) method. Provided below is a description of an ultrasound beacon and an electromagnetic beacon suitable for use as described herein.

An ultrasound beacon 36 may be made from piezo-ceramic material (e.g., one or more ultrasonic transducers). The ultrasound beacon 36 can either work in transmitter mode, in which the beacon 36 transmits an ultrasound wave when an RF electrical source is applied on its surface, or receiving mode, in which the beacon 36 generates an electrical RF signal when a mechanical wave hits its surface. An acoustic time of flight (ATOF) system may used to detect the beacon 36 position inside a human body (as described in more detail below with respect to block 204 of FIG. 5).

In one embodiment, the beacon 36 in the ATOF system can be a piezo-ceramic tube, which may have an outside diameter of about 1 mm and produces an ultrasound wave around 1.3 MHz when using a hoop vibration mode. The beacon's 36 position on the catheter may be designed to be at a known and repeatable spatial relationship relative to the targeting aid 34 (e.g., a specified distance from the edge of a targeting balloon, which can be positioned to touch the arteriotomy when inflated inside the artery).

Although an ultrasonic beacon system has been described, it will be appreciated that any beacon system that can be fit into the desired biological system (e.g., artery) may be used to detect the position of the beacon, and consequently, the position of the targeting aid (e.g., balloon). For example, an electromagnetic sensor, such as microbars (available from Ascension Technology Corporation, Burlington, Vt.), and a 3D space tracking system may achieve the same result as an ultrasonic beacon used in conjunction with ATOF methods.

Figure 9:
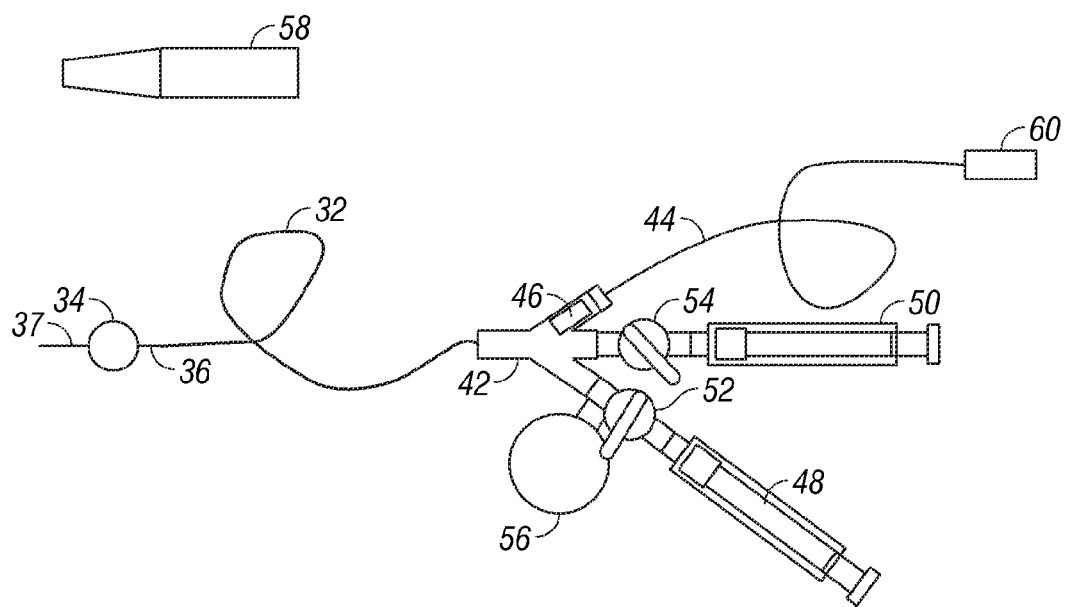
FIG. 9 is a diagram of the balloon targeting catheter and associated components.

FIG. 9 is a schematic depicting an overview of the components that may be directly associated with a balloon targeting catheter as described above. The catheter 32, balloon 34, floppy distal tip 37 and beacon 36 may be attached by way of a flexible body tube to a hub 42 that provides for interconnections to electrical drive and inflate/deflate functions.

The beacon 36 may be electrically coupled to a cable 44, which may be strain relief mounted into the hub 42. There is optionally an electrical matching component or network 46 inside the hub that transforms an impedance to improve electrical efficiency of the system and/or pulse shape transmitted by the beacon. Additionally there may be an electrical connector 60 on the terminus end of the cable.

Syringes 48 and 50 and their associated valves 52 and 54 may be used for fluid (e.g., sterile saline) injection and removal (e.g., to prime the balloon prior to use and to inflate and deflate the balloon after it has been inserted into the artery). Alternatively, a multi-port device designed for one-handed operation may be used. For example, fluid management devices that are spring loaded may be used, permitting release of the balloon fill by pushing one button.

The system may also include pressure gauge 56 to monitor or control the pressure or volume in the balloon. Those of skill in the art will recognize that pressure gauge 56 may be representative of any component (or various components) that achieves the effect of monitoring or controlling the pressure or volume in the balloon. It may also be advantageous to provide for a pressure regulation or release when the artery is fully compressed. This ability protects both the arterial wall and the balloon from compressive damage and can facilitate a more accurate location of the beacon 36 at the arteriotomy site throughout the compression sequence.

An insertion tool 58 may be provided to facilitate insertion of the distal tip 37 of the catheter 32 into an introducer sheath already inserted into a patient's artery. The insertion tool 58 may have a tapered distal tip suitable to be inserted into and to open the hemostatic valve on the introducer sheath (see FIG. 6) and has a constriction in its internal bore proximal to the location of the balloon that restricts bleeding through the device. This restriction may be designed to have a close fit to the diameter of the catheter body but still allow for free movement. In one embodiment, a close fit may be provided using a soft elastomeric material, thus providing a sealing function.

Figure 10A:
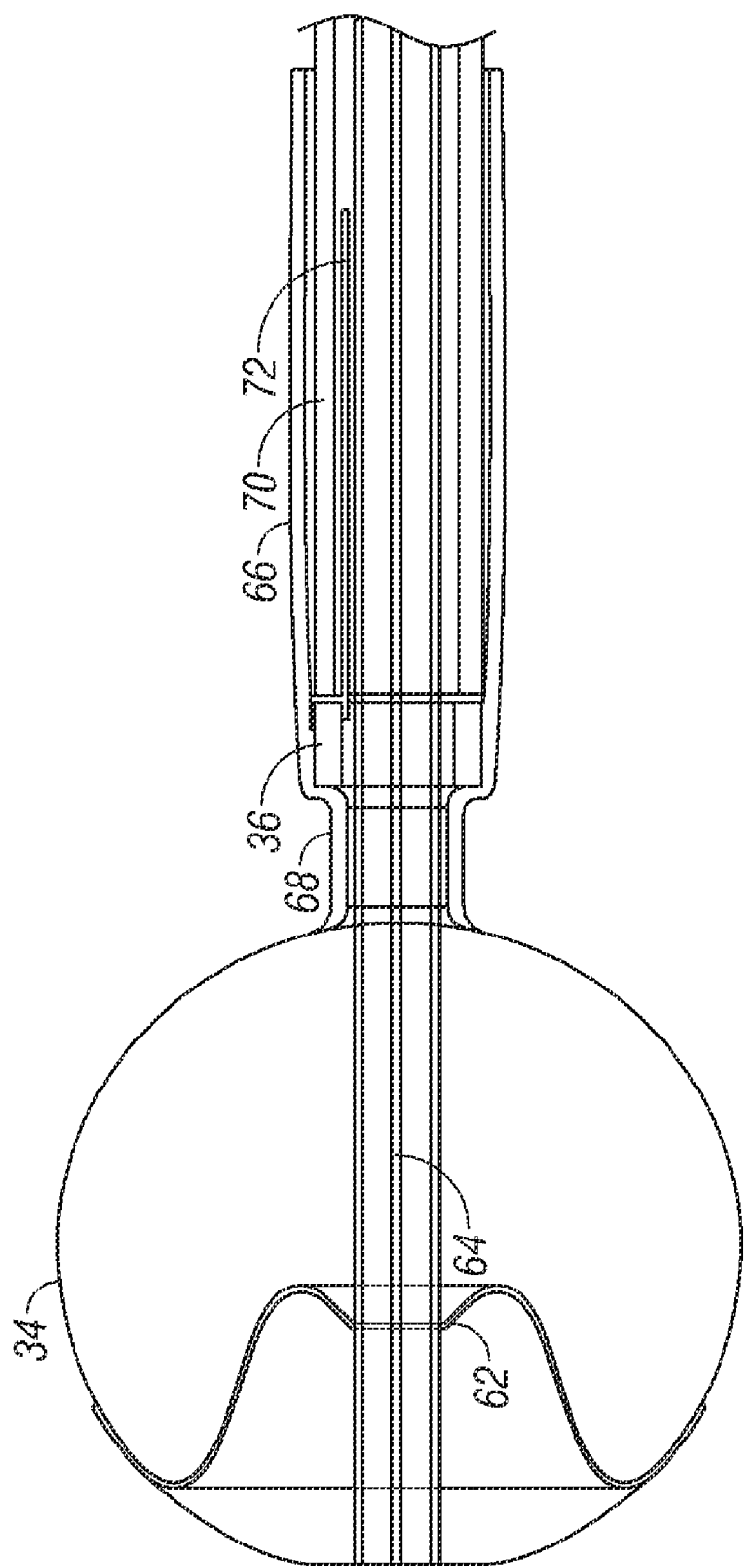
FIG. 10A is a longitudinal cross-sectional view of the distal section of a balloon targeting catheter.

FIGS. 10A, 10B, 10C, and 10D illustrate the design and construction of the distal section of one embodiment of a balloon targeting catheter in more detail. Referring to FIG. 10A, the catheter is substantially a coaxial design. Balloon 34 may be any suitable pliable material. In one embodiment, balloon 34 is made of soft, elastic polyurethane of a Durometer between 80 A and 65 D. The balloon 34 may be nominally between 3 and 7 mm in diameter. In some embodiments, the shape of the balloon 34 is not optimally spherical but rather a modified sphere foreshortened in its axial dimension in order to provide a large "footprint" against the artery wall but not to fully occlude blood flow in the artery. These shape variations may be accomplished using one of two methods, which may be used singly or in combination with one another. In one embodiment, the balloon may be foreshortened by locating the distal attach point 62 closer to the proximal attach point, thus "pooching" in the balloon. This "pooching" creates a non-spherical distal end for the balloon. Additionally, the neck of the balloon may be mounted to the core tube 64 in an inverted manner wherein the mounting point is effectively inside the balloon. The advantages of this inverted mounting technique include: i) allowing for a larger "footprint" against the artery wall and ii) mounting the balloon ends effectively inside the balloon allows the piezoelectric beacon to not have a layer of bonded balloon material located between it and the patient, thereby allowing for improved acoustic transmission properties.

Alternatively, the balloon 34 may be fabricated from stiff, essentially inelastic materials such as polyester or PET. These balloons hold an inflated shape more consistently than the polyurethane balloons and require/tolerate much higher inflation pressures. In some embodiments, unfold and refold characteristics may be tailored such that upon deployment, a smooth contact with the elements of the vessel is presented.

In some embodiments, the catheter may include a core tube 64. The core tube 64 may provide structural stiffness longitudinally, assuring integrity of the catheter assembly. In addition, the core tube 64 provides one or more internal lumens in which fluid can be transported to/from the balloon, and, with a diameter less than the overall body 66 diameter, provides a place where the deflated balloon may nest during insertion and removal. As depicted in the cross-sectional view of FIG. 10B, the core tube 64 may include two lumens (e.g., in a "double-D" configuration). One lumen may be used for fill and the other for venting, thus facilitating quick priming and removal of air bubbles. (Note that the holes in the core tube inside the balloon are not shown on of FIG. 10A through 10D.) The core tube is advantageously made of a higher Durometer (e.g. 55 D to 75 D) polyurethane that is compatible with being thermally bonded to other components in the catheter, most importantly the balloon 34.

Further describing the design, core tube 66 passes through the inside diameter of cylindrical beacon 36 and is terminated and interconnected at the hub 42 (see FIG. 9). It is advantageous to provide an enhanced flexibility of the catheter at that point immediately distal to the location of the beacon (and immediately proximal to the balloon) as depicted as section 68 on FIG. 10A. This location is also that of the thermal bond mounting the balloon to core tube 64. This flexibility permits the balloon to more flatly locate to and seal the arteriotomy even as the catheter is being pulled up at the angle of the entry channel (or track).

Proximal to the beacon 36, the core tube 66 may be positioned within a body tube 70, which may have an about 1 mm outside diameter and be made from polyurethane. Use of polyurethane promotes thermal bonding and melding with a jacket that covers beacon 36.

Figure 10B:
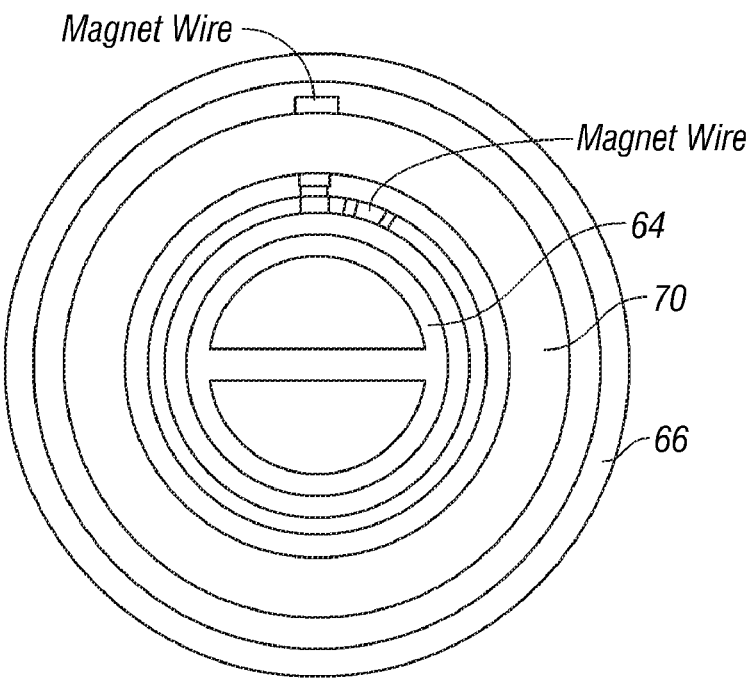
FIG. 10B is an axial cross-sectional view of the distal section of a balloon targeting catheter.
Figure 10C:
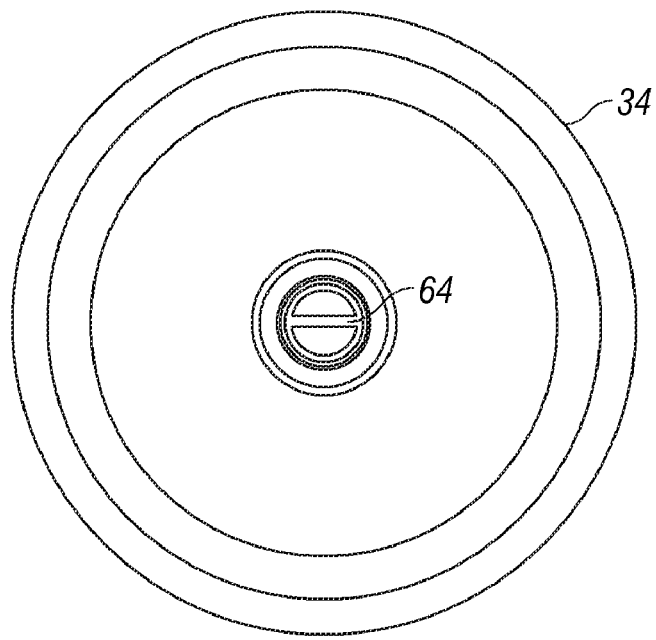
FIG. 10C an end view of the distal section of a balloon targeting catheter.
Figure 10D:
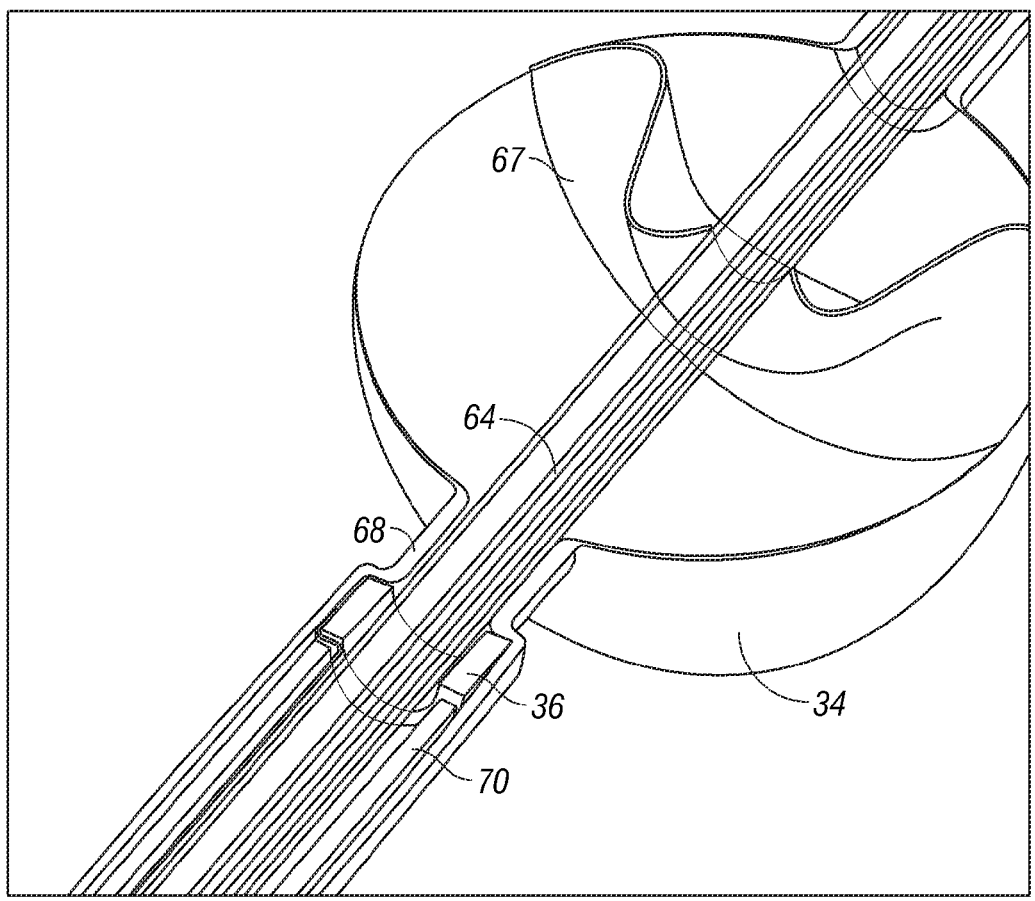
FIG. 10D is a longitudinal cross-sectional view of the distal section of a balloon targeting catheter.

FIG. 10B is a rendering of the distal cross-section of a balloon targeting catheter from a view proximal to the beacon location. This view also depicts the location of wires extending through the catheter to the beacon 36. FIG. 10C depicts an end view of the distal end of the balloon targeting catheter showing the core tube 64 in cross-section. FIG. 10D depicts a cross-sectional view longitudinally through the distal portion of the balloon targeting catheter.

Figure 7B:
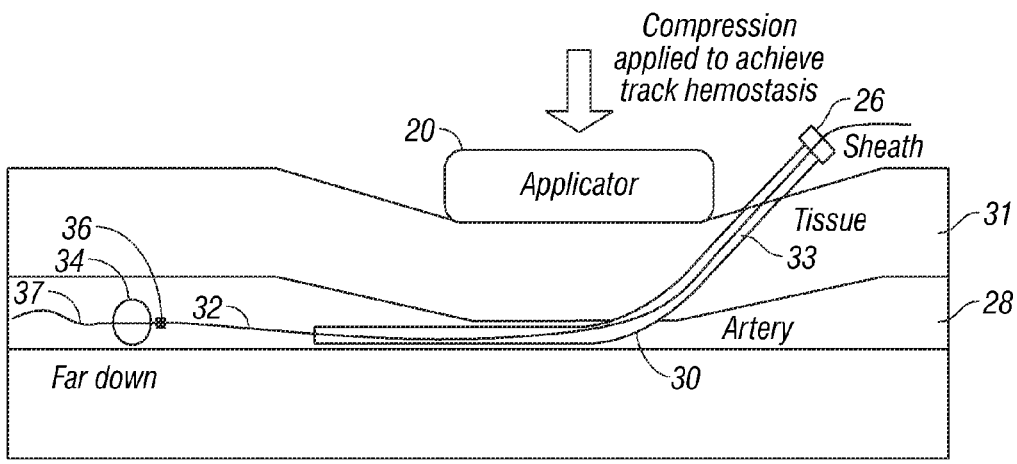
FIG. 7B is a diagram of a vascular closure procedure illustrating the inflation of a targeting balloon and compression from a therapeutic applicator.

Returning to the discussion of the flow chart in FIG. 5, at block 102, after insertion of the targeting catheter, the balloon 34 is inflated once its position is known to be past the arteriotomy 30. FIG. 7B depicts the inflation of the balloon 34 within the artery 28 beyond the distal opening of the introducer sheath 30. The balloon 34 may be inflated with any suitable fluid such as a liquid (e.g. a sterile saline solution). The user next (or simultaneously) applies compression with the applicator 20 to stop blood flow in the tract 33 through the tissue 31 that is formed by the introducer sheath 26.

Figure 7C:
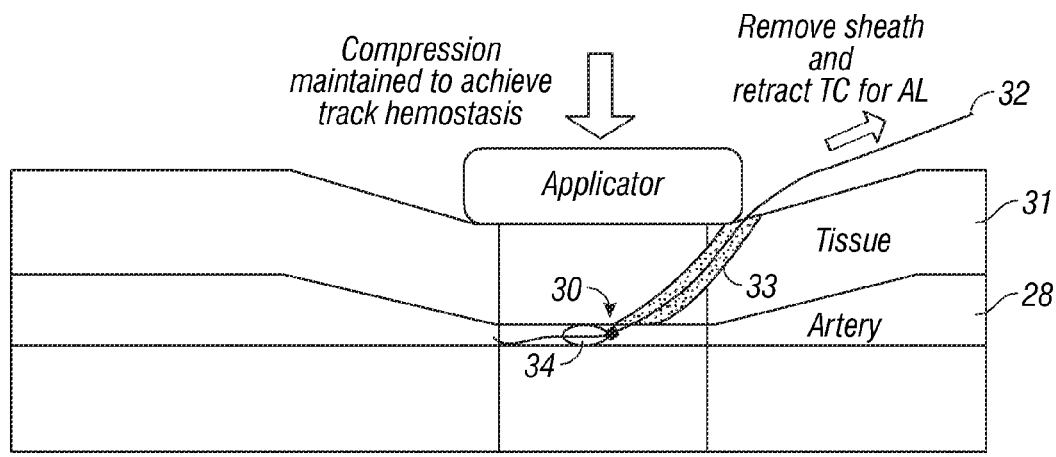
FIG. 7C is a diagram of a vascular closure procedure illustrating arteriotomy localization.

At block 104 in FIG. 5, the introducer sheath 26 and targeting catheter 32 are retracted from the artery 28 as a unit until the balloon 34 comes into contact with the vessel wall at the arteriotomy site 30 (FIG. 7C). In this position, egress of blood from the artery through the tract 33 is impeded by the balloon 34 and the arteriotomy locator beacon 36 is situated within the arteriotomy. Thus, by retracting the balloon until it contacts the artery 28 wall, the arteriotomy site 30 is localized.

Figure 7D:
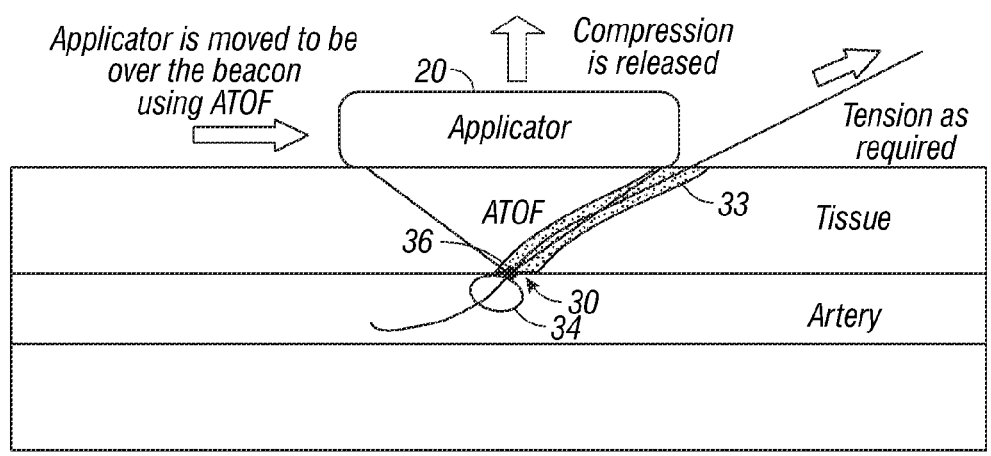
FIG. 7D is a diagram of a vascular closure procedure illustrating alignment of a therapeutic applicator to the arteriotomy.

Next, at block 106 of FIG. 5, the pressure applied to the applicator 20 may be released so as to allow for easier alignment of the applicator 20 relative to the arteriotomy 30 as illustrated in FIG. 7D. The targeting aid balloon 34 will serve to stop blood flow up the track 33 during this process. A cluster of receivers in the applicator may be used to detect ultrasonic pulses transmitted from the arteriotomy locator beacon 36 and targeting algorithms resident in the generator may continuously analyze these signals and produce graphical feedback on the applicator 20 display (e.g., utilizing acoustic time of flight (ATOF) algorithms). Using this intuitive information, the user is enabled to quickly and accurately target the focused ultrasound at the arteriotomy site 30.

As noted, acoustic Time-of-Flight (ATOF) may be utilized to determine the position of the beacon 36 relative to the therapeutic applicator 20. In some alternative embodiments, a separate beacon is not included on the targeting catheter (for example, where the arteriotomy targeting aid is capable of ultrasound generation, such as when it is a Doppler beacon or a resistance heated PZT). In such embodiments, the targeting aid in effect also serves as the acoustic beacon. Accordingly, the ATOF methods described herein can also be used in these alternative embodiments.

The PZT element (either in beacon 36 or as part of the targeting aid 34) may be utilized as a highly localized sound source marker, easily visible in an ultrasound image or detected and localized in an Acoustic Time of Flight detection system. In one ATOF approach, the beacon transmits tone bursts of sound to receivers encircling the outer perimeter of the therapeutic applicator. The in-situ beacon is pulsed while each of the receivers independently measures the time for the pulse to arrive. When the time of flight to each receiver is known and the time has been converted to a distance between the beacon and the receiver, then the position of the beacon relative to the receivers can be calculated using triangulation. A minimum of three receivers may be used to calculate the X, Y and Z position of the beacon relative to the Therapeutic Applicator. If more than three sensors are used, the accuracy of the position calculation can be improved.

By continuously monitoring the position of the arteriotomy relative to the therapeutic applicator via ATOF, the user can adjust the position and orientation of the applicator such that the therapeutic energy source focus (e.g., laser, RF, ultrasound, or microwave) is located at the arteriotomy. In some embodiments, the user interface may provide a display to assist the user in appropriately adjusting the position and orientation of the applicator. The display may include graphical elements such as cross hairs or target circles as well as ultrasound images of the focal region. Those of skill in the art will appreciate many possibilities for providing feedback to a user to assist in aligning a therapeutic energy source with the arteriotomy locating sensor on the Targeting Catheter.

Figure 11:
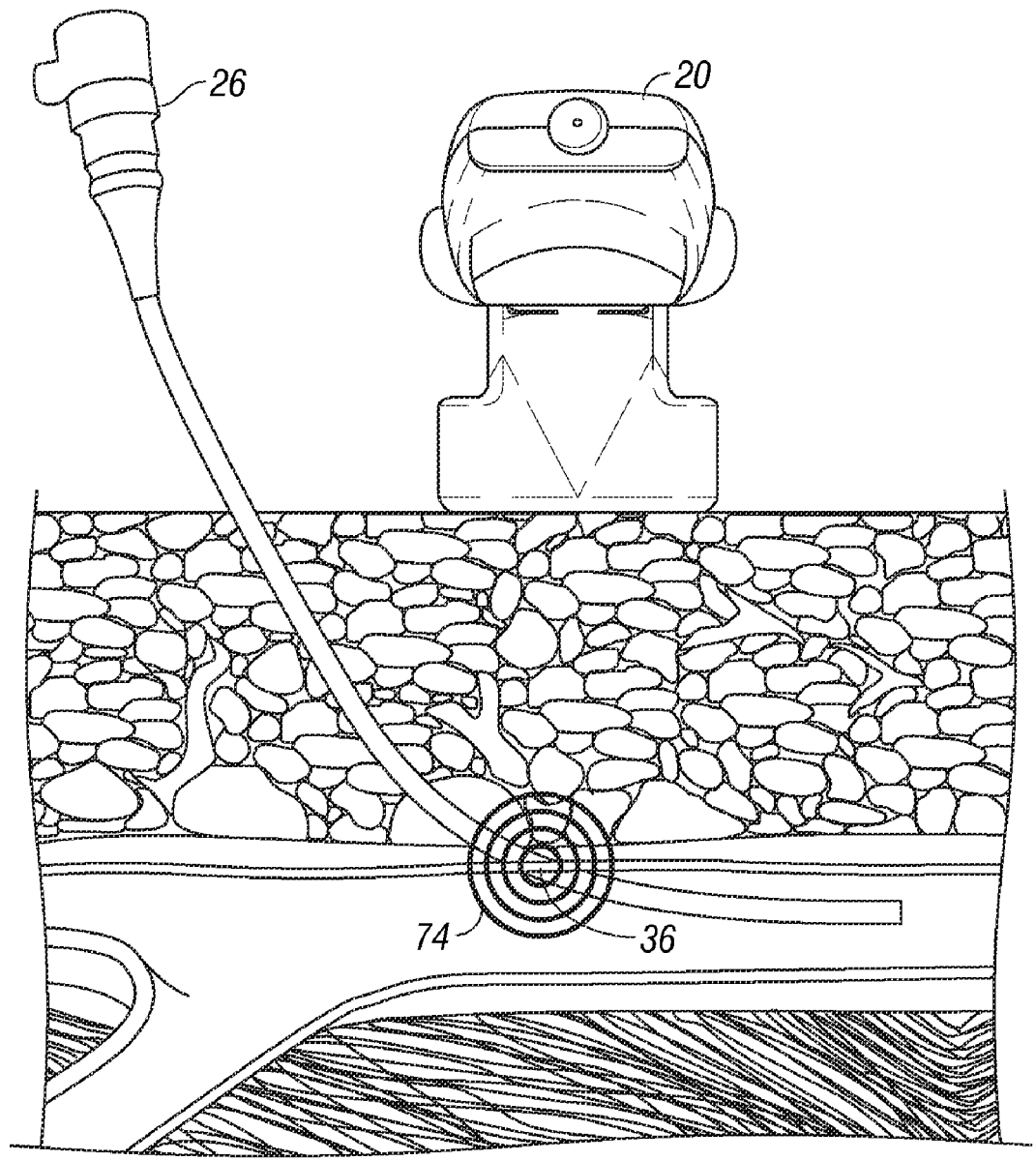
FIG. 11 is a diagram illustrating the targeting catheter and ultrasound applicator after arterial localization with the arteriotomy locating beacon emitting ultrasound waves.
Figure 12:
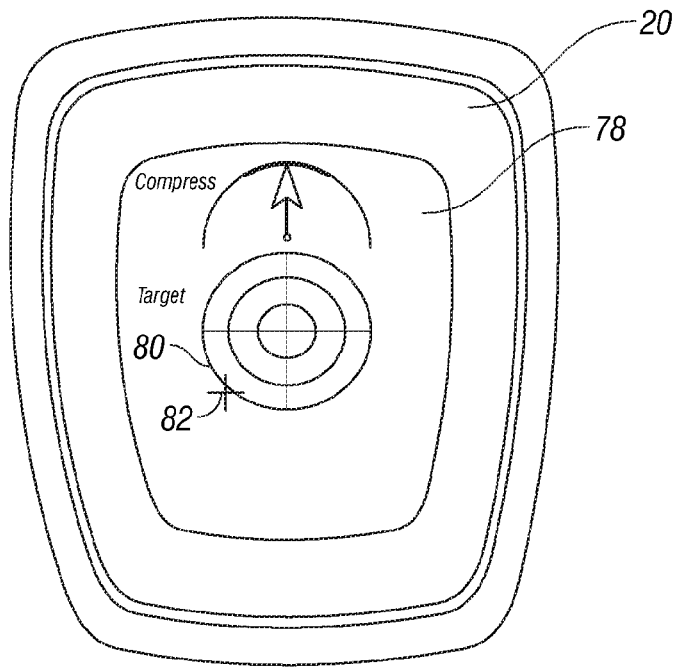
FIG. 12 is an illustration of the user interface for targeting on the arteriotomy.

FIG. 11 illustrates the applicator 20 positioned over the arteriotomy with the targeting catheter positioned such that the arteriotomy locating beacon 36 are positioned at the centroid of the arteriotomy. Waves 74 depicted in the illustration represent acoustic energy from the beacon 36 in which the ATOF measurement is performed via acoustic sensors on the therapeutic array located on the applicator 20. FIG. 12 illustrates one embodiment of a user interface 78 for targeting on the arteriotomy. The circle/bullseye 80 represents the position of the focal point of the therapeutic applicator and the cross hair 82 represents the location of the arteriometry locating sensor as determined by ATOF. The user may be instructed to align the bullseye on top of the crosshairs thereby insuring that the arteriotomy is within the focus of the therapeutic applicator.

Target localization based on acoustic time of flight (ATOF) can provide accurate and robust position sensing of target location relative to the therapeutic ultrasound transducer. Direct X, Y and Z (i.e. three-dimensional) coordinate locations of the target can be provided without the need for image interpretation. Three-dimensional targeting information facilitates the use of an explicit user interface to guide operator actions. ATOF is less sensitive to variations in patient anatomy as compared to imaging techniques. ATOF can be accomplished with a relatively simple and inexpensive system compared to the complex imaging systems used by alternate techniques. In some embodiments, continuous tracking of the target in the presence of movement between the target and the external transducer may be provided. In some embodiments, ATOF allows use of system architectures that utilize a larger fraction of the patient contact area to generate therapeutic power (as contrasted with imaging based alternatives)—thus reducing the power density applied to the patient's skin.

Figure 13:
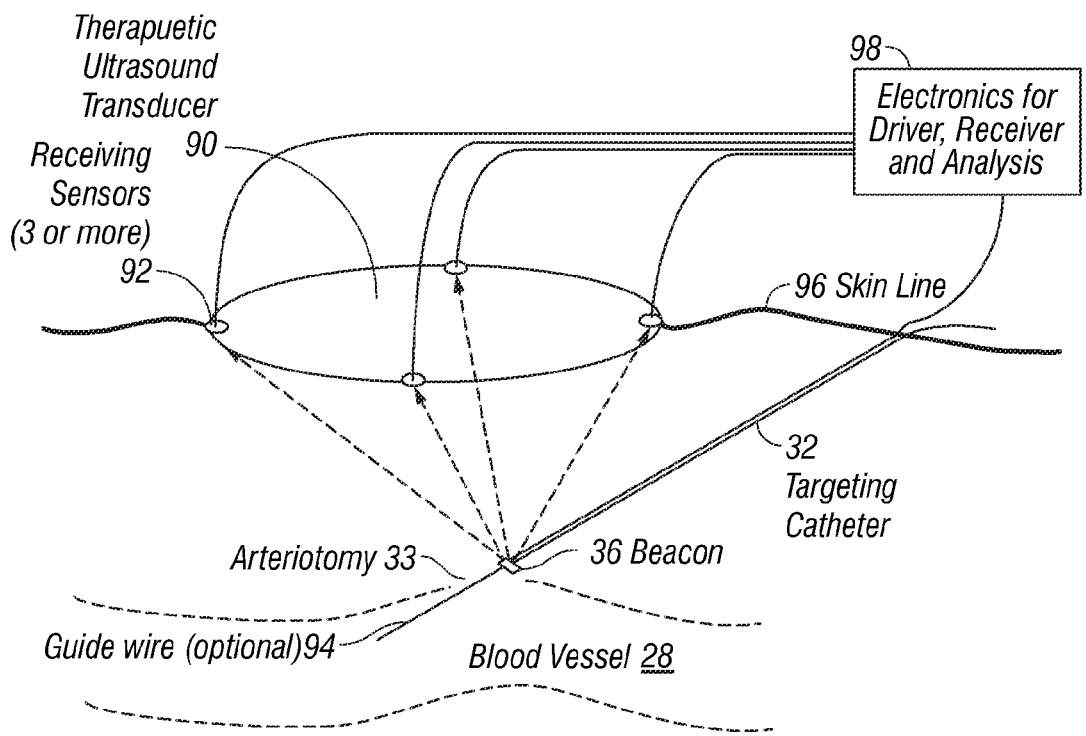
FIG. 13 is a schematic illustrating acoustic time of flight targeting of the therapeutic applicator.

FIG. 13 illustrates one embodiment of an ATOF system that includes a beacon 36 having a small ultrasonic transmitter 36 such as described above placed at or near the arteriotomy site 33 (e.g., through use of a targeting catheter). An array of ultrasound receiver sensors 92 generally encircling the outer diameter of the ultrasound therapeutic transducer 90 is located on the applicator. The in-situ transducer (beacon) 36 is pulsed while simultaneously the receivers 92 begin to listen for the ultrasound pulses to arrive. Each of the receivers 92 independently measures the time for the pulse to reach their location. The time of flight from the receiver 92 to the beacon 36 can be determined and the location of the beacon 36 can be calculated by using a variety of triangulation techniques familiar to those skilled in the art of sonomicrometry and/or global positioning systems (GPS). The historical basis for this approach is partially documented in U.S. Pat. No. 4,154,114 to Katz and in U.S. Pat. No. 4,100,916 to King. Veseley, in U.S. Pat. No. 6,019,725, provides a good description of 3D tracking. All of these patents are incorporated herein by reference in their entirety.

It should be recognized that while embodiments will be described wherein the beacon 36, as described above, transmits and the receivers 92 receive, the transmit and receive functions may be reversed or used in configurations wherein various or all sensors both transmit and receive.

It should also be recognized that it may be advantageous to provide for higher accuracy of position determination at and in the vicinity of the therapeutic target, while permitting lower resolution in locations off target. Such lower resolution may be adequate for providing navigation (positioning of the therapy transducer on the patient) guidance to the operator.

The transmitting beacon 36 may be "pinged" with a short burst of approximately 3 cycles. The frequency of the ultrasound burst requires a tradeoff between location sensitivity, signal attenuation, and dispersion angle. Higher frequencies help to improve the accuracy of the location data. At lower frequencies the signal may encounter less attenuation on its path to the receivers 92, which will generally produce a better signal to noise ratio. Also at lower frequencies, the transmitter will tend to distribute its energy over a wider angle for given transducer dimensions, which will allow the beam to spread out over a wider area to better reach the receivers 92 from a variety of locations in the targeting space. For an arteriotomy locator, in one embodiment, a frequency in the range of about 500 KHz to about 1 MHz is used, providing good resolution, low attenuation, and compatibility with isotropic transducers that can be inexpensively fabricated.

As noted above, the receiving sensors 92 may be placed in an array, or constellation, around the therapeutic transducer 90. A minimum of three elements may be used to allow the position of the beacon 36 to be calculated in 3 dimensions. Additional sensors can be used to improve the accuracy, robustness and sensitivity of the calculation. The analog signal from the receivers may be, after pre-amplification, converted to digital format for accurate signal processing. The rate at which the signal is digitized may influence the maximum accuracy, or precision, of the time of flight calculation. The precision is determined by the speed of sound in human tissue, which is approximately 1540 meters/second, and the rate at which digital samples are collected as follows.

$$\text{Distance\_per\_sample(m)} = \text{speed\_of\_sound(m/s)} / \text{samples\_per\_second(1/s)} \quad \text{Eq. A}$$

For example, if the signal is digitized at 32 million samples per second, the precision of the measurement due to sampling will be 1540/32,000,000=0.048 millimeters.

The timing of the transmit pulse and the collection of data from the receivers 92 may be synchronized by controller electronics so that the time of flight can be measured. The receivers 92 can start counting samples at the same time the transmit burst begins. Each channel will then continue to count until it detects the arrival of the short ultrasound burst. Although the burst may be many digital samples in length, a specific sample within the received burst can be chosen as the "official" arrival time in order to achieve maximum accuracy.

There are several possible algorithms that the receivers 92 can employ to determine when they have detected the arrival of the ultrasound pulse. For example, detection of the peak amplitude of the received signal, correlation with the expected pulse shape, or first crossing of an amplitude above the noise floor could all produce a specific sample number that would be used as the detection point for arrival of the burst. While the sampling rate of the received signal may determine the precision of the measurement, the detection algorithm can influence the measurement's accuracy.

The size of the volume in which the beacon 36 can be detected will determine several design parameters of the system. For example, if the detection volume is a cylinder whose circular diameter is equal to the diameter of the ring of receivers 92 around the transducer 90 (a representative case for vascular sealing) and whose depth is the maximum depth of the arteriotomy then several parameters can be known. These dimensions define the maximum time over which the receiver's TOF detectors 92 must operate. This volume, along with the attenuation of the ultrasound signal in tissue at the chosen frequency will also determine the power required from the beacon and the sensitivity required from the receivers 92. For example, if the diameter of the ring of receivers 92 is 45 mm and the maximum depth required is 50 mm then the maximum distance from the beacon 36 to the farthest receiver will be:

$$\text{Sqrt}(45^2+50^2)=67.25\text{mm} \quad \text{Eq. B}$$

The maximum time of flight will be:

$$0.06725\text{m}/1540\text{m/s}=43.67 \text{ microseconds}$$

When the time of flight to each receiver 92 is known and the time has been converted to a distance between the beacon 36 and the receiver 92, then the position of the beacon 36 relative to the receivers 92 can be calculated. A minimum of three receivers 92 can be used to calculate the X, Y and Z position of the beacon 36. If more than three sensors are available the accuracy of the position calculation can be improved in a number of ways. For example, if four sensors are available then the position can be calculated four times with different combinations of three sensors and the results could be averaged. Or, if more than three sensors are available, extra weight could be given to those with the best signal as determined by received amplitude or sharpness of the correlation result. These techniques are explained in more detail below.

To calculate the position of the beacon 36, a three dimensional coordinate system is defined within the space where the beacon 36 may lie relative to the receivers. In the application with the therapeutic transducer 90, the ring of receivers 92 would conveniently lie in the X,Y plane at the zero crossing of the Z axis (planar constellation of receivers 92). The Z axis extends into the body, perpendicular to the face of the transducer 90 and passes through the center of therapy. The coordinates of the beacon 36 can be calculated by solving a system of three equations with three unknowns. Let $x_i$, $y_i$ and $z_i$ be the coordinates of the receivers 92 in the three dimensional coordinate space where i=1 through 3. Let $d_i$ equal the distance from the receiver 92 to the beacon 36 based on the time of flight measurements. Let $X_b$, $Y_b$ and $Z_b$ be the coordinates of the beacon 36. Then, $$(X_b-x_i)^2+(Y_b-y_i)^2+(Z_b-z_i)^2=d_i^2 \text{ (for } i=1 \text{ through 3)} \qquad \text{Eq. C}$$

There are a number of ways to solve eq. C well know to those skill in the art. These methods are discussed in greater detail below. Solutions that are computationally efficient are preferred, potentially allowing higher rates of position determinations and/or more computational time for other system functions.

In some embodiments, sensors, or transducers, for ATOF systems function with wide, and to the extent possible, uniform angular sensitivity so that pulses may be effectively sent and received to and from a variety of locations in the targeting space. In vascular sealing, where the transmitting beacon is mounted on a targeting aid positioned in the entry channel, a range of angular orientations with respect to the receiver constellation results from the fact that entry channels are inclined at various angles to the skin surface. These angles are typically between 30 and 70 degrees.

For such isotropy, transducers generally can be small with respect to the dimensions of their acoustic wavelength (e.g., less than one-half wavelength). Transducers are also preferably dimensionally small so that the phase difference (or time delay) across the sensor is small; a large phase difference will distort an accurate time measurement.

Transducer Materials: Materials for ATOF receivers and transmitters may generally be any of the materials used in diagnostic imaging. Because either transmit (here in the case of beacons on the targeting aid) or receive (in the case of the constellation of sensors) is, in many of the embodiments described here, the only function required, material selection may be optimized for specific transmit or receive characteristics.

Materials with various desirable characteristics may include but are not limited to:

PZT (lead-zirconate-titanate), readily, economically available in may forms. Efficient in both transmit and receive.
PMN (lead-meta-niobate) similar to PZT
PVDF and copolymer film piezo-materials are inexpensive and can be formed in very small shapes; these are sensitive receivers. When used as a beacon, they can include sufficient insulation and isolation to shield patients from the high voltages used.
MEMS transducers (PMUTs and CMUTs) can be attractive because of their wide bandwidth, and potentially low cost.
Barium titanate and other suitable materials.

Figure 14:
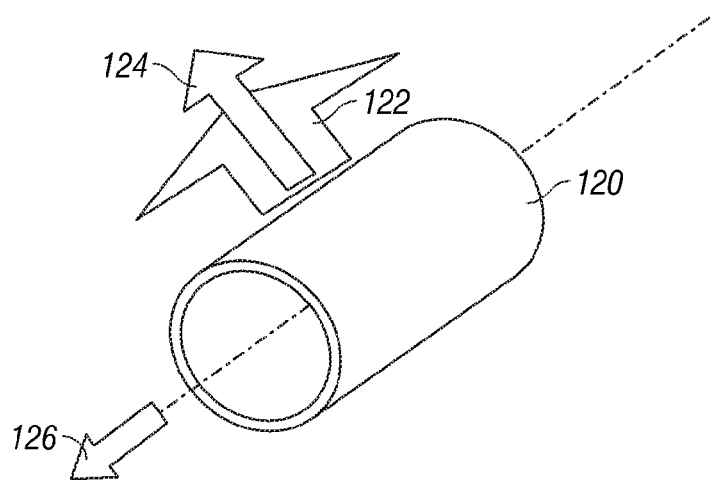
FIG. 14 is a schematic of a cylindrical piezoelectric arteriotomy locating beacon having three possible modes of operation.

Transducer Shapes: A variety of transducer shapes may be used. Optimum configurations differ generally depending upon whether the transducer is mounted on the targeting catheter or those mounted on the applicator, viz the constellation. For the targeting catheter beacon, cylindrical piezoceramic elements may be used and offer a number of advantages. FIG. 14 depicts use of a cylindrical element having multi-mode characteristics. A hollow cylindrical transducer 120 has electrodes inside and outside, thus applying a field across the thickness of the cylinder's wall. Several vibrational modes may be selectively driven by selection of drive frequency. Lateral (or radial) mode 122 is the hoop mode; lateral mode 124 is the wall thickness mode; and length mode 126 radiates forward as shown. Frequencies and uses of modes are listed below for example purposes and are not intended to be limited to:

a) Hoop Mode (0.75 MHz):
ATOF: Beacon Position Tracking, Station Keeping
T/R Doppler: Arteriotomy Position Locating
b) Wall Thickness Mode (8.5 MHz) (Side View)
PW Doppler: Arteriotomy Position Locating
T/R Doppler: Arteriotomy Position Locating
c) Length Mode: (4.0 MHz)
PW Doppler: Arteriotomy Position Locating, Station Keeping Cylindrical transducers may also advantageously be used in multiples, where for example, two transducers are mounted on the distal end of a targeting aid to make up the beacon. More information regarding use of two-transducer configurations may be found in U.S. Pat. Nos. 5,515,853; 4,407,294; and 4,697,595, all of which are incorporated herein by reference in their entirety.

Spherical or partial-sphere shaped transducers also have advantages of excellent isotropy for beacon/TA applications. These transducers also present smooth, rounded surfaces compatible with insertion into the body. Alternatively, greater isotropy may be realized by operating the transducers at multiple frequencies where the nulls of the radiation pattern at one frequency are complimented by non-null sensitivity at another frequency.

Figure 15:
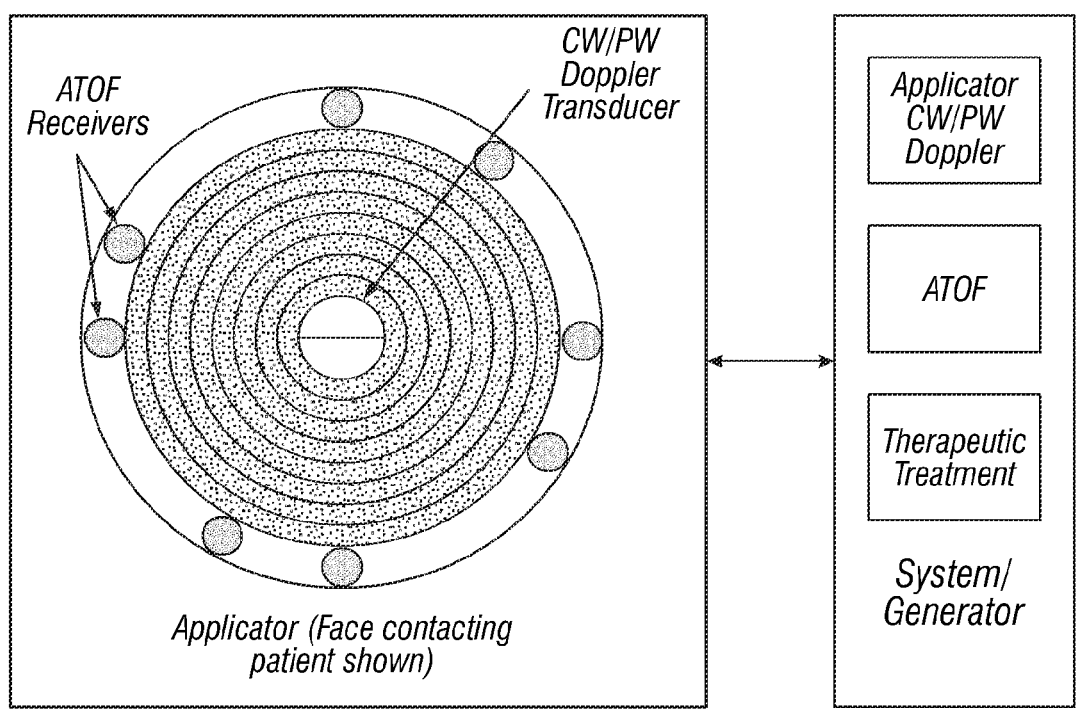
FIG. 15 is a schematic of a therapeutic applicator face having CW/PW Doppler mode transducers, ATOF receivers, and therapeutic transducers.

For transducers used in the applicator mounted constellation and operated as receivers, planar structures may provide fabrication advantages and provide a substantially flat surface that readily couples to the patient's skin surface. It is noted that, for vascular sealing applications where the axis of therapy is approximately centered in the targeting space, high resolution of spatial localization of the targeting catheter is only needed in the vicinity of the center. Away from the center only rough estimates of targeting catheter are needed in order to provide the operator directional movement information. FIG. 15 depicts one embodiment of an applicator face having ATOF transducers located around the periphery, therapeutic transducers located in concentric circles, and a CW/PW Doppler transducer located at the center.

ATOF Distance/Position Computation

Problem: Find the (X, Y, Z) coordinates of a transmitter given the spatial coordinates of N receivers (e.g., N=8) and the distance measurements from each one. Let Xi, Yi, Zi be the receiver coordinates and Di the measured distances, where i=1 . . . N. In the case of a planar applicator face (see FIG. 15), all Zi are equal, since the receivers are coplanar. Let $Z_i=Z_0$ for all i.

Solution based on three receivers: A solution for (X, Y, Z) can be found using any three receivers, denoted here as 1, 2 and 3. The receivers are coplanar and arranged in a ring with 45 degree angles between them. The receiver closest to the projection of the transmitter onto the receivers plane can be denoted as receiver (1). The other two (2, 3) are the farthest from the projection, i.e. in an angle of 135 degrees from (1) in both directions. Receiver (1) may have the strongest signal.

The coordinates of the three receivers are: $(X_1, Y_1, Z_0)$, $(X_2, Y_2, Z_0)$ and $(X_3, Y_3, Z_0)$, respectively. The corresponding distance measurements are $D_1$, $D_2$ and $D_3$. Assuming no error in the measurements, the following three equations can be solved for (X, Y, Z):

$$(X-X_1)^2+(Y-Y_1)^2+(Z-Z_0)^2=D_1^2$$

$$(X-X_2)^2+(Y-Y_2)^2+(Z-Z_0)^2=D_2^2$$

$$(X-X_3)^2+(Y-Y_3)^2+(Z-Z_0)^2=D_3^2 \quad (1)$$

These three quadratic equations reduce to two linear equations with unknowns (X, Y) if the first equation is subtracted from the second and the second from the third. The resulting equations are:

$$2(X_2-X_1)X+2(Y_2-Y_1)=b_1$$

$$2(X_3-X_1)X+2(Y_3-Y_1)=b_2 \quad (2)$$

where, $$b_1=D_1^2-D_2^2+X_2^2+Y_2^2-X_1^2-Y_1^2$$

$$b_2=D_2^2-D_3^2+X_3^2+Y_3^2-X_2^2-Y_2^2$$

These two equations can easily be solved for (X, Y). Z can then be found from any of the original three equations (a quadratic equation with one unknown).

Solution based on N receivers: The solution for N receivers involves an iterative minimization process of an objective function that is based on the sum of square errors from the receivers and can be formulated as follows:

$$J(X,Y,Z)=\Sigma(Di-Li)^2$$

where $\Sigma$ is over all receivers $i=1 \ldots N$, $Di$ is the measured distance from the transmitter to the $i^{th}$ receiver, and:

$$Li=\sqrt{(X-X_i)^2+(Y-Y_i)^2+(Z-Z_i)^2}$$

is the Euclidian distance from the transmitter location (X, Y, Z) to be found to the $i^{th}$ receiver. Note that no assumptions are made on the coplanarity of the receivers (i.e. the Z, are not necessarily equal).

Partially differentiating J(X, Y, Z) with respect to X, Y, Z gives the following three equations:

$$\partial J/\partial X=\Sigma 2(Di-Li)(Xi-X)/Li$$

$$\partial J/\partial Y=\Sigma 2(Di-Li)(Yi-Y)/Li$$

$$\partial J/\partial Z=\Sigma 2(Di-Li)(Zi-Z)/Li \quad (3)$$

Equating each of these equations to zero, yields:

$$X=\Sigma[Xi+Di(X-Xi)/Li]/N$$

$$Y=\Sigma[Yi+Di(Y-Yi)/Li]/N$$

$$Z=\Sigma[Zi+Di(Z-Zi)/Li]/N$$

The expressions (X−Xi)/Li, (Y−Yi)/Li and (Z−Zi)/Li are the cosine of the angles between the transmitter and $i^{th}$ receiver and its projection into the Y-Z, X-Z and Y-Z planes respectively. Therefore, the above equations can be written as:

$$X=\Sigma[Xi+Di\,Cos(\theta_{YZ})]/N$$

$$Y=\Sigma[Yi+Di\,Cos(\theta_{XZ})]/N$$

$$Z=\Sigma[Zi+Di\,Cos(\theta_{YZ})]/N \quad (4)$$

The angles depend on the transmitter location (X, Y, Z). However, to a good approximation, it can be assumed that these angles will not vary by much between iterations. Therefore the angles from the $(k-1)^{th}$ iteration can be used in the $k^{th}$ iteration.

The algorithm can be stated as follows:
1. Choose initial conditions for the transmitter location (X, Y, Z). This can be done using any three receivers, for example as shown in Part 1.
2. Calculate initial Li, $i=1 \ldots N$ and the initial objective function J(X, Y, Z).
3. Repeat K times with iteration counter $k=1 \ldots K$:
   a. Calculate Li, $i=1 \ldots N$ and the objective function J(X, Y, Z)
   b. If the absolute value of the difference between J in the $(k-1)^{th}$ iteration and the $k^{th}$ (current) iteration is less than $\epsilon$, stop.
   c. Calculate the cosine angles $Cos(\theta_{YZ})$, $Cos(\theta_{XZ})$ and $Cos(\theta_{YZ})$ based on the last iteration.
   d. Update the transmitter location (X, Y, Z) based on equations (4).
4. End iteration loop.

Returning to the discussion of the flow chart in FIG. 5, at block 108, after aligning the applicator using the beacon, the user may apply additional hemostatic compression with the applicator so as to transiently either partially or fully occlude the artery. By temporarily reducing or completely stopping blood flow, less energy required to be delivered at the arteriotomy to perform thermal hemostasis, since vessel blood flow serves to dissipate focused delivery of energy. During compression, care may be taken to maintain accurate targeting.

Figure 7E:
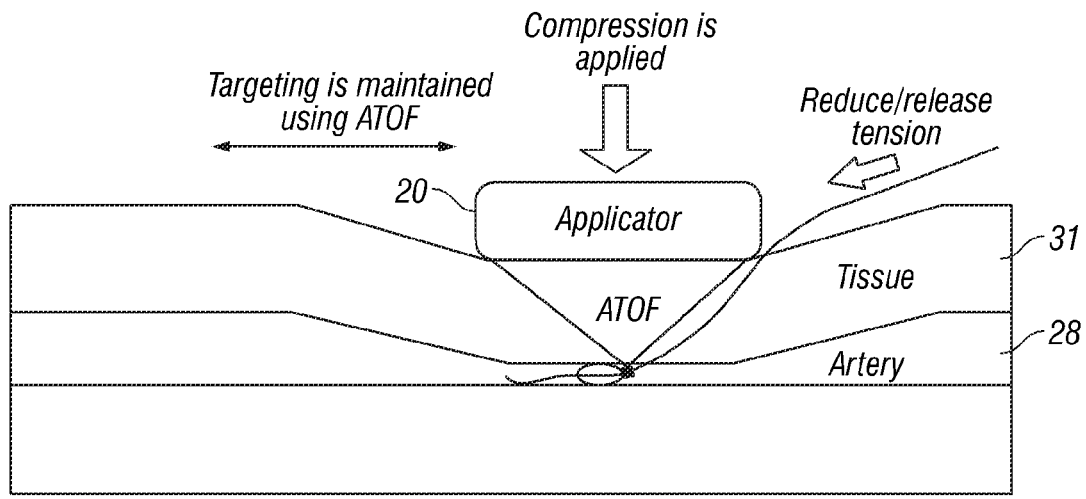
FIG. 7E is a diagram of a vascular closure procedure illustrating compression applied to either partially occlude or fully occlude the artery prior to focused energy treatment.

The use of additional transducers and sensors may be used to aid in compression measurement feedback to the user. An example of such transducers and sensors may include a Doppler transducer and a force sensor, each located in the applicator, to continuously interrogate the vascular blood flow and the applied compressive force, respectively. A compression algorithm resident in the generator may be used to analyze signals from the sensors and produce graphical feedback on the applicator display to enable the user to apply and maintain adequate compression of the arteriotomy (see compression indicator in FIG. 12). Alternatively or in addition to these sensors, a sensor capable of monitoring blood flow and artery pressure properties may be located on the targeting catheter. Non-limiting examples of such a sensor include Doppler ultrasound sensors, an optical fiber sensor, thermal sensors, or other pressure/flow sensors used to monitor blood flow characteristics. Pressure sensors attached to the therapeutic transducer can be calibrated with respect to the blood flow sensors located in the artery on the targeting catheter. Upon removal of the targeting catheter, the pressure sensors located on the therapeutic applicator can be used to determine the status of the vessel (e.g. unobstructed, partially occluded, or fully occluded). Additionally, external blood flow/pressure sensors may also be used such as traditional manual stethoscope in combination with the application of pressure FIG. 7E illustrates the applicator 20 applying force against the tissue 31 causing the vessel 28 to transiently be either partially or fully occluded. The reasons for applying pressure are to stop the bleeding occurring at the wall puncture site prior to (as described above) and during the application therapeutic energy dose. Additionally, by reducing or eliminating blood flow through the vessel 28, efficient delivery of thermal energy to cause hemostasis is promoted, since vessel blood flow serves to dissipate the delivered thermal energy.

It is has been discovered that one can improve the efficiency of thermal energy vascular closure by administering the thermal energy (e.g. high intensity focused ultrasound) under conditions whereby all tissue blood flow related convective cooling can be eliminated; specifically bleeding which occurs in the introducer track and from the arterial (luminal) blood flow. Accordingly, one embodiment involves applying the therapeutic applicator with pressure of sufficient magnitude to cause the artery to be temporarily occluded during the dose (power-on) period of the thermal energy and perhaps continuing for a short period during all, or a portion of, the post-dose compression period. This treatment condition is termed "transient arterial occlusion" (TAO).

Figure 50:
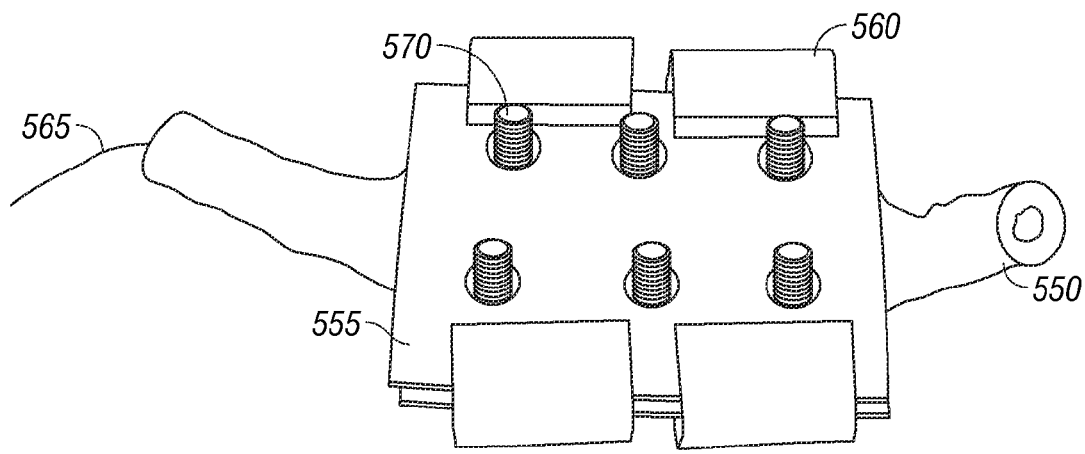
FIG. 50 is a schematic of an experimental setup for measuring the effects of transient arterial occlusion.
Figure 51:
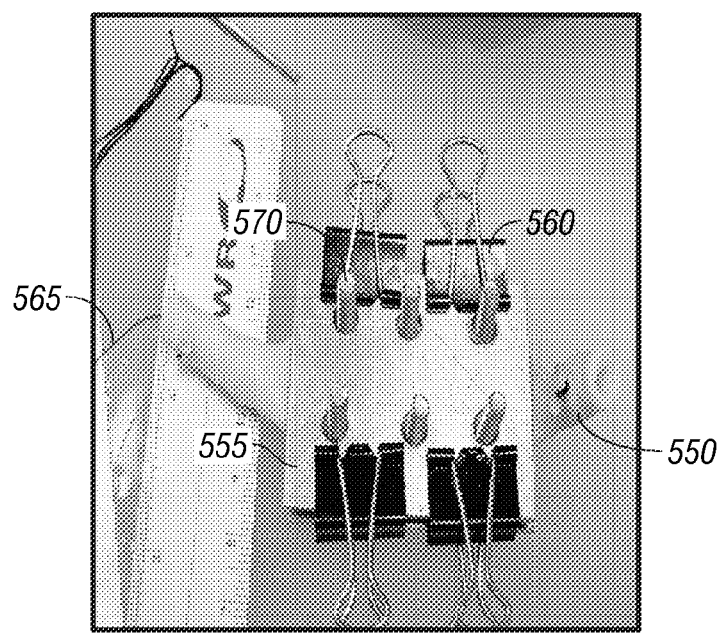
FIG. 51 is a photograph of the setup depicted in FIG. 50.

The following experiments were undertaken in order to demonstrate that the delivery of thermal dose in combination with TAO surprisingly did not adversely cause the lumen to be permanently occluded (e.g. the interior walls of the artery to be welded shut). FIG. 50 illustrates a testing device used to evaluate if thermal energy in combination with TAO causes the intimal walls of the artery to weld together. FIG. 50 illustrates bovine carotid 550 with a needle puncture arteriotomy pressed between two aluminum plates 555. The plates are compressed together using spring clamps 560 and aligned with alignment pins 570. Compression force was measured at 25 lbs. A thermocouple 565 was located within the transiently occluded bovine artery. This test apparatus was then fully submerged in boiling saline for 1 minute. The temperature and time were chosen to exceed the temperature and equal the time exposure that occurs during one embodiment of delivering high intensity focused ultrasound for arterial hemostasis (e.g., 70° C. and 40 seconds, respectively). FIG. 51 is a photograph of the bovine carotid sandwiched between the two aluminum plates after a 60 second submersion in boiling saline.

Figure 52:
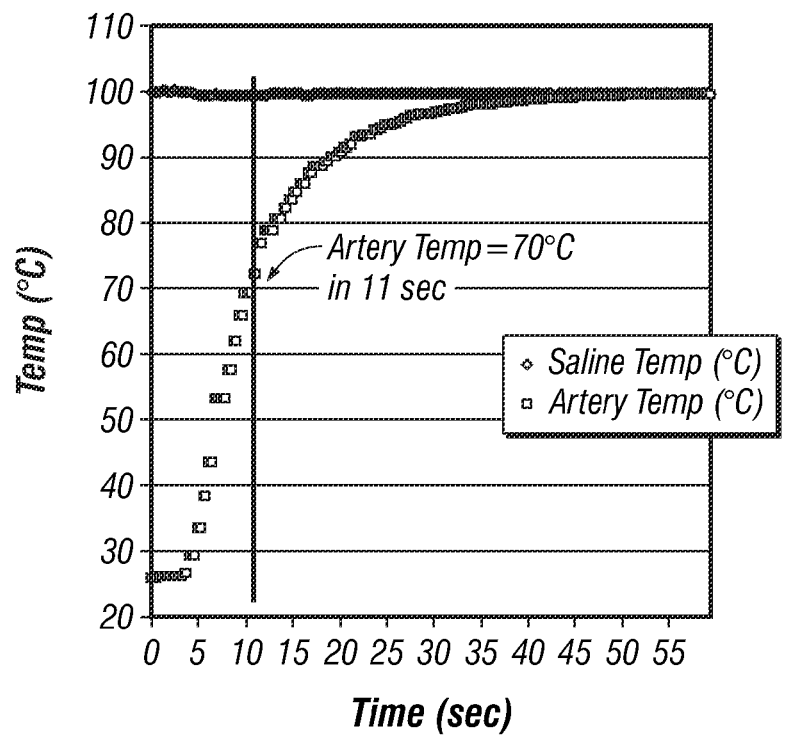
FIG. 52 is a graph of temperature change during heating of the experimental setup of FIGS. 50 and 51.
Figure 53:
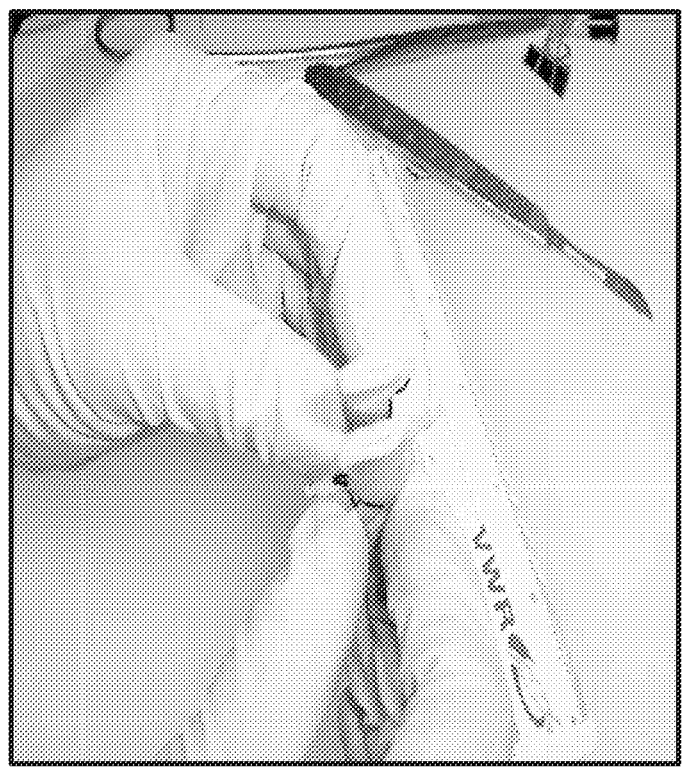
FIG. 53 is a photograph of the cross-section of the artery treated in the experiment of FIG. 50-52.

FIG. 52 is a graph of the measured temperature from the thermocouple located within the TAO during the time in which the apparatus was submerged in boiling saline. The temperature of the bovine artery reached 70° C. (a targeted temperature at which the native perivascular collagen is denaturaized and forms an extensive fibrin network that covers the arteriotomy) within 11 seconds and then equilibrates to 100° C. within 40 seconds. The temperature of the boiling saline bath was measured but remained constant at 100° C. Upon removal of the apparatus from the boiling saline, the spring clamps and aluminum plates were removed and the artery was cut in order to inspect the lumen to observe if any portion of the intimal surface was welded together. As illustrated in FIG. 53 the artery springs opened after being cut indicating that there was no occurrence of tissue welding during TAO and thermal dosing. Lastly, the bovine artery was pressure tested to evaluate the strength of the sealed arteriotomy. The artery was submerged in room temperature saline and fully pressurized with air and the pressure was recorded while being increased until the air leaked through the arteriotomy. Table 3 illustrates the results of the destructive sealed arteriotomy pressure testing. Over seven experiments, the intimal surface of the arteries did not weld shut and the arteriotomy was sealed and successfully pressure tested up to at least 3 psi.

TABLE 3

Pressure and welding testing of bovine arteries under TAO.

| Artery | Welded? | Pressure resistance of arteriotomy seal | Time occluded above 70° C. |
| --- | --- | --- | --- |
| 1 | No | 3 psi (155 mmHg) | 49 sec |
| 2 | No | >4 psi (207 mmHg) | 46 sec |
| 3 | No | >4 psi (207 mmHg) | 50 sec |
| 1 | No | 3.3 psi (171 mmHg) | 47 sec |
| 2 | No | >5 psi (259 mmHg) | 53 sec |
| 3 | No | >4 psi (207 mmHg) | 49 sec |
| 4 | No | >5 psi (259 mmHg) | 49 sec |

By monitoring the blood flow levels in the artery 28 while measuring the applied pressure, one can determine the optimal applied pressure and thereby maintain this pressure throughout the procedure. FIG. 12 is an illustration of one possible user interface that displays the amount of therapeutic applicator compression 120 applied by the user. The display may be coupled to the blood flow sensor to provide an indication of blood flow and hence compression. This user interface may be continually viewed by the user to insure proper compression is applied by the therapeutic applicator.

In one embodiment, the pressure sensing capability of piezoelectric material in the ultrasound transducers located on the applicator may be used to monitor the pressure applied by the applicator. This method gives a direct measurement of the pressure at the surface of the applicator. This pressure can be correlated with typical pressures required to stop puncture track blood flow, maintain artery patency, partially occlude the artery, or fully occlude the artery. In other embodiments described above, the pressure may be monitored by sensors located on a targeting catheter (e.g., piezoelectric sensors that measure blood flow using Doppler effects).

The amount of pressure at the surface of the applicator transducers can be detected using impedance changes within the piezoelectric elements or a change in voltage at the element. This technique allows detection of pressure directly at the applicator face. In addition, uneven pressure may be detected by separately making measurements from multiple elements at different spatial locations. By using the existing piezoelectric elements in the therapeutic ultrasound array, no additional materials need to be added. Pressure at the surface of the applicator can be correlated to the occlusion status of the vessel and to the compression required to stop blood flow up the introducer track. The existing capability in the generator may be used to monitor power, voltage, current and phase.

Piezoelectricity is a property of certain classes of crystalline materials including natural crystals of Quartz, Rochelle Salt and Tourmaline as well as manufactured ceramics or polymer films such as Lead Zirconate Titanates (PZT) and polyvinylidene fluoride. When an electric field is applied to the materials, the material deforms depending on the orientation. Conversely, when a stress is applied, an electric field is produced in the material.

In one embodiment, the applicator design uses PZT to produce an ultrasound wave when excited electrically. Since PZT is a synthetic crystal structure, the material is naturally isotropic and therefore non-piezoelectric. PZT must go through a poling process where a high voltage is applied at elevated temperatures to orient the net effect of the material domains in one direction. During the poling process, the material expands in the direction of the electric field.

After the PZT has been poled, expansion or contraction of the material will create a build-up of charge at the poling electrodes. If the compression force is in the poling direction, then the voltage polarity detected is the same as the poling voltage. If a tensile force is applied, then the voltage polarity detected is the opposite of the poling voltage.

This piezoelectric effect can be used to detect the amount of pressure at the surface of the transducer. The magnitude of the voltage is related to the receiving constant (g) of the piezoelectric material as well as the magnitude of the stress applied (T) and thickness of the ceramic (t).

$$V_{oc}=g*T*t \quad (eq. 8)$$

where $V_{oc}$ is the open circuit voltage received at the element. Therefore, if a resistive load is connected to the terminals of the device, the charge created would be electrically dissipated. The shape of the signal at the piezoelectric element is dependent on the impulse of the stress and the time constant with the load. The amount of charge on the device is dependent on the voltage and element capacitance.

Figure 16:
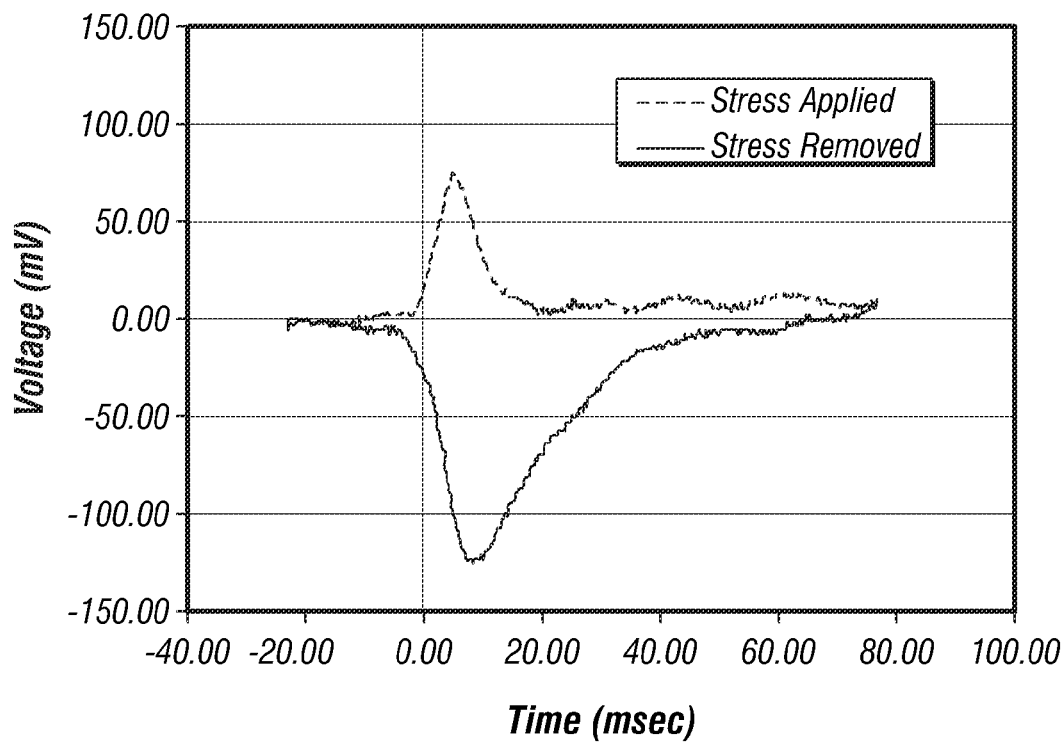
FIG. 16 is a graph showing voltage measured on a piezoelectric element from external stress (hard surface).
Figure 17:
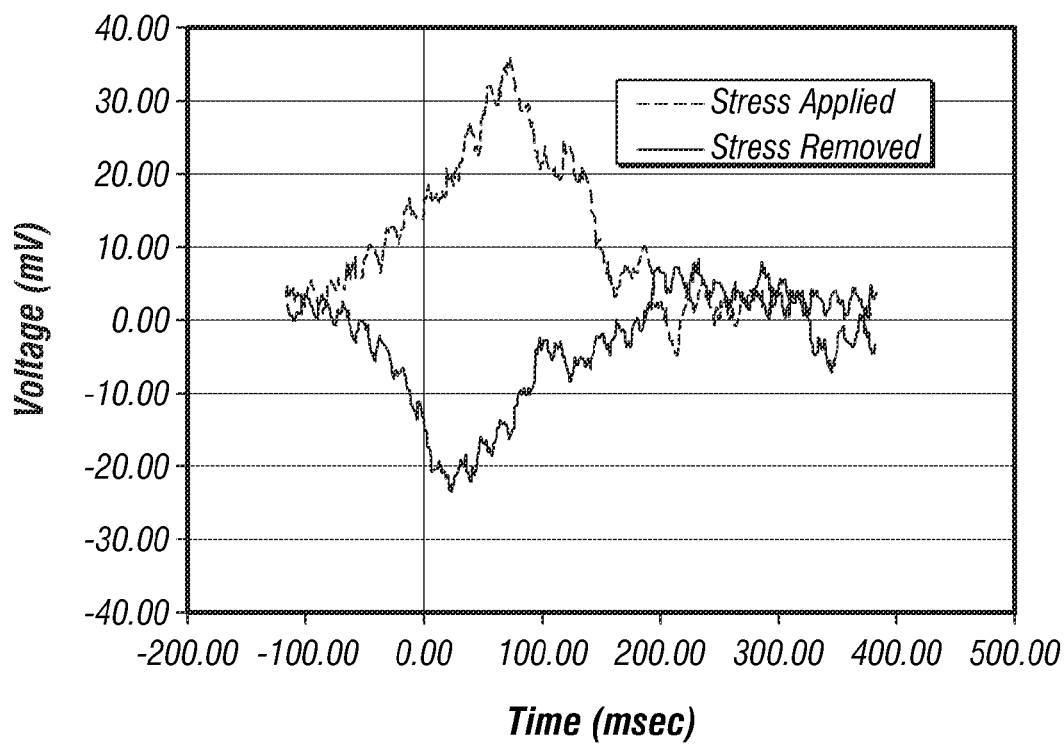
FIG. 17 is a graph showing voltage measured on a piezoelectric element from external stress (thumb).

In order to test the significance of this effect, an Antares VF10-5 transducer (Siemens AG, Munich, Germany), 10× probe, and oscilloscope was used to detect the voltage produced by a stress. One element in the VF10-5 transducer was connected to the 10× probe. The 10× probe was connected to a Tektronix oscilloscope (Tektronix, Inc., Beaverton, Oreg.) that was set for a single shot trigger. The transducer face was then pressed onto a hard surface and released. Similarly, the transducer face was pressed with a thumb and released. FIGS. 16 and 17 show the magnitude of the voltage detected. Since the charge on the transducer element is being dissipated through the 10× probe, the shorter the impulse, the larger the voltage signal detected. Overall, voltages above 20 mV were detected in this experiment (FIGS. 16 and 17). This is significant given the overall small element size (approximately 150 um wide by 5 mm tall) and long coaxial cable (2.1 m) between the element and 10× probe.

Although the experiment with the VF10-5 showed that pressure changes were detectable, the magnitude detected is dependent on impulse signal created by the impulsive load delivered.

Next, an experiment was conducted to detect the impedance of the therapeutic elements with and without a pressure at the face. A therapeutic applicator was placed in a water bath and a low voltage (3 V) CW signal at 2 MHz from the generator excited the elements of the transducer. The power, voltage, current and phase were monitored. Next, pressure was applied to the face of the transducer and the variables were again monitored. Phase changes on the order of 10 degrees were detected when the pressure was applied. Since the current and voltage waveforms were more in-phase with the application of a compressive stress, the power increased. A force balance can be applied to determine the relationship between pressure magnitude and amount of phase change.

Another means to monitor the status of the a vessel (open, partially occluded or fully occluded) is to use an acoustic Doppler system placed onto the patients skin to analyze vessel wall Doppler sounds to provide an indication of "proper" compression levels and on-location feedback. This measurement is useful since the compression of the artery will affect the Doppler sounds obtained from a transducer that is mounted perpendicular to the flow even though there is no flow signal. Turbulence and wall motion will be present which will yield different Doppler signals than when the arteries is either fully open or fully collapsed.

Figure 7F:
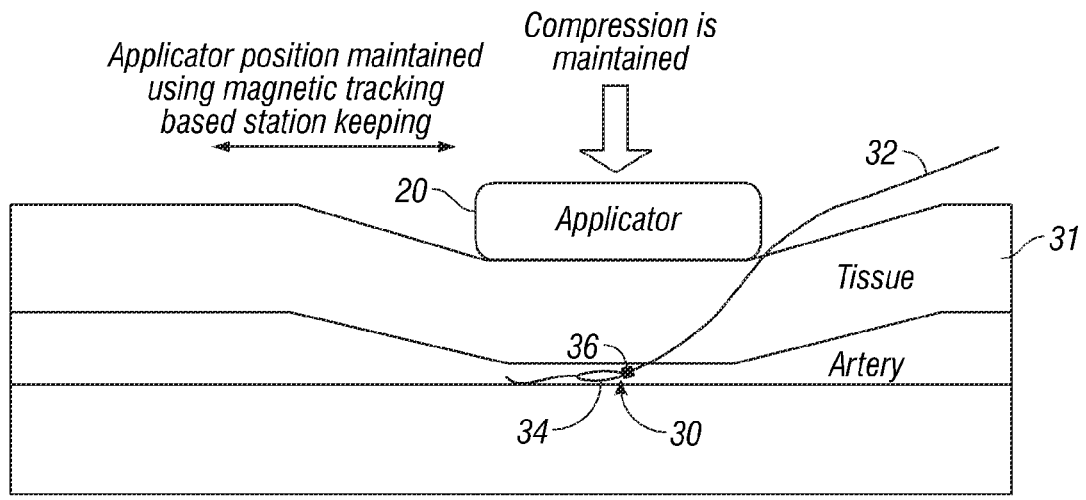
FIG. 7F is a diagram of a vascular closure procedure at the initiation of station keeping.

Returning to the discussion of the flowchart in FIG. 5, at block 110, after the desired level of compression is applied, a station keeping method can be initiated to maintain proper alignment of the applicator during therapy. Subsequent to alignment, the targeting catheter continues to reside in the puncture tract with the beacon being proximate to the arteriotomy. The application of therapeutic energy may be applied at this point, however, in some embodiments, the procedure involves removing the targeting catheter from the arteriotomy location (discussed in more detail below). Removing the targeting catheter allows for the most effective acoustic hemostasis. In some embodiments, methods are provided to ensure that the therapeutic applicator stays focused upon the arteriotomy in the absence of the beacon. In anticipation of the targeting catheter being removed, a station keeping method may be initiated as illustrated in FIG. 7F. Station keeping, which is described in detail below, may be used to track tissue 31 motion (e.g., specifically the arteriotomy 30 or tissue proximate to it) using acoustic waves with radio frequency signal processing techniques (referred to herein as RfUME (Radio Frequency Ultrasound Motion Estimate)). Specifically, at least three acoustic transducers, pistons, or arrays may be used to track the motion of a common point. Movement may be determined by comparing a reference signal to a present signal. The difference between the signals determines the amount of movement of the tissue 31 relative to the transducers and hence relative to the applicator 20.

Accordingly, in anticipation of removing the targeting catheter 32, the ATOF targeting of the arteriotomy targeting aid 34 and beacon 36 may be replaced by station keeping of the arteriotomy site 30. This station keeping information may be displayed to the user through the same targeting user interface as depicted in FIG. 12. This display provides feedback to a user so that the user can maintain the focus point of the therapeutic energy applicator 20 at the site of the arteriotomy 30.

The purpose of station keeping is to track tissue motion. In one embodiment, at least three transducers may be used to track the motion of a common point. The motion may be tracked using a variety of techniques including traditional pulse-echo techniques as well as a pitch-catch sequence. The pitch-catch algorithm has several advantages when compared with conventional pulse-echo techniques. The acquisition time required to determine the motion is significantly reduced, thereby reducing the susceptibility to jitter, allowing the system to see faster movements, and allowing more time for therapy if interleaving is used. In addition, a greater amount of redundancy is achieved in less acquisition time for improved motion estimation. If the pitch-catch technique is allocated the same acquisition time as the conventional approach, the SNR of each acquisition is also increased, thereby increasing penetration and improving tracking ability. Finally, system complexity is reduced by reducing hardware requirements (e.g. transmit-receive switches).

The overlapping beam pattern of at least three ultrasound transducers can be used to track the motion in three dimensions. In this case, a unit vector from the transducer to the coordinate system of the interrogated point describes the beam direction and sensitivity to specific types of movement. If the interrogated point moves relative to the transducer, then a certain amount of movement will be detected by each transducer depending on the unit vector. In this case, the amount of motion detected at one transducer is described as:

$$motion_k = a_{kx} \cdot \delta x + a_{ky} \cdot \delta y + a_{kz} \cdot \delta z \quad (9)$$

where $\delta x$, $\delta y$, and $\delta z$ are the small movements of the point from the original position in three dimensions, and $a_{kx}$, $a_{ky}$, and $a_{kz}$ are the unit vector components for the $k^{th}$ transducer. The amount of motion can be calculated by measuring the amount of movement from at least two other transducers and realizing that the motion detected in ultrasound is related to a time shift:

$$motion_k = t_k \cdot \frac{c_{tissue}}{2} \quad (10)$$

where $t_k$ is the time difference between the first signal and the next signal, and $c_{tissue}$ is the velocity of sound in tissue. The factor of two occurs in equation (10) due to the time required for the ultrasound pulse to travel out and back from the interrogation point. The time difference $t_k$ is determined by fitting a previous or reference pulse to the current pulse. A correlation technique is typically used to determine the best fit. Therefore, the system can be described by combining equations (9) and (10) to obtain:

$$\begin{bmatrix} t_1 \\ t_2 \\ t_3 \end{bmatrix} = \frac{2}{c_{tissue}} \cdot \begin{bmatrix} a_{1x} & a_{1y} & a_{1z} \\ a_{2x} & a_{2y} & a_{2z} \\ a_{3x} & a_{3y} & a_{3z} \end{bmatrix} \cdot \begin{bmatrix} \delta x \\ \delta y \\ \delta z \end{bmatrix} \quad (11)$$

If the time differences are known as well as the unit vectors given the system configuration, then the amount of motion can be determined. If the system has multiple transducers, then redundancy exists in the system and multiple solutions can be calculated.

In the pitch-catch approach, instead of transmitting and receiving on the same transducer, energy is transmitted by only one transducer and the backscatter is detected by the other transducers. For example, if a three transducer system is used, the transmit event might occur on transducer 1 with transducer 2 and 3 detecting the backscatter. A second transmit might occur on transducer 2 with transducer 1 and 3 detecting the backscatter. In this case, the motion detected is a combination of the unit vectors from the transmit and receive transducers.

$$\text{motion}_k = (a_{kx} + a_{mx}) \cdot \delta x + (a_{ky} + a_{my}) \cdot \delta y + (a_{kz} + a_{mz}) \cdot \delta z \quad (12)$$

where the directional vector is the summation of the unit vector components for the $k^{th}$ and $m^{th}$ transducers. Another interesting result of equation 12 is the lack of identification of the transmit and receive transducers. In other words, reciprocity exists in equation (12). The $k^{th}$ transducer could either be the transmitter or receiver and the motion detected is the same amount.

Similar to the conventional pulse-echo approach, the amount of motion detected is related to the time shift in the receive pulse. However, in this case the factor of two is eliminated because the pulse is not going out and coming back; rather it is detected by the path between the transmitter and receiver which is already represented in the directional vector.

$$\text{motion}_k = t_k \cdot c_{tissue} \quad (13)$$

Equations (12) and (13) can be combined to show the relationship between the time shift and the motion of the interrogation point.

$$\begin{bmatrix} t_1 \\ t_2 \\ t_3 \end{bmatrix} = \frac{1}{c_{tissue}} \cdot \begin{bmatrix} (a_{1x} + a_{2x}) & (a_{1y} + a_{2y}) & (a_{1z} + a_{2z}) \\ (a_{1x} + a_{3x}) & (a_{1y} + a_{3y}) & (a_{1z} + a_{3z}) \\ (a_{2x} + a_{3x}) & (a_{2y} + a_{3y}) & (a_{2z} + a_{3z}) \end{bmatrix} \cdot \begin{bmatrix} \delta x \\ \delta y \\ \delta z \end{bmatrix} \quad (14)$$

In this case, the transmit might occur on transducer 1 and detection on transducers 2 and 3. This would yield $t_1$ and $t_2$. A second transmit might occur on transducer 2 and detection could occur on transducer 1 and 3. In this case, $t_1$ and $t_3$ are determined; however, note that only $t_3$ is required to allow for equation (14) to be solved for the movement. The extra $t_1$ measured time could be used to improve the estimate (SNR) or just discarded.

Compared to the conventional approach, only two transmit events are required to solve for the movement in equation 14. Therefore, the amount of time to acquire and calculate a movement has decreased by 33%. This extra time can be used to increase the acquisition rate and detect faster movements. This extra time may also be dedicated for therapy.

The pitch-catch method also has the advantage for reducing the hardware required. For example, in the three transducer system, two transducers require a transmit/receive architecture with the other transducer only requiring a receive architecture. In the conventional case, all three transducers need a transmit/receive architecture.

In the case of more than three transducers, the pitch-catch approach offers the possibilities of motion estimation redundancy with only one transmit. For example, if the system has five transducers, then transmitting on one transducer yields the possibility of four different solutions. This redundancy allows for better motion estimation through averaging techniques or solution selection given the signal quality. In the conventional approach, at least four transmit events are required for this amount of redundancy in a five transducer system.

In some embodiments, the pulse-echo and pitch-catch approach may be combined in a hybrid approach to yield an even faster acquisition. In this case, equation (14) becomes:

$$\begin{bmatrix} t_1 \\ t_2 \\ \frac{t_3}{2} \end{bmatrix} = \frac{1}{c_{tissue}} \cdot \begin{bmatrix} (a_{1x} + a_{2x}) & (a_{1y} + a_{2y}) & (a_{1z} + a_{2z}) \\ (a_{1x} + a_{3x}) & (a_{1y} + a_{3y}) & (a_{1z} + a_{3z}) \\ (a_{1x}) & (a_{1y}) & (a_{1z}) \end{bmatrix} \cdot \begin{bmatrix} \delta x \\ \delta y \\ \delta z \end{bmatrix} \quad (15)$$

In this case, the system has transmitted on transducer 1 and received on all three transducers. Acquisition time is decreased by 67% when compared to the conventional approach with three transducers.

Figure 18:
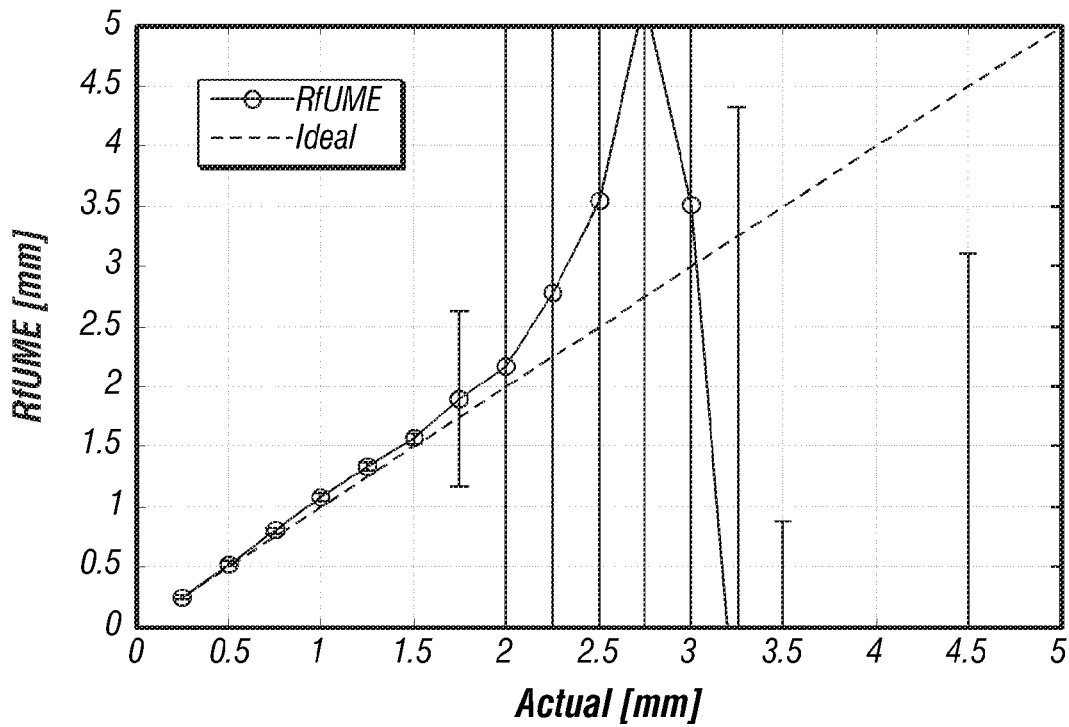
FIG. 18 is a graph showing the accuracy of station keeping detected movement in the X-axis using a pitch-catch algorithm.
Figure 19:
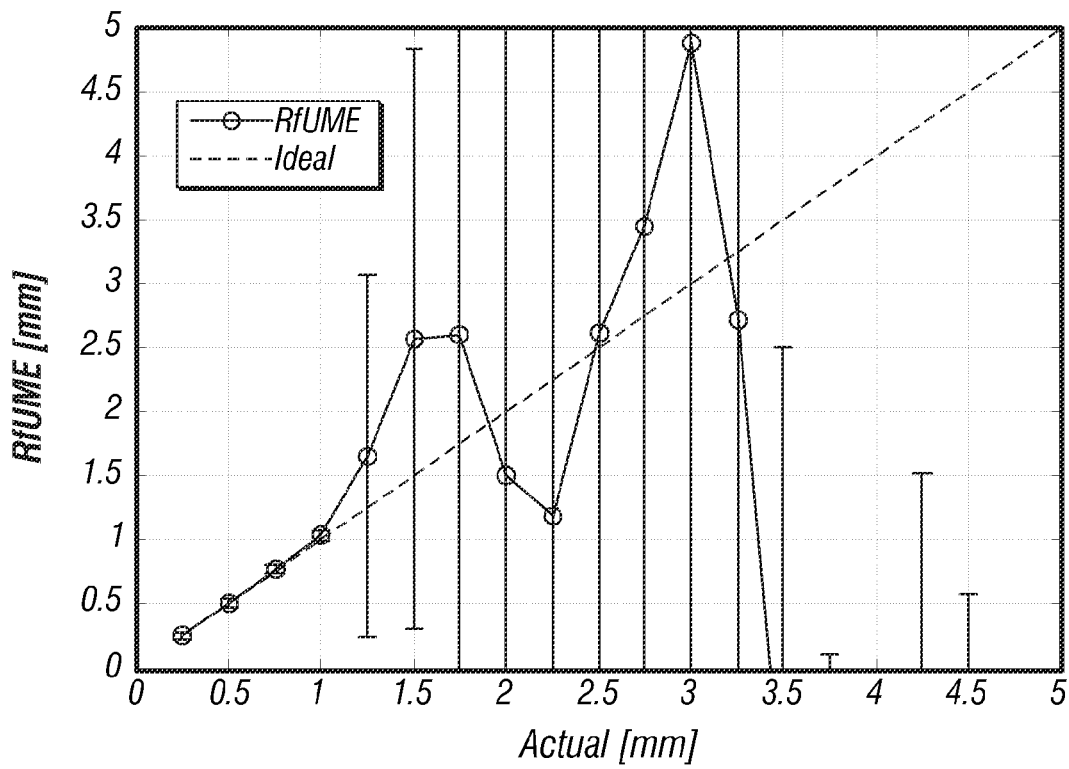
FIG. 19 is a graph showing the accuracy of station keeping detected movement in the Y-axis using a pitch-catch algorithm.
Figure 20:
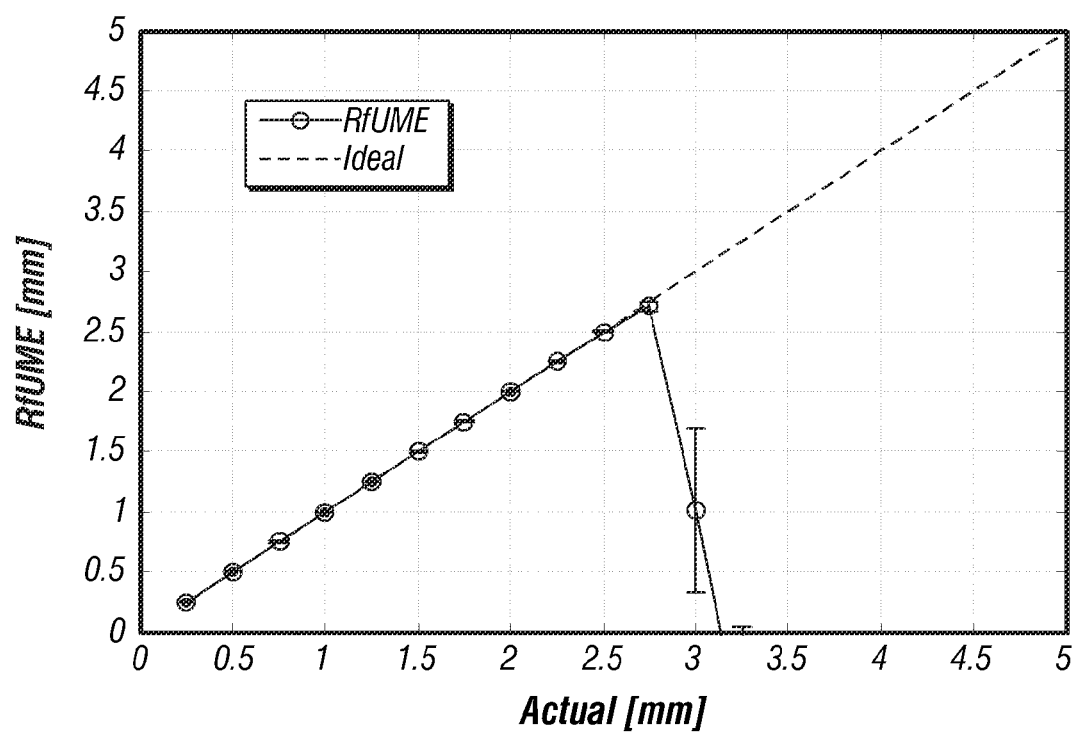
FIG. 20 is a graph showing the accuracy of station keeping detected movement in the Z-axis using a pitch-catch algorithm.

In order to evaluate the performance of the pitch-catch technique, a fixture with three 6 mm ultrasonic pistons was design and tested. The fixture was coupled to an agar phantom and pitch-catch data was acquired and motion estimation was calculated off-line. A Panametrics 5072PR pulser was used as the transmitter and a Metrotek MR101 receiver was used. FIGS. 18, 19 and 20 are graphs showing the correlation between actual position and that determined using the pitch-catch RfUME algorithm described above for X, Y, and Z coordinates, respectively. The ideal result of one-to-one correlation is plotted as a line of slope 1. The distances determined using the RfUME algorithm are plotted as circles. FIGS. 18, 19 and 20 show that after a certain amount of movement, the algorithm stops tracking. This result is primarily due to the beam width and the transducer directionality. For example, improvement in tracking x and y movement can be accomplished by widening the beam or placing the transducer at a steeper interrogation angle such that the transducer has greater detection of x and y movement. Although the algorithm stops tracking after a certain amount of movement, this effect can be avoided in real-time by referencing when required.

As discussed above, movement relative to tissue is determined by comparing a reference signal to a present signal. The phase difference between these signals helps determine the amount of movement of the transducer or tissue. Unfortunately, this motion estimation is a simplification of the actual movement. Accordingly, such algorithms have the potential of significant error if the transducer or tissue moves by large amounts or if the transducer is tipped or tilted. Thus, in some embodiments, a recursive algorithm is used to determine the movement. Results show that the recursive algorithm tracks movement due to rotation much better than the simplified version. The error for translational movement is also reduced from approximately 5% to less than 2%. There are several benefits of using the recursive algorithm approach. The motion estimation due to elevation or roll rotation is significantly improved, especially in the depth dimension. In addition, the standard deviation of the motion estimation is reduced from approximately 5% to less than 2%. No simplification of the acoustic formulas is required to track movement. Furthermore, only a small amount of iterations are required for the system to reach equilibrium In some embodiments, a conventional pulse-echo approach may be utilized for station keeping. The overlapping beam pattern of at least three transducers can be used to track the motion in three dimensions. In this case, a unit vector from the transducer to the coordinate system of the interrogated point describes the beam direction and sensitivity to specific types of movement. If an interrogated point moves relative to the transducer, then a certain amount of movement will be detected by each transducer depending on the unit vector. In this case, the amount of motion detected at one transducer is described as:

$$\text{motion}_k = a_{kx} \cdot \Delta x + a_{ky} \cdot \Delta y + a_{kz} \cdot \Delta z \tag{16}$$

where $\delta x$, $\delta y$, and $\delta z$ are the small movements of the point from the original position in three dimensions, and $a_{kx}$, $a_{ky}$, and $a_{kz}$ are the unit vector components for the $k^{th}$ transducer. The amount of motion can be calculated by measuring the amount of movement from at least two other transducers and realizing that the motion detected in ultrasound is related to a time shift:

$$\text{motion}_k = t_k \cdot \frac{c_{tissue}}{2} \tag{17}$$

where $t_k$ is the time difference between the first signal and the next signal, and $c_{tissue}$ is the velocity of sound in tissue. The factor of two occurs in equation (17) due to the time required for the ultrasound pulse to travel out and back from the interrogation point. The time difference $t_k$ is determined by fitting a previous or reference pulse to the current pulse. A correlation technique is typically used to determine the best fit. Therefore, the system can be described by combining equations (16) and (17) to obtain:

$$\begin{bmatrix} t_1 \\ t_2 \\ t_3 \end{bmatrix} = \frac{2}{c_{tissue}} \cdot \begin{bmatrix} a_{1x} & a_{1y} & a_{1z} \\ a_{2x} & a_{2y} & a_{2z} \\ a_{3x} & a_{3y} & a_{3z} \end{bmatrix} \cdot \begin{bmatrix} \Delta x \\ \Delta y \\ \Delta z \end{bmatrix} \tag{18}$$

If the time differences are known as well as the unit vectors given the system configuration, then the amount of motion can be determined. If the system has multiple transducers, then redundancy exists in the system and multiple solutions can be calculated.

A recursive approach may also be used with convention pulse-echo techniques. In the recursive approach, instead of assuming that the unit vector from the center of the transducer to the interrogation point completely maps the movement, a new approach is formulated using the distance formula. For example, assume that the transducers are in the same plane a distance 'R' from the center of a circle. In this case, the original distance to a common interrogation point is:

$$d_{io} = \sqrt{\left(R \cdot \cos\left(\frac{2 \cdot \pi}{N} \cdot (i-1)\right)\right)^2 + \left(R \cdot \sin\left(\frac{2 \cdot \pi}{N} \cdot (i-1)\right)\right)^2 + z_f^2} \tag{19}$$

where R is the distance from the center of the circle to the center of each transducer, N is the number of transducers which is greater than or equal to three, i varies from 1 to N, and $z_f$ is the distance to the interrogation point. In this case, the interrogation point is only on the z axis. Equation (19) simplifies to:

$$d_{io} = \sqrt{R^2 + z_f^2} \tag{20}$$

This results makes sense for this system design, given that each transducer is equidistant from the interrogation point.

If the target moves to a new point described as ($\Delta x$, $\Delta y$, $z_f + \Delta z$), where the movement can be caused by tissue movement or transducer movement, the new distance to the target is given as:

$$d_{in} = \sqrt{\left(R \cdot \cos\left(\frac{2 \cdot \pi}{N} \cdot (i-1)\right) + \Delta x\right)^2 + \left(R \cdot \sin\left(\frac{2 \cdot \pi}{N} \cdot (i-1)\right) + \Delta y\right)^2 + (z_f + \Delta z)^2} \tag{21}$$

In the technique to determine motion, the phase difference of a reference line to a current line is determined. This technique is similar to calculating the difference between the distance vectors.

$$v_{in} = d_{in} - d_{io} \tag{22}$$

where $v_{in}$ is the difference between the two distances for transducer 'i'. Unfortunately, it is difficult to solve equation (22) for $\Delta x$, $\Delta y$, and $\Delta z$ because of the square root. Therefore, it may be possible to calculate the movement if equations (20) and (21) are first squared.

$$d_{in}^2 - d_{io}^2 = \left(R \cdot \cos\left(\frac{2 \cdot \pi}{N} \cdot (i-1)\right) + \Delta x\right)^2 + \left(R \cdot \sin\left(\frac{2 \cdot \pi}{N} \cdot (i-1)\right) + \Delta y\right)^2 + (z_f + \Delta z)^2 - (R^2 + z_f^2) \tag{23}$$

Simplifying equation (23) yields:

$$\frac{d_{in}^2 - d_{io}^2 - (\Delta^2 x + \Delta^2 y + \Delta^2 z)}{2} = R \cdot \cos(\theta_i) \cdot \Delta x + R \cdot \sin(\theta_i) \cdot \Delta y + z_f \cdot \Delta z \tag{24}$$

where $\theta_i$ is $2\pi/N(i-1)$.

If both sides of equation (24) are divided by equation (20), then:

$$\frac{d_{in}^2 - d_{io}^2 - (\Delta^2 x + \Delta^2 y + \Delta^2 z)}{2 \cdot \sqrt{R^2 + z_f^2}} = a_{ix} \cdot \Delta x + a_{iy} \cdot \Delta y + a_{iz} \cdot \Delta z \tag{25}$$

where $a_{ix}$, $a_{iy}$, and $a_{iz}$ are the x, y and z unit vectors from transducer 'i'.

In practice, the actual distances are not calculated from the signal vectors, rather the time differences between the pulses are calculated. A distance can be related to time by knowing the speed of sound.

$$t_i = \frac{d_i}{\left(\frac{c_{tissue}}{2}\right)} \quad (26)$$

If equation (26) is substituted into equation (25), then:

$$\left(\frac{c_{tissue}}{2}\right)^2 \cdot \left(\frac{t_{in}^2 - t_{io}^2 - \frac{4}{c_{tissue}^2}(\Delta^2 x + \Delta^2 y + \Delta^2 z)}{2 \cdot \sqrt{R^2 + z_f^2}}\right) = \quad (27)$$

$$a_{ix} \cdot \Delta x + a_{iy} \cdot \Delta y + a_{iz} \cdot \Delta z$$

Equation (27) can now be placed into matrix form for a three transducer system:

$$\frac{c_{tissue}^2}{8 \cdot \sqrt{R^2 + z_f^2}} \cdot \quad (28)$$

$$\begin{bmatrix} t_{1n}^2 - t_{1o}^2 - \frac{4}{c_{tissue}^2}(\Delta^2 x + \Delta^2 y + \Delta^2 z) \\ t_{2n}^2 - t_{2o}^2 - \frac{4}{c_{tissue}^2}(\Delta^2 x + \Delta^2 y + \Delta^2 z) \\ t_{3n}^2 - t_{3o}^2 - \frac{4}{c_{tissue}^2}(\Delta^2 x + \Delta^2 y + \Delta^2 z) \end{bmatrix} = \begin{bmatrix} a_{1x} & a_{1y} & a_{1z} \\ a_{2x} & a_{2y} & a_{2z} \\ a_{3x} & a_{3y} & a_{3z} \end{bmatrix} \cdot \begin{bmatrix} \Delta x \\ \Delta y \\ \Delta z \end{bmatrix}$$

A recursive formula is generated by solving equation (28) for $\Delta x$, $\Delta y$, and $\Delta z$. In this case, the calculated motion is still a function of the distance squared. Therefore, in order to get an initial estimate of the movement, assume that the time differences are much larger than the sum of the square of the movement divided by the speed of sound in tissue. In this case, the solution is:

$$\frac{c_{tissue}^2}{8 \cdot \sqrt{R^2 + z_f^2}} \cdot \begin{bmatrix} a_{1x} & a_{1y} & a_{1z} \\ a_{2x} & a_{2y} & a_{2z} \\ a_{3x} & a_{3y} & a_{3z} \end{bmatrix}^{-1} \cdot \begin{bmatrix} t_{1n}^2 - t_{1o}^2 \\ t_{2n}^2 - t_{2o}^2 \\ t_{3n}^2 - t_{3o}^2 \end{bmatrix} = \begin{bmatrix} 1 & 0 & 0 \\ 0 & 1 & 0 \\ 0 & 0 & 1 \end{bmatrix} \cdot \begin{bmatrix} \Delta x \\ \Delta y \\ \Delta z \end{bmatrix} \quad (29)$$

Also note that:

$$t_{io}^2 = \left(\frac{2}{c_{tissue}}\right)^2 \cdot (R^2 + z_f^2) \quad (30)$$

This result is the initial calculation of the movement and the estimates for $\Delta x$, $\Delta y$, and $\Delta z$ can be placed in the left side of the equation, and the motion calculated again according to equation (31).

$$\frac{c_{tissue}^2}{8 \cdot \sqrt{R^2 + z_f^2}} \cdot \begin{bmatrix} a_{1x} & a_{1y} & a_{1z} \\ a_{2x} & a_{2y} & a_{2z} \\ a_{3x} & a_{3y} & a_{3z} \end{bmatrix}^{-1} \cdot \quad (31)$$

$$\begin{bmatrix} t_{1n}^2 - t_{1o}^2 - \frac{4}{c_{tissue}^2}(\Delta^2 x_{m-1} + \Delta^2 y_{m-1} + \Delta^2 z_{m-1}) \\ t_{2n}^2 - t_{2o}^2 - \frac{4}{c_{tissue}^2}(\Delta^2 x_{m-1} + \Delta^2 y_{m-1} + \Delta^2 z_{m-1}) \\ t_{3n}^2 - t_{3o}^2 - \frac{4}{c_{tissue}^2}(\Delta^2 x_{m-1} + \Delta^2 y_{m-1} + \Delta^2 z_{m-1}) \end{bmatrix} =$$

$$\begin{bmatrix} 1 & 0 & 0 \\ 0 & 1 & 0 \\ 0 & 0 & 1 \end{bmatrix} \cdot \begin{bmatrix} \Delta x_m \\ \Delta y_m \\ \Delta z_m \end{bmatrix}$$

In this case, the index m denotes the number of times through the calculation.

In order to determine the advantages using the recursive formulation, data was simulated using the Field II program by Jorgen Jensen. This allowed a phantom of random scatterers to be easily rotated in elevation and roll. A 16 element phased array operating at 2 MHz with 60% bandwidth was defined in Field II and placed uniformly around a radius of 12.5 mm. The conventional algorithm was applied to the data to determine the calculated x, y and z motion. For example, since elevation rotation is about the x-axis, movement is expected in the y and z dimensions. The recursive formula was also applied to the exact same data and a comparison was made to actual movement in x, y and z.

Figure 21:
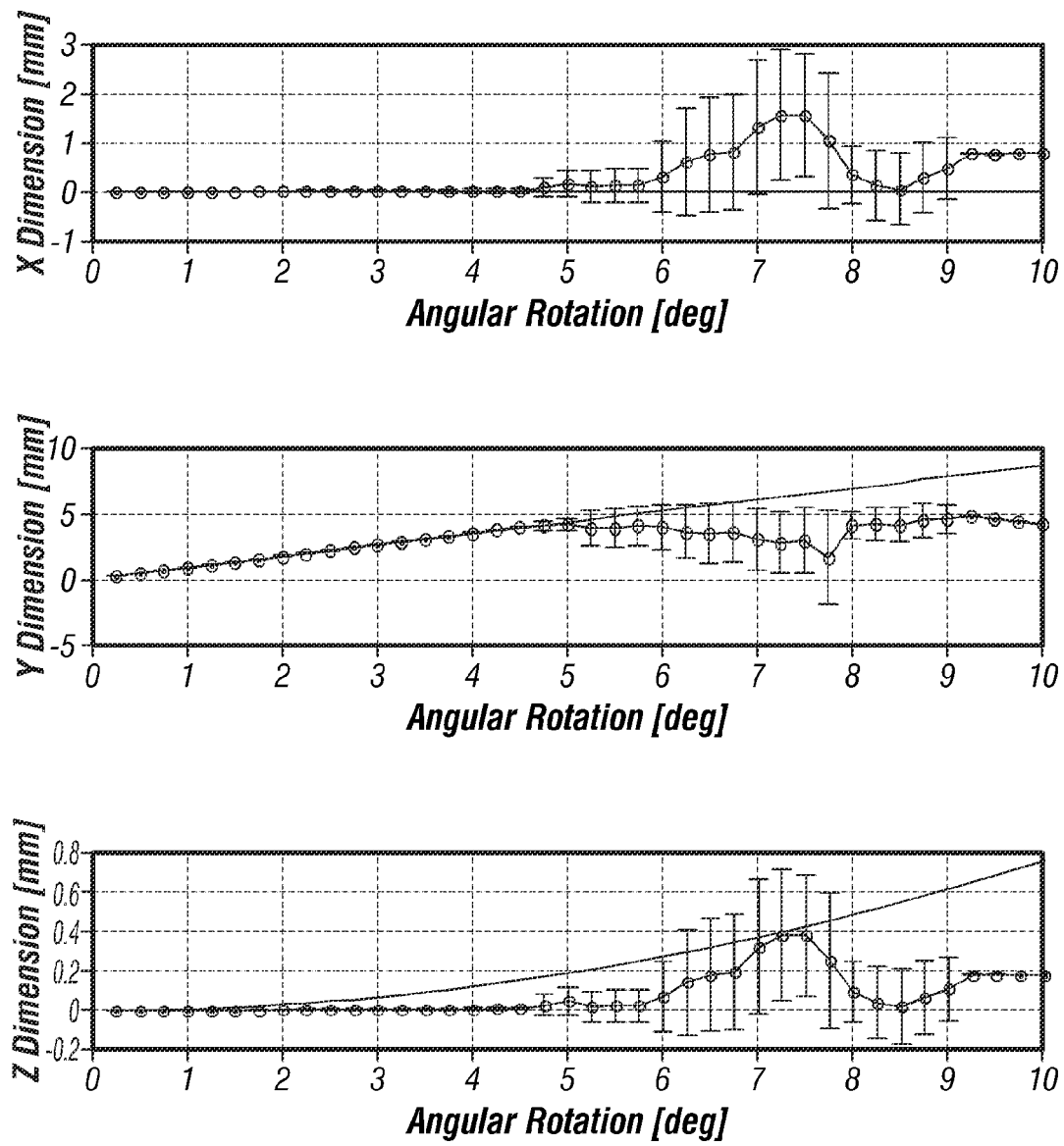
FIG. 21 depicts three graphs showing station keeping detected motion using the conventional approach for elevation rotation.
Figure 22:
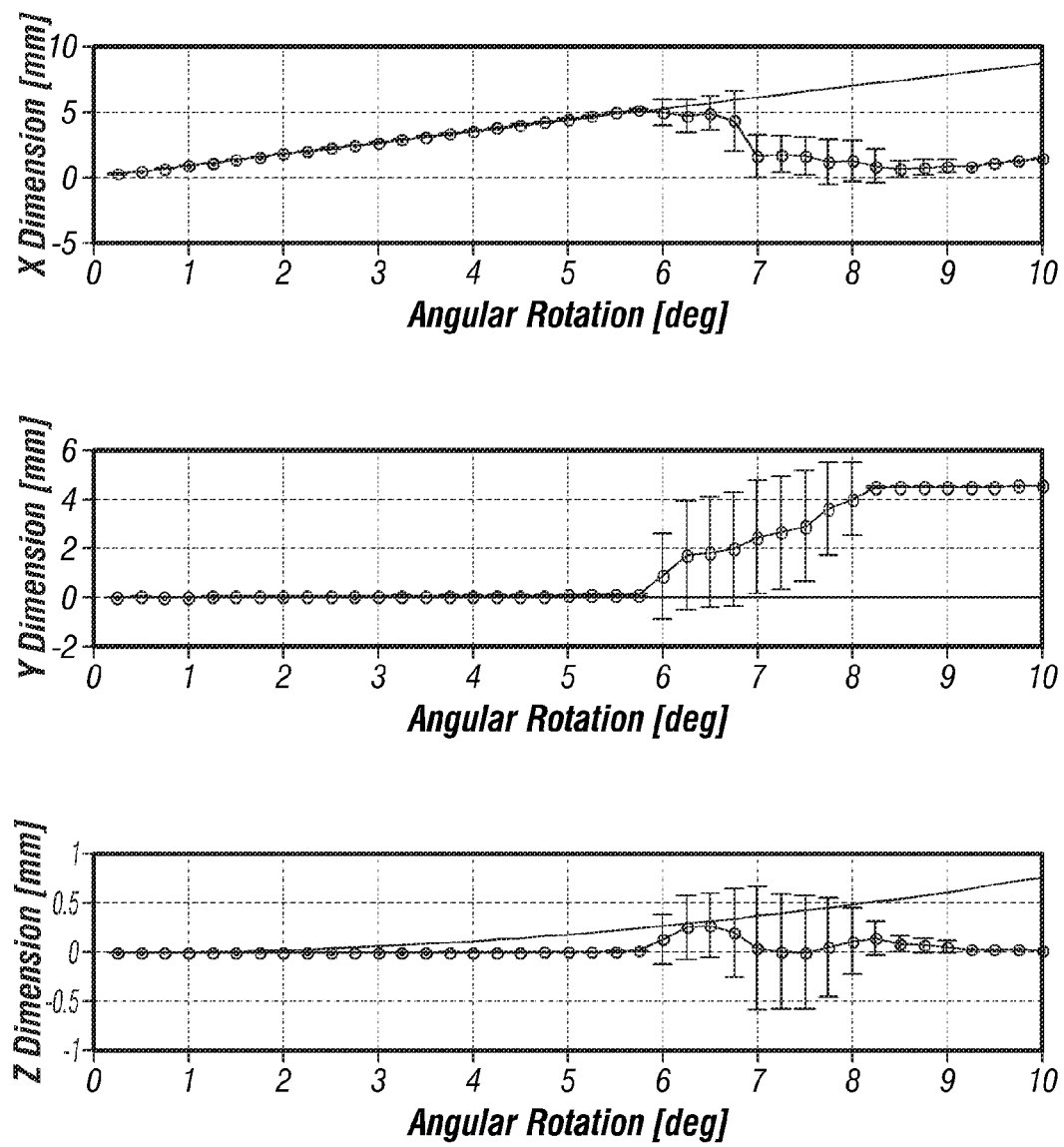
FIG. 22 depicts three graphs showing station keeping detected motion using the conventional approach for roll rotation.

FIG. 21 depicts three graphs showing the actual movement (plotted circles) in x, y and z, respectively, compared to the line representing the calculated result using the conventional technique (eq. 18) for rotation in elevation. In this case, the three phased arrays are focused at a 50 mm depth. Although this algorithm detects the y movement and lack of x movement with a high degree of accuracy, no movement is detected in the z dimension. A similar result is observed for roll rotation (see FIG. 22).

Figure 23:
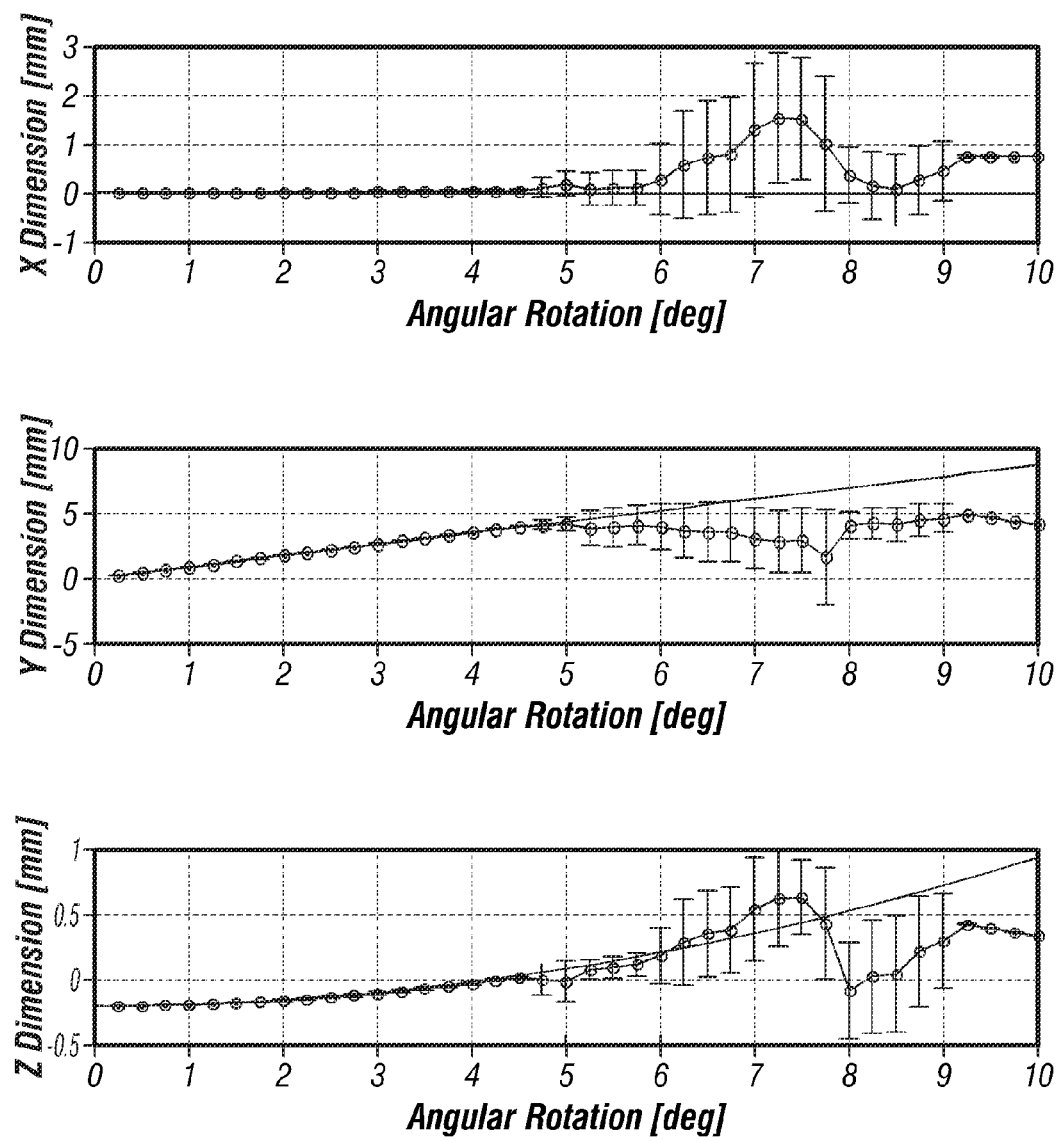
FIG. 23 depicts three graphs showing station keeping detected motion using a recursive approach for elevation rotation.
Figure 24:
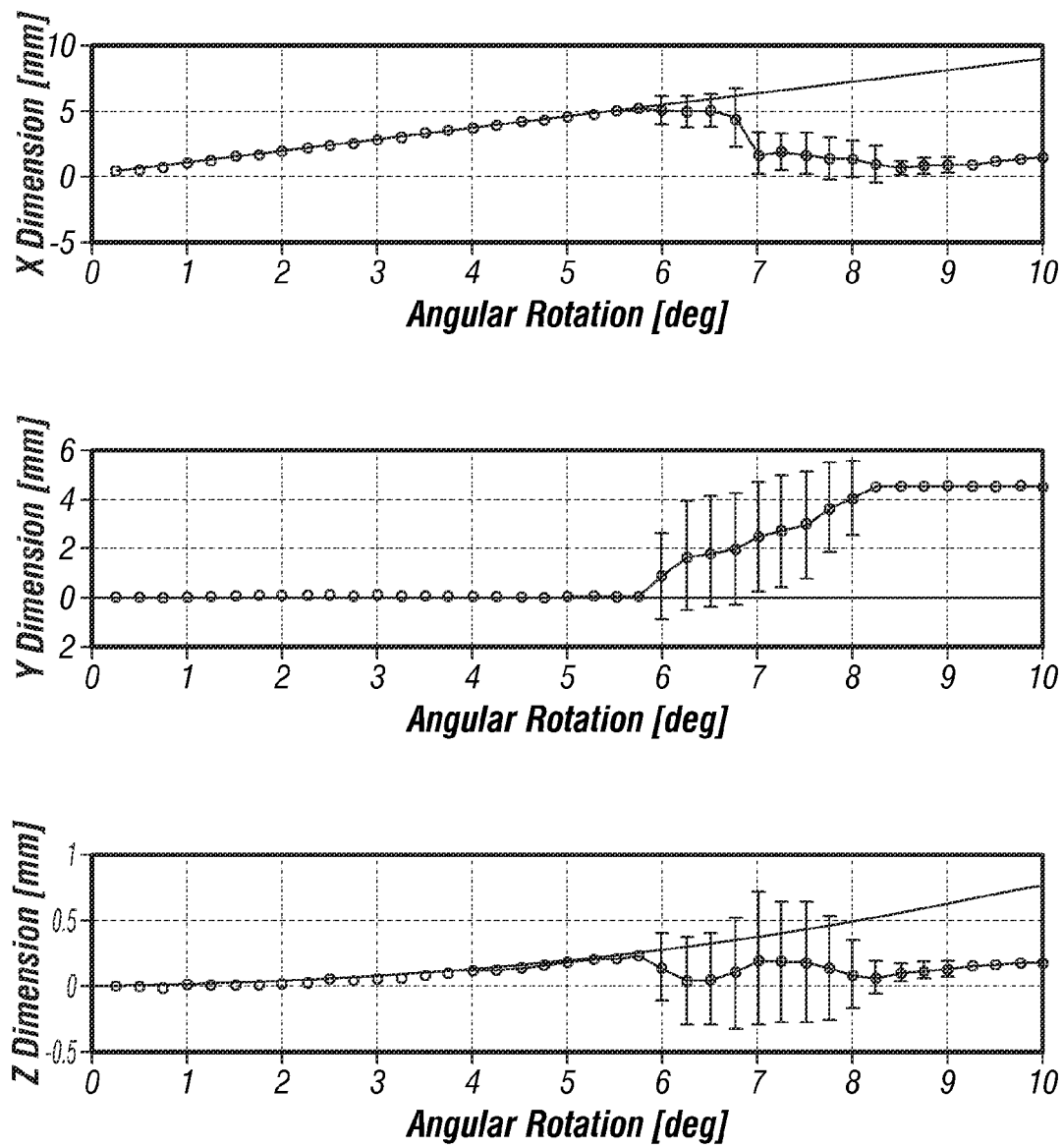
FIG. 24 depicts three graphs showing station keeping detected motion using a recursive approach for roll rotation.

FIG. 23 shows the results using the recursive formula (eq. 31) for elevation rotation. In this case, the algorithm detects accurately the motion in all three dimensions. This result only required 10 iterations of the formula (m=10). A similar result is observed for roll rotation (see FIG. 24).

A calibration process may be used to calibrate an ultrasound system used to track tissue motion. The direction of the ultrasound propagation to the focus is directly related to the amount of detected movement. Therefore, it is advantageous to know the direction vector from the transducers to the focus with a high degree of accuracy. Any errors have the potential to be compounded if re-referencing frequently. Re-referencing may be required due to the limited region that the transducers can detect movement. The following discussion describes a process to calibrate the direction of ultrasound propagation from a set of transducer, pistons or arrays. The process provides a significant reduction in potential errors resulting in improved accuracy of motion estimation with significantly reduced error for pistons or multi-element arrays, increased mechanical alignment tolerances since acoustic calibration eliminates these errors, and reduction in susceptibility to accumulation error.

The overlapping beam pattern of at least three transducers can be used to track the motion in three dimensions. In this case, a unit vector from the transducer to the coordinate system of the interrogated point describes the beam direction and sensitivity to specific types of movement. If the interrogated point moves relative to the transducer, then a certain amount of movement will be detected by each transducer depending on the unit vector. In this case, the difference in the square of distance vectors is described as:

$$d_{in}^2 - d_{io}^2 = \left(R \cdot \cos\left(\frac{2 \cdot \pi}{N} \cdot (i-1)\right) + \Delta x\right)^2 + \left(R \cdot \sin\left(\frac{2 \cdot \pi}{N} \cdot (i-1)\right) + \Delta y\right)^2 + (z_f + \Delta z)^2 - (R^2 + z_f^2) \quad (32)$$

where $\Delta x$, $\Delta y$, and $\Delta z$ are the small movements of the point from the original position in three dimensions, $d_{in}$ and $d_{io}$ are the new and original distance to the interrogation point for the $i^{th}$ transducer, and $z_f$ is the location of the focus. Equation 32 also describes a system where all of the transducers are in the same plane at a radius 'R'.

Equation (32) can be simplified to:

$$\frac{c_{tissue}^2}{8 \cdot \sqrt{R^2 + z_f^2}} \cdot \begin{bmatrix} t_{1n}^2 - t_{1o}^2 - \frac{2}{c_{tissue}^2}(\Delta^2 x + \Delta^2 y + \Delta^2 z) \\ t_{2n}^2 - t_{2o}^2 - \frac{2}{c_{tissue}^2}(\Delta^2 x + \Delta^2 y + \Delta^2 z) \\ t_{3n}^2 - t_{3o}^2 - \frac{2}{c_{tissue}^2}(\Delta^2 x + \Delta^2 y + \Delta^2 z) \end{bmatrix} = \begin{bmatrix} a_{1x} & a_{1y} & a_{1z} \\ a_{2x} & a_{2y} & a_{2z} \\ a_{3x} & a_{3y} & a_{3z} \end{bmatrix} \cdot \begin{bmatrix} \Delta x \\ \Delta y \\ \Delta z \end{bmatrix} \quad (33)$$

where $c_{tissue}$ is the velocity of sound in tissue, is the total time to the interrogation point, and $a_{im}$ are the components of the unit vectors for the respective transducers.

As equation (33) shows, solving for $\Delta x$, $\Delta y$, and $\Delta z$ requires taking the inverse of the a-matrix or directional matrix. Therefore, it is critical to accurately determine $a_{im}$ if the motion is to be tracked properly.

One method to accurately determine the directional matrix is to mount the system in a test station that offers precise control of x, y and z movement. Next, the system is coupled to tissue mimicking material. The stages are moved in x, y or z only in small increments that insures the position can be tracked. For example, suppose that the stage is only moved in the x direction such that $\Delta y$ and $\Delta z$ are zero. Equation (33) can then be simplified to the following:

$$\frac{c_{tissue}^2}{8 \cdot \sqrt{R^2 + z_f^2}} \cdot \begin{bmatrix} t_{1n}^2 - t_{1o}^2 - \frac{4}{c_{tissue}^2}(\Delta^2 x) \\ t_{2n}^2 - t_{2o}^2 - \frac{4}{c_{tissue}^2}(\Delta^2 x) \\ t_{3n}^2 - t_{3o}^2 - \frac{4}{c_{tissue}^2}(\Delta^2 x) \end{bmatrix} = \begin{bmatrix} a_{1x} \cdot \Delta x \\ a_{2x} \cdot \Delta x \\ a_{3x} \cdot \Delta x \end{bmatrix} \quad (34)$$

Since $\Delta x$ is known, equation (34) can be solved for the x component of the unit vector:

$$\frac{c_{tissue}^2}{8 \cdot \Delta x \cdot \sqrt{R^2 + z_f^2}} \cdot \left(t_{1n}^2 - t_{1o}^2 - \frac{4}{c_{tissue}^2} \cdot (\Delta^2 x)\right) = a_{1x} \quad (35a)$$

$$\frac{c_{tissue}^2}{8 \cdot \Delta x \cdot \sqrt{R^2 + z_f^2}} \cdot \left(t_{2n}^2 - t_{2o}^2 - \frac{4}{c_{tissue}^2} \cdot (\Delta^2 x)\right) = a_{2x} \quad (35b)$$

$$\frac{c_{tissue}^2}{8 \cdot \Delta x \cdot \sqrt{R^2 + z_f^2}} \cdot \left(t_{3n}^2 - t_{3o}^2 - \frac{4}{c_{tissue}^2} \cdot (\Delta^2 x)\right) = a_{3x} \quad (35c)$$

Equations (35a), (35b) and (35c) show how the x components can easily be calculated from the acquired data. By making many $\Delta x$ movements, an average and standard deviation of $a_{1x}$, $a_{2x}$, and $a_{3x}$ can be calculated. A similar approach can be done to calculate $a_{iy}$ and $a_{iz}$. This technique is also not limited to the number of transducers in the system.

In order to show the advantages using the calibration procedure, data from a 4 MHz piston was acquired at 0 degrees, 120 degrees and 240 degrees along an approximately 40 mm radius. The piston was coupled into an agar phantom set on a three dimensional motion stage. The phantom was separately moved in x, y and z in 0.25 mm increments.

For the mechanical system, the directional matrix can be calculated as in Table 1.

TABLE 1

Calculated original a direction matrix.

| X | Y | Z | Magnitude |
|---|---|---|-----------|
| −0.707 | 0.000 | 0.707 | 1.000 |
| 0.354 | −0.612 | 0.707 | 1.000 |
| 0.354 | 0.612 | 0.707 | 1.000 |

Figure 25:
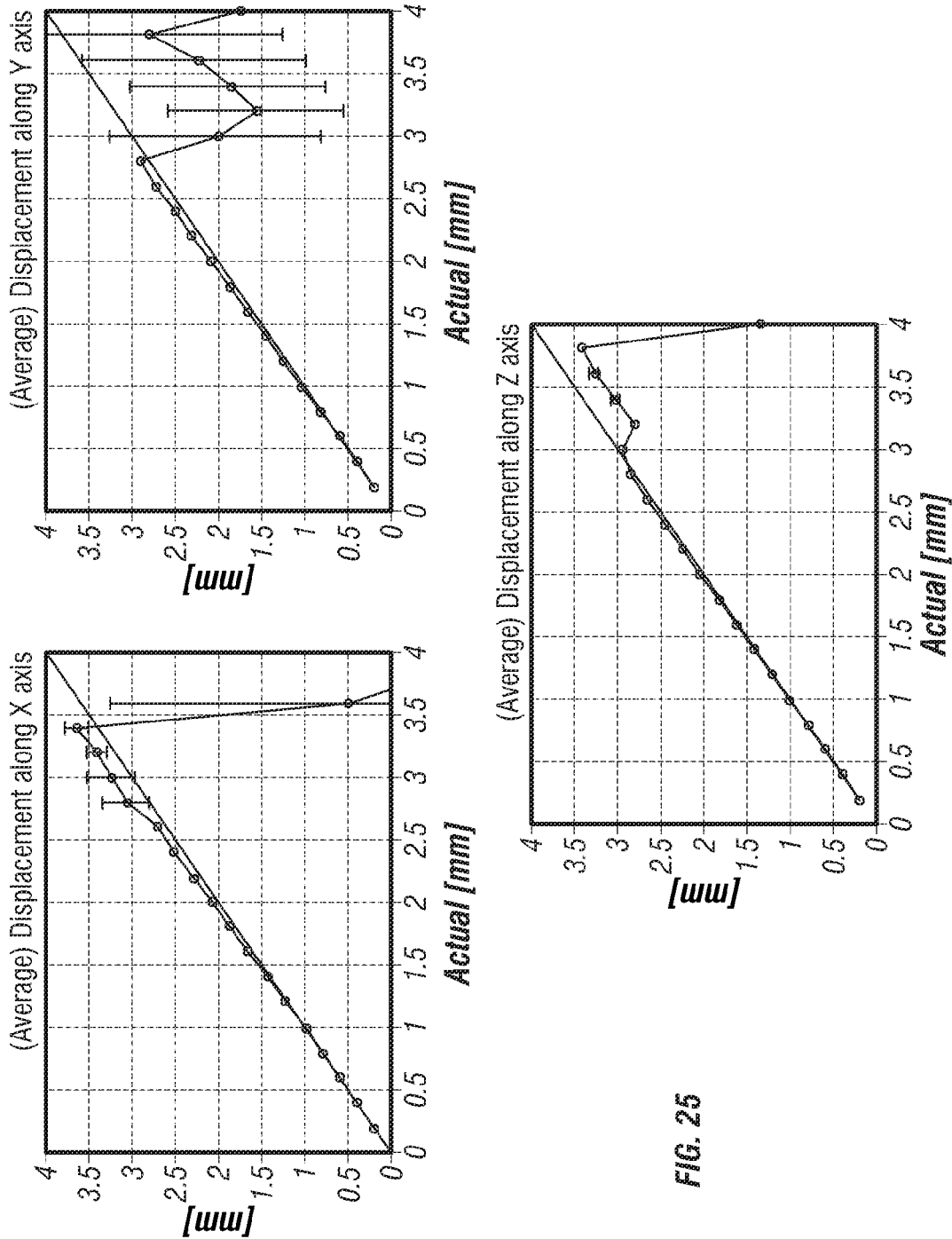
FIG. 25 depicts three graphs showing the accuracy of station keeping detected movement using a calculated direction matrix along the X-axis, Y-axis, and Z-axis, respectively.

FIG. 25 depicts three graphs showing the correlation between actual position and that determined using the algorithm described above for X, Y, and Z coordinates, respectively. The ideal result of one-to-one correlation is plotted as a line of slope 1. The distances determined using the algorithm are plotted as points. The error increases for large movements.

If the directional matrix is calculated using equations 35a, 35b and 35c, then the directional matrix is as indicated in Table 2.

TABLE 2

Measured a direction matrix.

| X | Y | Z | Magnitude |
|---|---|---|-----------|
| −0.7315 | 0.0116 | 0.8836 | 1.147 |
| 0.3638 | −0.6372 | 0.6468 | 0.978 |
| 0.3908 | 0.6218 | 0.6487 | 0.980 |

Figure 26:
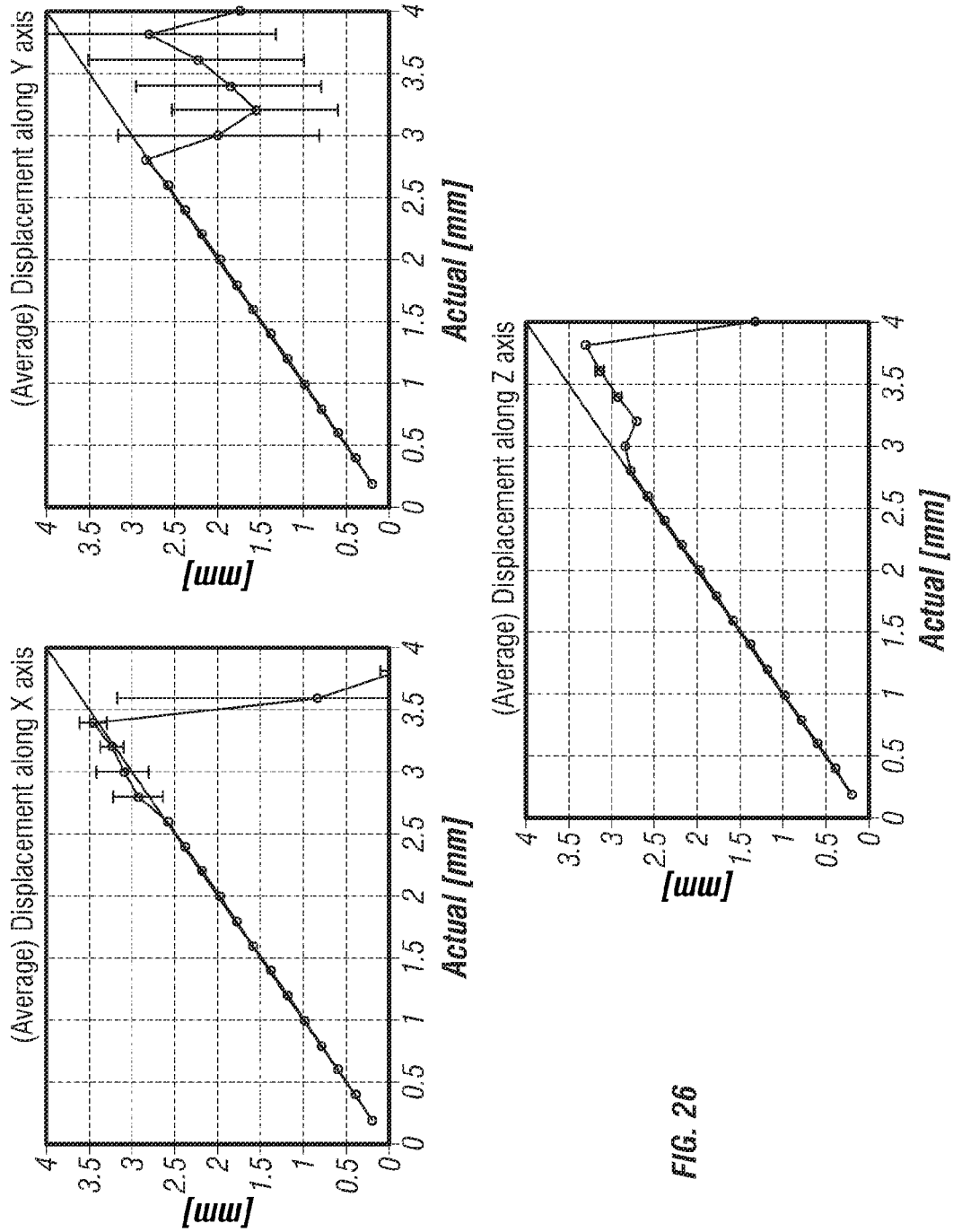
FIG. 26 depicts three graphs showing the accuracy of station keeping detected movement using a measured direction matrix along the X-axis, Y-axis, and Z-axis, respectively.

Table 2 shows that the magnitude is not necessarily equal to one and the components are significantly different than the mechanical predictions. FIG. 26 depicts three graphs showing that by using the Table 2 matrix, the algorithm results in improved tracking of movement. For example, a 1 mm movement in the x dimension is measured as a movement of over 1.05 mm using the standard mechanically determined directional matrix (FIG. 25), an error of over 5%. However, if the unit vector components are calculated, then a 1 mm movement is measured to be 1.00 mm with an error of less than 1% (FIG. 26). The significant reduction in error reduces the possibility of accumulation error when re-referencing occurs.

Some embodiments include a station keeping system for executing the procedures described above. The system may include multiple transducers, analog transmit and receive channels, an optional transmit and receive beamformer, an optional multiplexer, an analog to digital board, a CPU and memory, and an electronic compass. In some embodiments, the system provides for the measurement of six degrees of freedom to uniquely identify any point in space. In some embodiments, the system is configured to provide multiple solutions by tracking a point and calculating the effects due to translation and rotation. In addition, in some embodiments, the system provide for minimization of re-referencing by storing previous reference data with the x, y and z locations Generally, using ultrasound for station keeping is not sensitive to azimuth rotation unless multiple points in a plane are tracked. Accordingly, in some embodiments, another technique may be used to acquire the azimuth, elevation and roll angles of the applicator at the beginning of motion estimation as well as for future data acquisition.

Figure 27:
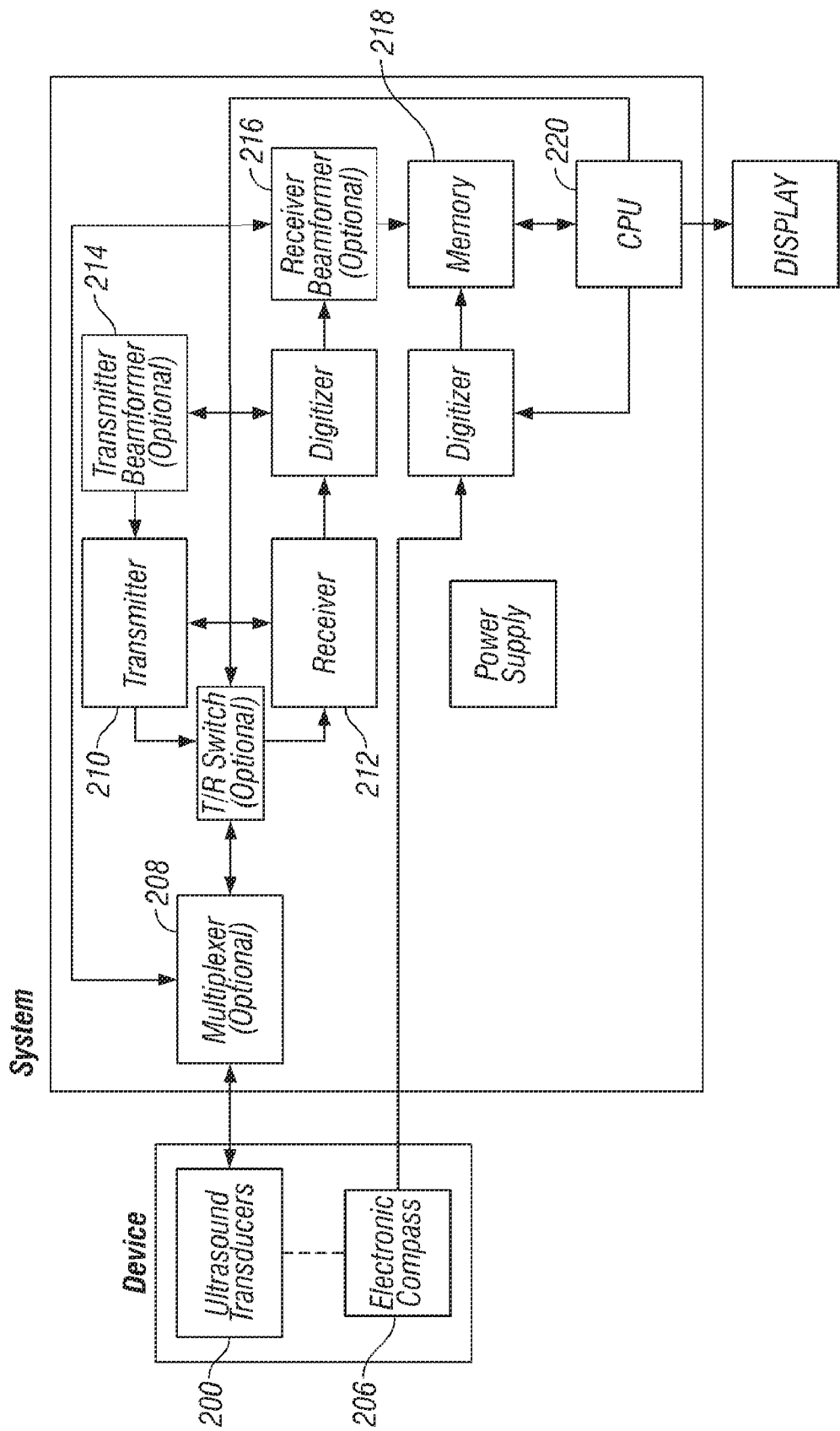
FIG. 27 is a block diagram showing a station keeping system.
Figure 28:
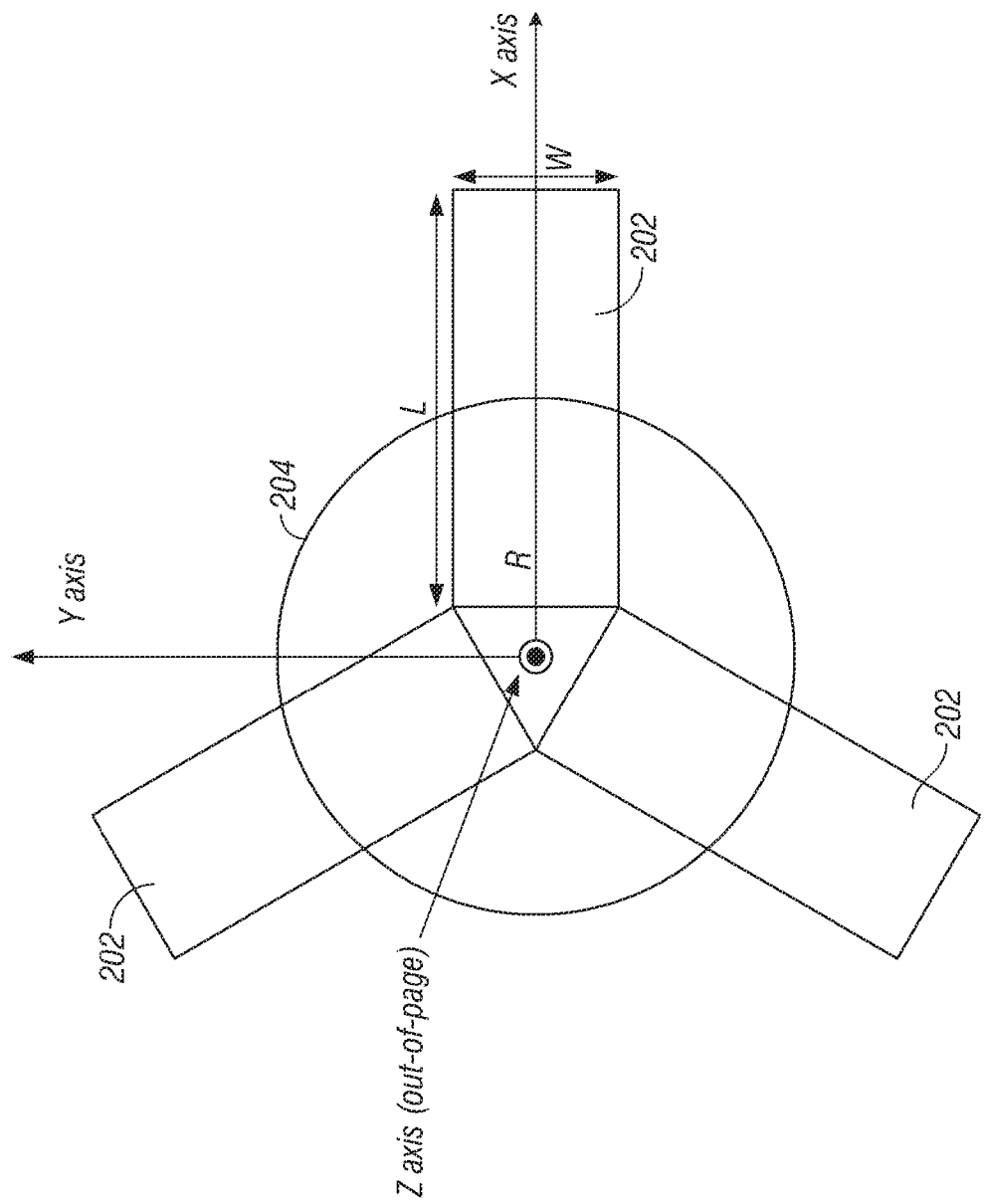
FIG. 28 is a schematic depicting a transucer concept that uses three phased arrays to track multiple points along the z-axis.

FIG. 27 shows a block diagram of one embodiment of a motion estimation system. The ultrasound transducers 200 include at least three separate transducers that are able to point at a common point. The transducers 200 can include pistons, linear arrays, 1.5-D arrays as well as 2-D arrays. For example, in one embodiment, three phased arrays 202 can be used to focus at multiple points along a central line (e.g., the Z axis) as shown in FIG. 28. In this case, the center of each phased array 202 is a distance 'R' from the origin of the x-y coordinate system. The phased arrays 202 have length 'L' and width 'W' with the imaging plane bisecting the circle 204 of radius 'R'. Therefore, the phased arrays 202 track identical points along the z-axis (out-of-the-paper). In another embodiment, the transducers may consist only of pistons that are mechanically pointed to a common point. This reduces the system complexity since each piston represents only one channel.

Referring back to FIG. 27, mechanically attached to the transducers 200 (dashed line) is an electronic compass 206 that determines the rotation of the device prior to and during the motion estimation. This includes azimuth, elevation and roll. The compass 206 is used to properly track the x, y and z movement in the coordinate system of the device away from a target.

Figure 29:
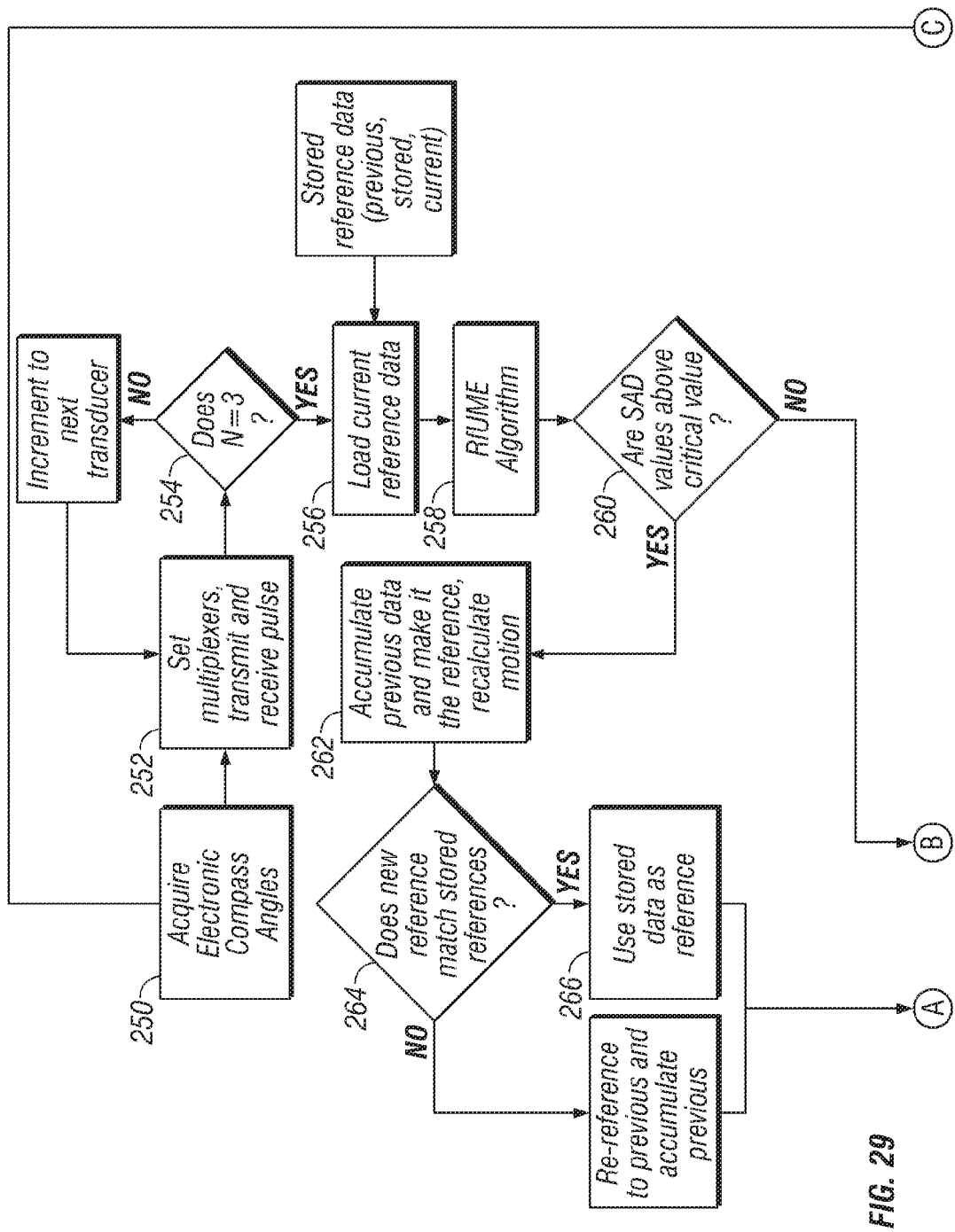
FIG. 29 is a flow chart depicting a Radio Frequency Ultrasound Motion Estimate algorithm for station keeping.
Figure 29:
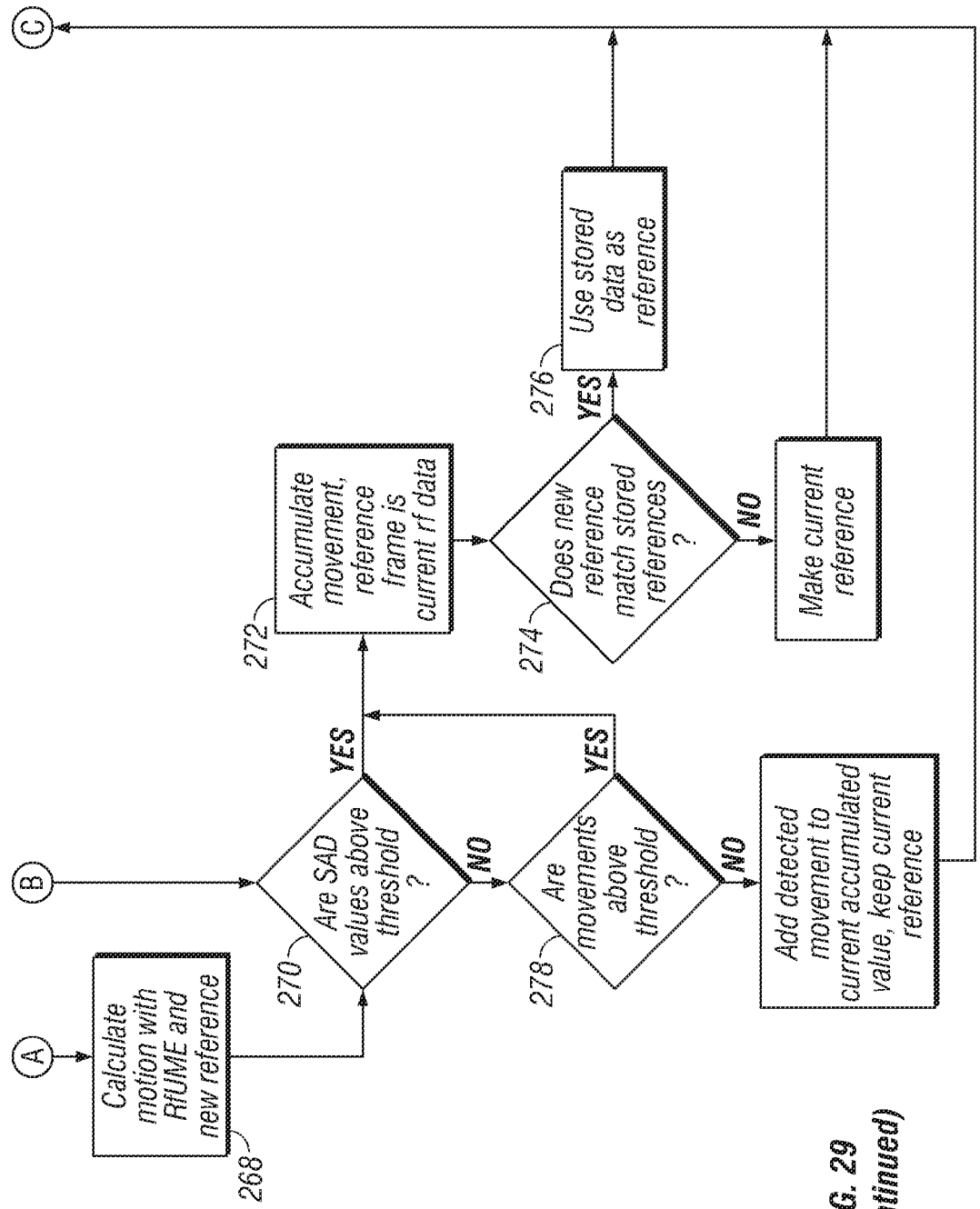

A multiplexer 208 may be optionally included if the number of transmit and receive channels is to be limited, for example, if the phased arrays in FIG. 29 consist of 32 elements each. If a multiplexer 208 is not used, a minimum of 96 transmitters and 96 receivers may be used to address each element. However, if a 3:1 multiplexer is used, then only 32 transmit and 32 receive channels are required, thereby reducing overall cost.

The transmitter 210 may include a high voltage switch that excites the transducer elements 200. Ideally, both positive and negative voltages are available. Any available spectral shaping may also be beneficial to optimizing the transmit pulse. The receiver 212 may include a preamplifier, filters, and other signal conditioning circuits prior to digitization.

Both the transmitter 210 and receiver 212 have an optional beamformer. The transmit beamformer 214 has only one delay profile per transmit event whereas the receive beamformer 216 is digital and allows beamforming at multiple depths. A memory device 218 stores the digitized signal from each transducer. The number of signals stored per acquisition is equivalent to the number of transducers in the device. The memory 218 may also save previous reference frame information. The information from the electronic compass 206 is also digitized for each acquisition and stored in memory 218.

The CPU 220 orchestrates the timing throughout the system and places the components in specific states. The CPU 220 also executes the tracking algorithm.

FIG. 29 describes the process flow chart that may be used to acquire a signal data set and estimate the motion. It is assumed that a reference signal data set has been acquired. The process flow chart can be split into two separate regions. The first is the acquisition area and the second is the algorithm. When the process is coded, a producer (acquisition)—consumer (calculation) model may be used to limit complexity and optimize processing time.

On the acquisition side, the first step (block 250) is to acquire the azimuth, elevation and roll angles from the electronic compass. These angles are used to calculate the distance moved relative to the current reference frame and ultimately the starting location. It is beneficial to use averaging or other filtering techniques that remove any acceleration components.

Next, at block 252, the signal vectors are acquired from the transducers in either a pulse-echo or pitch-catch mode. It may be necessary to reset the multiplexers depending on the system hardware configuration for each transmit. Signal data may be acquired at multiple locations or averaged to reduce phase error. This step is repeated through decision block 254 until the signal pulses from each transducer are acquired. In the embodiment depicted in FIG. 29, the number of transducers is 3, however, more transducers may be used since redundancy decreases the possibility of error.

After the current signal vectors are acquired, the signal vectors from the current reference frame are recalled from memory at block 256 and passed to the RfUME (Radio Frequency Ultrasound Motion Estimate) algorithm, which operates at block 258. The RfUME algorithm finds the phase change between the current signal vectors and the reference frame. A correlation technique such as sum of absolute differences (SAD) may be used to find the best match for each vector pair. This time difference is used in the RfUME algorithm to calculate the total movement in x, y and z from the reference. Along with the movement, the RfUME algorithm assesses the quality of the fit. If SAD is used to determine the best fit, a higher SAD value implies a lower quality fit. A histogram analysis of SAD shows that the SAD magnitude predicts whether a motion estimate from the RfUME algorithm is good or bad. For example, if the SAD value is below a certain amount, then the measured phase difference for that transducer is good. If it is above a certain amount, then the measured phase difference may be good or bad. This SAD value is defined as the critical SAD.

Therefore, after the RfUME algorithm calculates the motion, the SAD values (one SAD value for each transducer) are also compared to the critical SAD at decision block 260. If the SAD values for any of the transducers are greater than the critical SAD, then this result suggests that the previous signal acquisition should have been the new reference. In this case, the previous measured x, y and z location is the accumulated movement (block 262). In order to limit re-referencing which may accumulate a significant amount of error, the accumulated x, y and z location of the possible new reference is compared with all of the stored references at decision block 264. If the accumulated x, y and z position is near an old reference and the SAD values are acceptable, then instead of using a new reference, an old reference is used at block 266. This technique may be beneficial when trying to hold the device still and re-referencing error must be limited.

Regardless of whether a new reference or stored reference is used, the RfUME algorithm may be used at block 268 to calculate the movement and SAD values. Next, the SAD values may be compared to a SAD threshold at decision block 270. This threshold is dependent on the sample rate of the process flow chart as well as the user model. For example, the higher the sample rate, the closer the SAD threshold could be to the critical SAD value. Furthermore, the faster a user might move given a fixed sample rate, then the lower the SAD threshold. SAD threshold prevents loss of tracking ability by updating the reference frame at an acceptable rate. Therefore, if the SAD values are greater than the SAD threshold, the calculated x, y and z location is the accumulated movement and the current signal data becomes the new reference at block 272. Again, to limit the amount of re-referencing, the accumulated x, y and z position are compared to the stored reference positions at decision block 274. If there is a close match and the SAD values are acceptable, then the stored reference is used rather than the newly acquired signal vectors at block 276.

After the critical SAD and threshold SAD are tested, the amount of movement is compared to movement thresholds at decision block 278. These thresholds for x, y and z are based on the transducer position and performance. For example, the wider the beam response for the individual transducers, the longer the distances that can be tracked from the reference frame. Furthermore, the directional matrix, frequency and bandwidth also affect the tracking performance. If these movement thresholds are exceeded, then the movement is accumulated and the reference vectors are changed at block 272. This process continues until it is no longer desired to track motion.

In the RfUME algorithm, the recursive solution is used to track translation as well as rotation. In other words, movement from the reference position includes both translation and rotation (Equations 36a-36c).

$$x_{total}=x_{rotation}+x_{translation} \quad (36a)$$

$$y_{total}=y_{rotation}+y_{translation} \quad (36b)$$

$$z_{total}=z_{rotation}+z_{translation} \quad (36c)$$

RfUME only tracks the movement from the current reference frame. Therefore, it is possible to rotate between the current reference frame and the old reference frame such that the coordinate system axes are different. The electronic compass helps account for this difference. The general equation is:

$$X_{i0}=X_{k0}+S_{k0}^{-1} \cdot X_{ik} \quad (37)$$

where $X_{i0}$ is the distance from original reference to the current position, $X_{k0}$ is accumulated distance from the original reference to the current reference, $S_{k0}$ is the rotation matrix (3×3) between the current reference and the original reference, $X_{ik}$ is the distance measured with the RfUME algorithm from the current reference to the current sample. The rotation matrix is determined by the electronic compass and calibration to the ultrasound transducer is required. In order to display the net movement, $X_{i0}$ must be multiplied by the negative of $S_{i0}$, which is the rotation matrix between the current sample and the original reference.

It is also possible to obtain the azimuth, elevation and roll angles with the RfUME algorithm. This is accomplished by calculating the distance from multiple points in tissue. For example, if multiple points are tracked along the z-axis for the transducer concept depicted in FIG. 28, then the tip and tilt can be determined. Azimuth may be determined by tracking multiple points in a plane parallel to the transducer face.

Figure 7G:
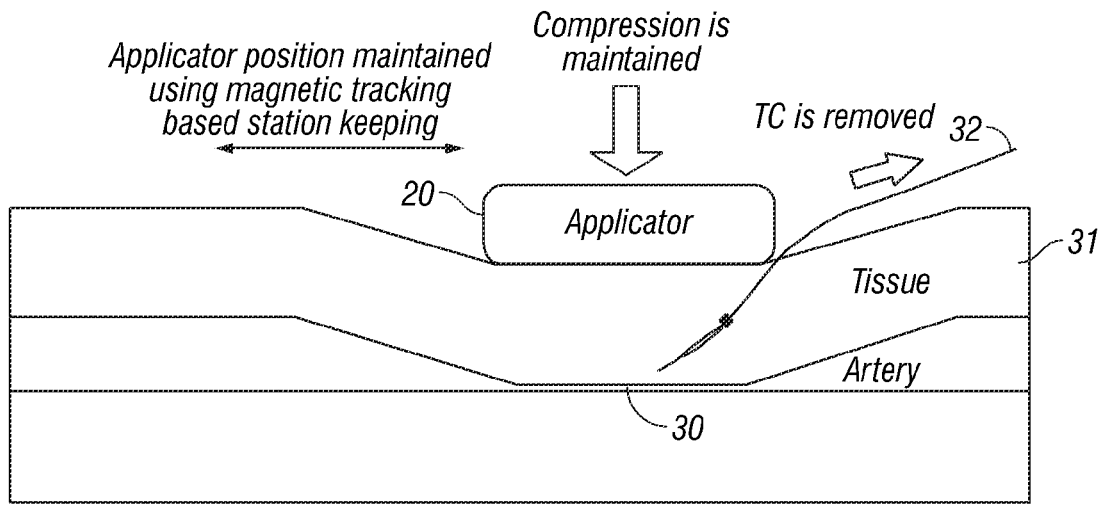
FIG. 7G is a diagram of the vascular closure procedure illustrating the withdrawal of the targeting catheter from the artery.

Returning to the discussion of the flowchart in FIG. 5, after initiating station keeping, the targeting catheter may be withdrawn at block 112. As previously noted, acoustic arterial hemostasis is more effective without the presence of a catheter, guidewire or other structure present at the arteriotomy. Thus, the targeting catheter 32 may be completely withdrawn from the patient as illustrated in FIG. 7G while the user keeps the compression of the therapeutic applicator 20 constant and keeps the arteriotomy 30 targeted within the focus of the therapeutic applicator 20 via station keeping. The user interface on the applicator 20 may provide feedback to the user to aid in maintaining optimal compression and station keeping.

Figure 7H:
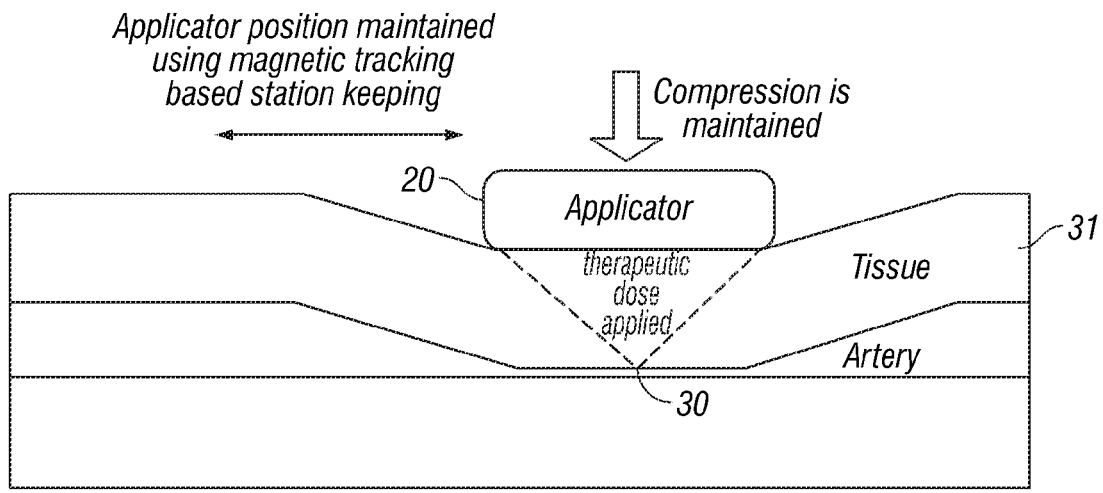
FIG. 7H is a diagram of the vascular closure procedure illustrating the dosing of the focused ultrasound in order to perform acoustic arterial hemostasis.

Finally, at block 114 of the flow chart in FIG. 5, therapeutic energy may be applied from the applicator to cause hemostasis. The treatment depth and dose may be automatically calculated and administered after hemostatic compression and arteriotomy targeting are achieved and the targeting catheter has been withdrawn. FIG. 7H illustrates an energized ultrasonic therapeutic applicator 20 delivering a focused ultrasound beam near the arteriotomy 30. The partial absorbance of the ultrasound energy by the tissue 31 at the focus of the beam causes rapid heating of the tissue 31 near the arteriotomy 30. Without being bound by any particular theory or mode of action, it is believed that the heat denatures the native perivascular collagen with subsequent formation of an extensive fibrin network that covers the arteriotomy 30, thereby sealing it closed. The duration of therapy may be any suitable period sufficient to effect hemostasis. In some embodiments, a continuous application of therapeutic energy is used. In other embodiments, the application of therapeutic energy may be interrupted, for example to allow interim cooling or repositioning of the therapeutic energy applicator 20. The ultrasound treatment dose in one embodiment takes approximately 60 seconds.

Figure 30:
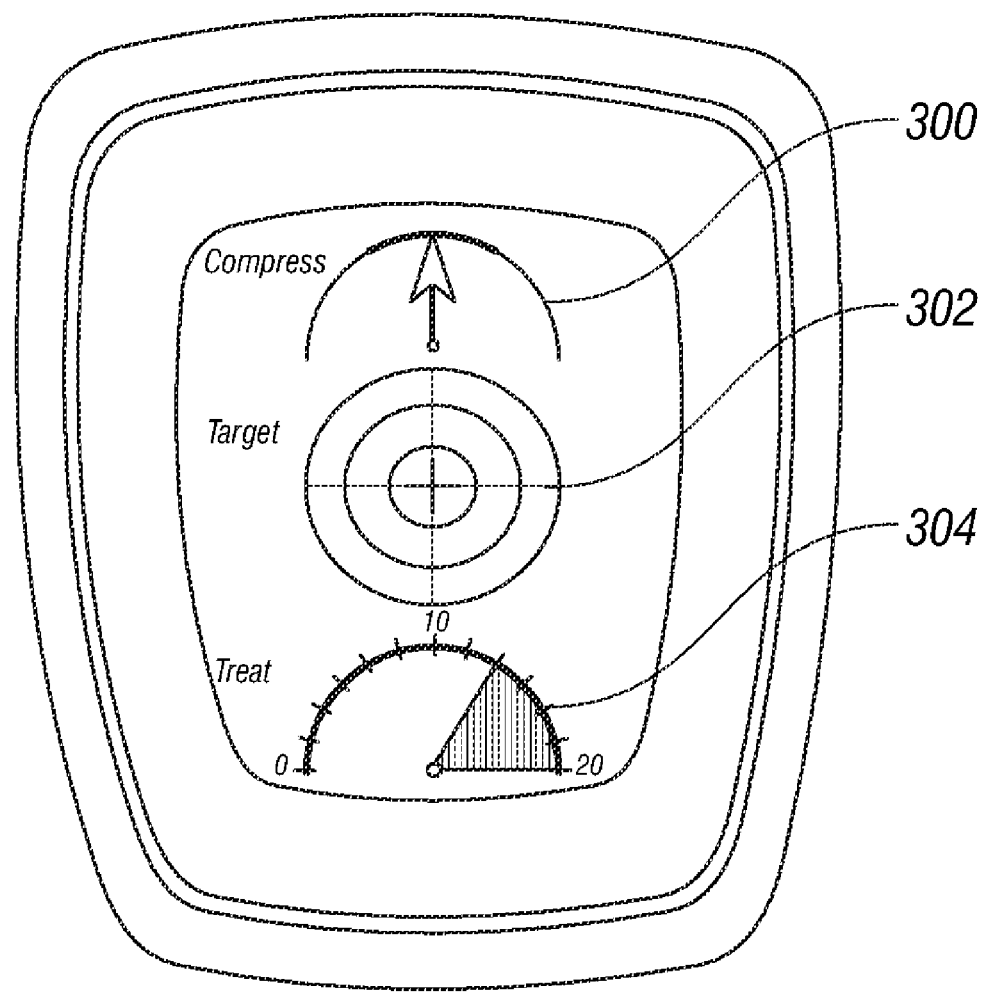
FIG. 30 is an illustration of an ultrasound applicator user interface during therapeutic dosing.

As depicted in FIG. 30, during this dosing period, the user interface located on the therapeutic applicator may display relevant information such as the amount of compression 300, a targeting display 302 for keeping the ultrasound focused on the arteriotomy, as well as a count down clock 304 indicating when treatment will terminate. Upon completion of the dosing, a short period of tissue cooling may be allowed to occur without compression or applicator position being changed. Subsequently, the treatment may be concluded by the therapeutic applicator being removed from the patient's skin.

As described above, the targeting catheter may be used to locate the precise position of the arteriotomy, such as by use of a targeting aid (e.g., an inflatable balloon) located on the targeting catheter. As note above, suitable targeting aids are not limited to balloons but may include one or more arteriotomy locating sensor(s). Suitable arteriotomy locating sensor(s) include but are not limited to: i) acoustic transceivers capable of transmitting and receiving acoustic signals (such as Doppler), ii) self-heated thermistor-based probes for detecting the arteriotomy location by discriminating conductive and convective energy dissipation levels in the tissues and blood surrounding the probe, and iii) use of piezoelectric materials self heating characteristics to discriminate conductive and convective energy dissipation levels in tissues and blood surrounding the probe. Additional descriptions for these three arteriotomy detection techniques are provided below. Those of skill in the art will appreciate many other possible methods and sensors for determining whether a sensor (or arbitrary location on a catheter) is located within a blood vessel versus or within tissue.

Figure 31:
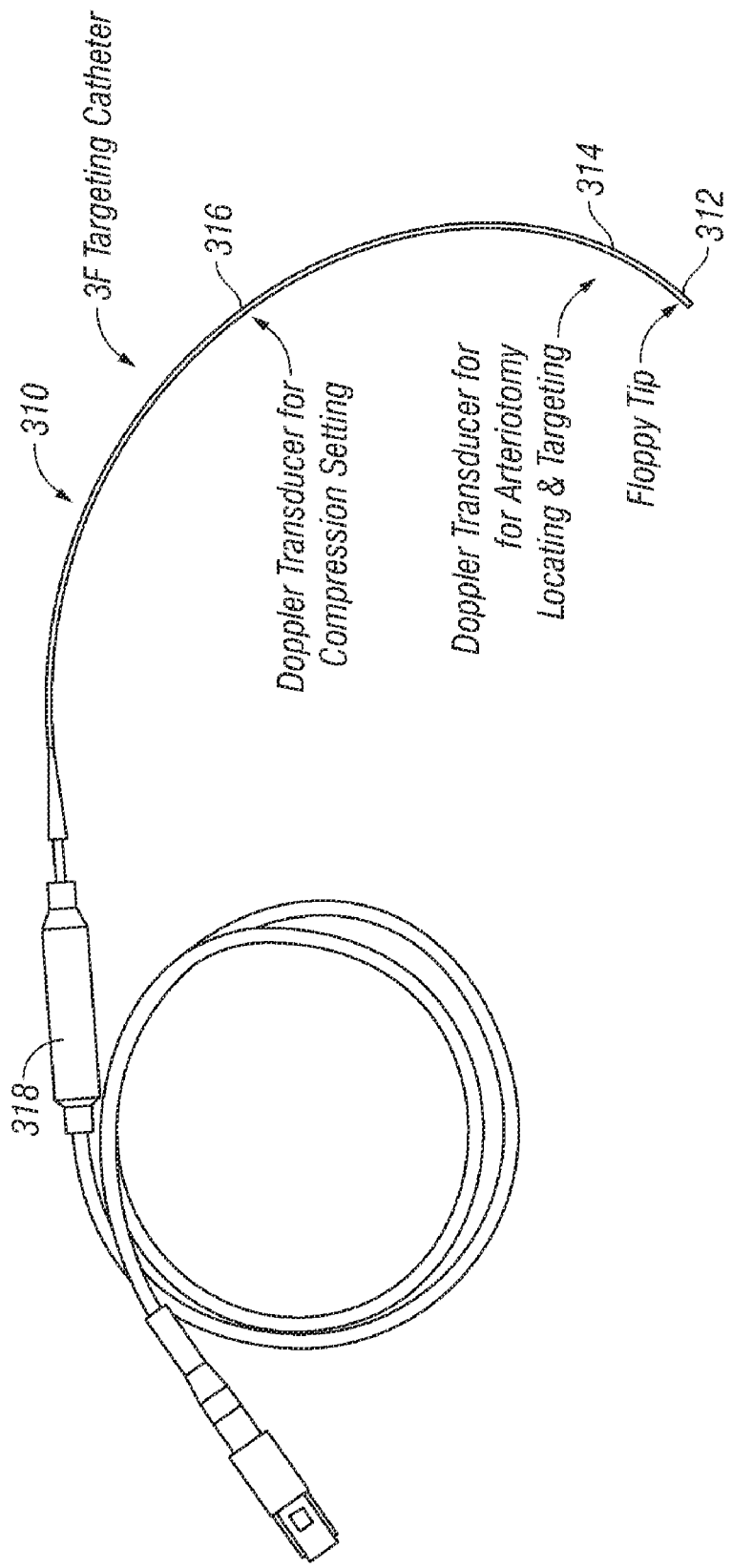
FIG. 31 is an illustration of a targeting catheter having a piezoelectric Doppler device as a targeting aid.

One example of arteriotomy locating sensor(s) includes one or more Doppler transducers as illustrated in the targeting catheter 310 depicted in FIG. 31. This targeting catheter 310 has a soft flexible tip 312 with one or more locating and targeting piezoelectric Doppler devices 314. Further up the catheter 310 is a Doppler compression sensor 316 and a hub 318 located at the terminal end of the catheter 310. Within the hub 318 is a tuning (matching) circuit and a mechanical and electrical connector allowing the targeting catheter 310 to be mechanically and electrically connected to the control system hardware.

The arteriotomy localization step may be accomplished by slowly withdrawing the targeting catheter, thereby causing the arteriotomy locating sensor(s) (e.g., Doppler devices 314) to get closer to the arteriotomy. The sensor signal is monitored to determine when the arteriotomy locating sensor is proximate to the arteriotomy. In one embodiment, the Doppler transducer(s) 314 may also emit an ultrasound signal which is received by ultrasound receivers or transducers located on the applicator to monitor the movement and position of the Doppler transducer(s) 314, such as by using ATOF as described above.

Figure 32:
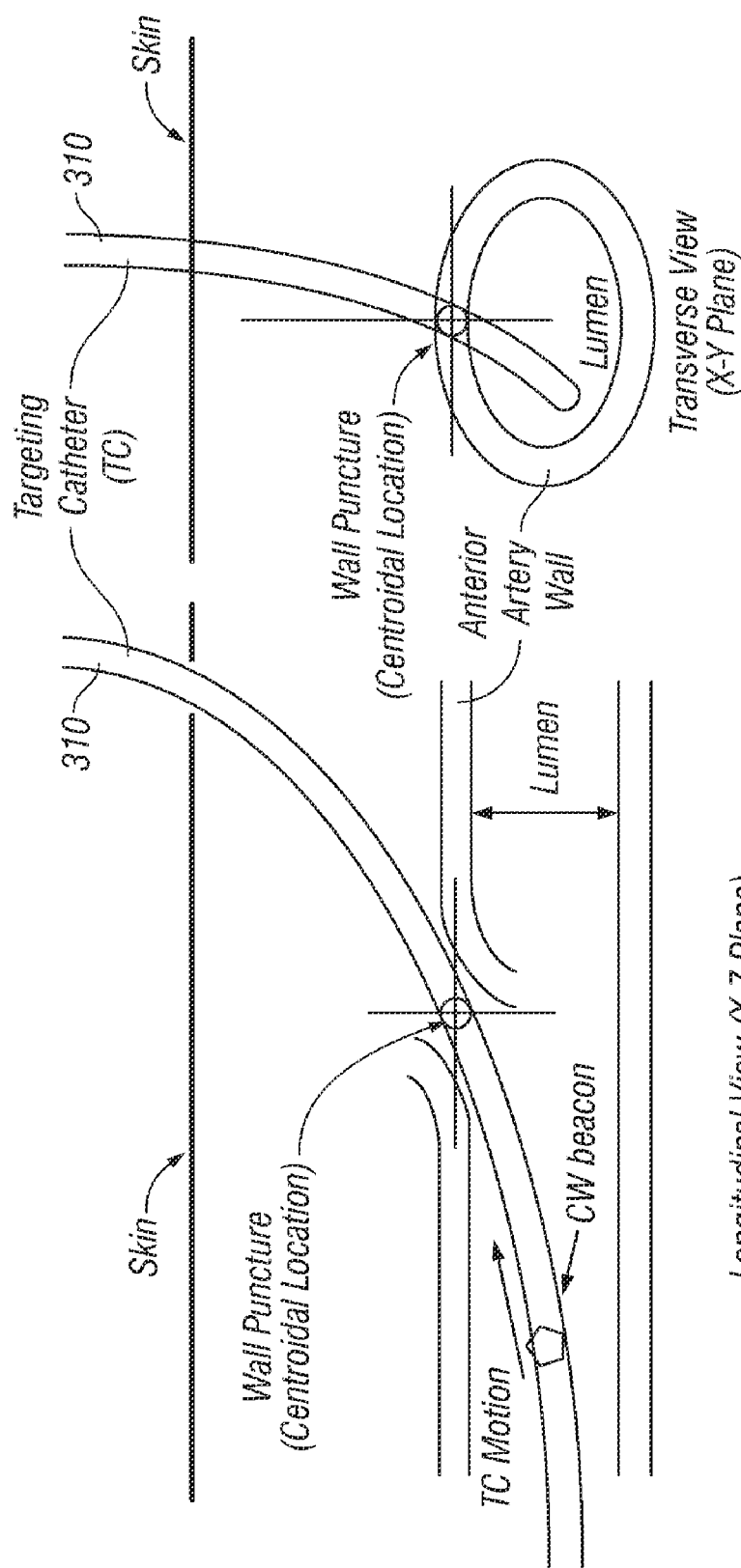
FIG. 32 is a schematic of a targeting catheter located in a femoral artery.

FIG. 32 is a schematic illustrating one embodiment of a procedure that may be used for arteriotomy localization (AL) using the catheter depicted in FIG. 31. In this illustration, the Doppler transducer is referred to as a "CW beacon." In one embodiment, the targeting catheter 310 has a flexible construction to minimally distort the vessel position relative to the therapeutic applicator during targeting. Thus, in one embodiment, as depicted in FIG. 31, it is preferred that the AL positioning is accomplished only through pulling (i.e., not pushing). This pulling may be accomplished by a withdrawal motion using either continuous movement or discrete incremental pulls. Pulling may be accomplished through either a manual process or by a device implementing a controlled pull process of the targeting catheter 310. The speed and force associated with the targeting catheter 310 withdrawal maneuver to achieve the AL position may allow for clinically practical manual dexterity and a reasonable time for AL positioning, especially when using manual pulling. In one embodiment AL position takes only several seconds. In an alternative embodiment, a targeting catheter 310 may be used that is stiff enough to be both pushed and pulled into the arteriotomy locating position.

Figure 33A:
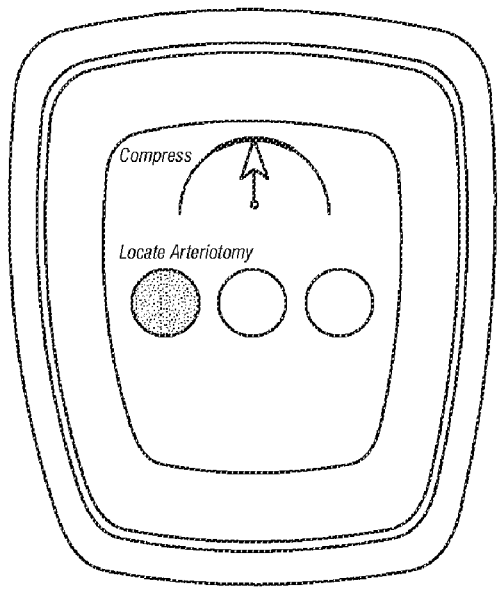
FIGS. 33A-33C are illustrations of a user interface on the therapeutic applicator.
Figure 33B:
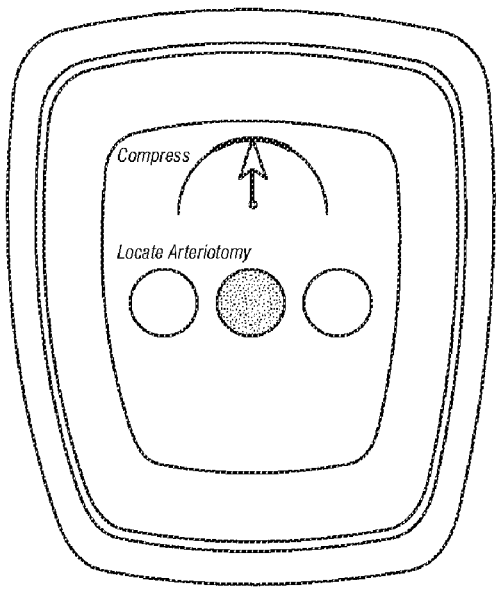
Figure 33C:
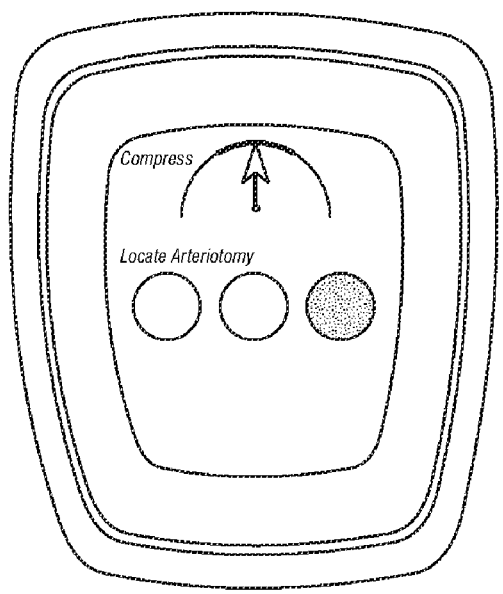

To guide the user to achieve accurate arteriotomy localization placement, specific vascular locations may be detected by the arteriotomy location sensor (e.g., Doppler transducer(s)) using an algorithm subsystem. Upon detection, this information may be translated into feedback presented to the user through the user interface located on the display of the handheld therapeutic applicator. In one embodiment, depicted in FIGS. 33A-33C, a "Green Light/Yellow Light/Red Light" display may be utilized. After the targeting catheter has initially begun to be withdrawn, the arteriotomy locating subsystem can detect the ateriotomy locating sensor (e.g., Doppler transducer(s)) passing into the "treatment volume," defined approximately by the tissue cylinder having as it's top surface the footprint of the therapeutic applicator. At this point, the user interface may display a "Green Light" (FIG. 33A) to indicate to the user that the beacon has crossed into the treatment region. While the user is pulling in the "Green Light" state, the pull velocity can be monitored via ATOF and, via communication with the ATOF system, the AL algorithms can detect beacon withdrawal velocities that may be too high (e.g., >3 mm/sec). Upon exceeding this velocity limit, the AL algorithm can trigger the user interface to alert the user to slow down the withdrawal speed if the user is using manual pulling. Once the AL subsystem detects the arteriotomy location sensor (e.g., Doppler transducer(s)) as having reached an arteriotomy "proximity zone", defined, for example, as 8 mm from the arteriotomy along the targeting catheter track, the status light will change to "Yellow" on the user interface to alert the user to slow down the withdrawal speed, as shown in FIG. 33B. The ATOF system can be used to monitor the withdrawal speed and alert the user to slow down if the speed exceeds an appropriate value relevant to the proximity zone, for example, 1.5 mm/sec. Once the AL subsystem detects the arteriotomy location sensor(s) (e.g., Doppler transducer(s)) as having achieved arteriotomy localization (the "AL Position"), defined as a position at or a known distance from the centroid of the arteriotomy, with a tolerance on positioning of +/−1.0 mm, the status light will change to "Red" on the user interface (as shown in FIG. 33C) to alert the user or a targeting catheter puller device to stop the withdrawal of the targeting catheter.

Those of skill in the art will appreciate that other methods of providing feedback to a user to adjust the speed of catheter withdrawal may be used. For example, the actual rate of withdrawal may be displayed to the user. In addition, audible signals may employed such as tones or voice commands.

Figure 34:
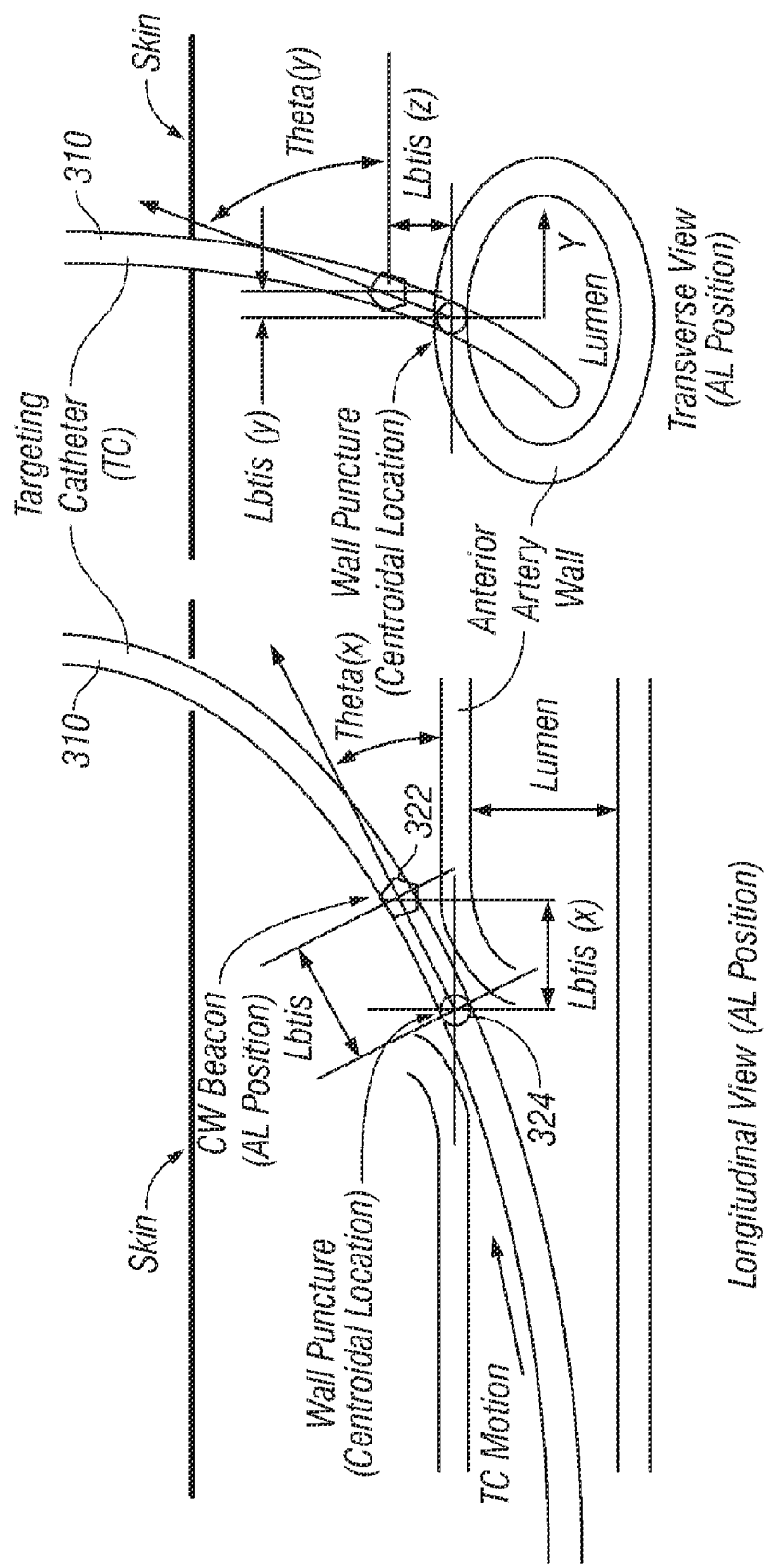
FIG. 34 is a schematic illustrating the determination of the distance between an arteriotomy and a beacon/arteriotomy sensor.

FIG. 34 is a schematic depicting the withdrawal of the targeting catheter 310. The spatial relationship of the arteriotomy locating sensor 322 (e.g., Doppler transducer(s)) relative to the arteriotomy when at the arteriotomy localization position can be described by the distance vector, $L_{btis}$, that describes the distance between the arteriotomy locating sensor 322 and the centroid 324 of the puncture site along the path of the targeting catheter and puncture track as shown in FIG. 34. The centroid 324 of the arteriotomy is defined as the intersection of the targeting catheter 310 axis and the middle of the femoral artery wall at the puncture. If $L_{btis}$ has a positive value, the arteriotomy locating sensor 322 (e.g., Doppler transducer(s)) is positioned in the tissue track, whereas, if $L_{btis}$ is negative the arteriotomy locating sensor 322 (e.g., Doppler transducer(s)) is within the artery lumen. If $L_{btis}$=0.0 the arteriotomy locating sensor 322 (e.g., Doppler transducer(s)) resides precisely at the centroid 324 of the puncture site.

As shown in FIGS. 32 and 34, the arteriotomy locating sensor may include an acoustic transducer labeled "CW Beacon" 322. The localization step may be accomplished by using the beacon 322 Doppler shift signals, as processed and interpreted by the arteriotomy localization hardware/software (a combination of system hardware and system software incorporating arterial localization specific algorithms). The "CW Beacon" 322 may transmit an acoustic signal and detect the Doppler shifted echo. The Doppler shift information is associated with motion at and near the arteriotomy, and the dominant motions yielding beacon 322 position-relevant signal information are those associated with blood flow (e.g., velocity, flow turbulence, blood flow direction relative to the beacon 322 orientation, and blood pressure variations). The Doppler processing used can either be based on non-directional or directional (In-Phase and Quadrature) modes. In addition, different frequencies can be used to excite different beacon 322 vibrational modes, modifying the tissue and spaces interrogated for Doppler shift information.

Although it is anticipated that the Doppler signals of relevance will occur in the audible portion of the spectrum, in one embodiment, the electronic system user interface is able to inform and guide the user as to beacon 322 localization through either audible or non-audible (principally visual) cues. In this way, less user training and experience will be required to achieve reliable arteriotomy localization. Localization cues that are non-audible and thus not dependent on a user learning "targeting sounds" may be generated by having the Doppler signals be processed by the arteriotomy localization hardware/software in a manner which can identify the acoustic signature of the arteriotomy or other characteristic location near the arteriotomy that has a consistent and unique acoustic signature.

Figure 35:
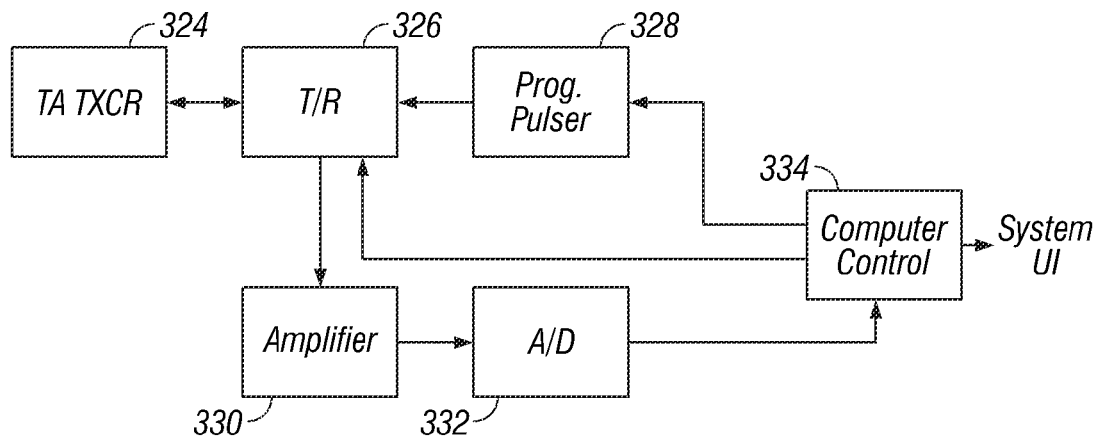
FIG. 35 is a block diagram of an arteriotomy locating system.

FIG. 35 displays one embodiment of a system that may be used for targeting catheter placement. A targeting catheter transducer ("TA TXCR") 324 may be mounted on the targeting catheter. Ultrasonic send and receive circuits ("T/R") 326 and processing may be provided by programmable pulser 328, amplifier 330, and analog to digital converter 332, through transmit/receive switch 326—all under control of a processor 334, which itself is capable of either CW or pulse wave Doppler processing (depending upon the embodiment). This exemplary processing configuration will be used as the basis for describing several approaches to targeting catheter placement below. Each approach to targeting catheter placement generally follows a process wherein the operator advances the targeting catheter into the body via an introducer sheath or entry channel and positions it in the entry channel in response to user interface information.

Figure 36:
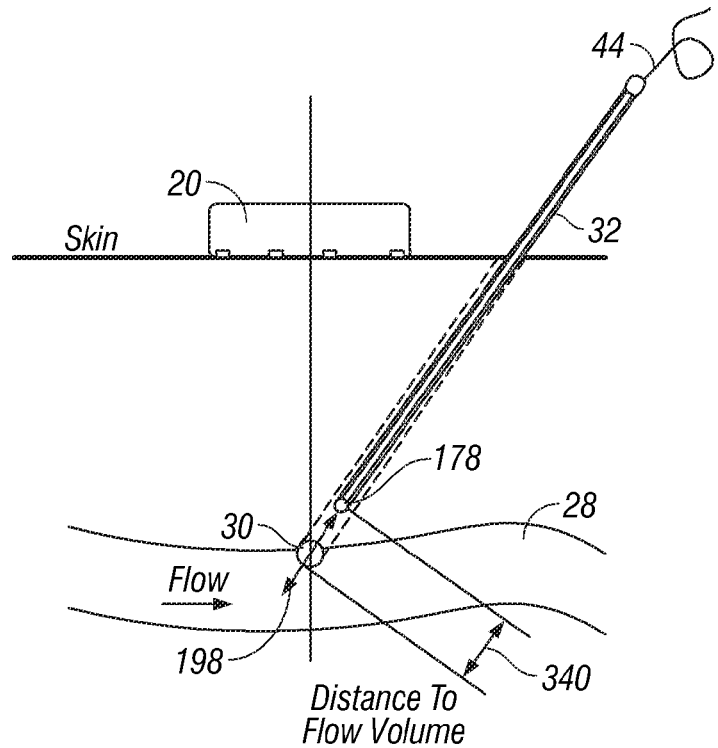
FIG. 36 is a schematic of a forward looking Doppler arteriotomy locating sensor.

Forward looking Doppler—FIG. 36 depicts the functionality of a technique employing forward looking pulsed wave Doppler to measure the distance 340 in front of the targeting catheter beacon 178 at which the arterial flow volume is located. Here, beacon 178 is pulsed at a relatively high (approximately in the range 3-8 MHz) frequency, projecting a narrow acoustic beam 198 axially and in front of beacon 178. The beacon 178 detects the Doppler shifted echo of each pulse. The computer of FIG. 35 executes range-gated analysis of the Doppler pulse, thus measuring distance to the region of blood flow, 340. The user interface can instruct the operator to position the beacon 178 at a point corresponding to the clearance location (CL), the place where the beacon 178 is located outside of the region of insonification from the therapy beam. Accordingly, in some embodiments, the targeting beacon 178 may remain in the body during application of therapy, providing desired targeting information to a user to assist the user in maintaining the focal point of the therapeutic energy at the site of the arteriotomy 30. For example, the location of the beacon 178 relative to the therapeutic applicator 20 along with the distance to flow volume 340 may be used to determine the location of the arteriotomy 30 relative to the applicator 20.

Alternatively, in systems with two (or more) beacons 178 located on the targeting catheter, the geometric uncertainty created by stick angle variation may be compensated for, assuming that an ATOF positioning system is in operation during the targeting catheter placement and location process. For example, referring to FIG. 36, the forward looking Doppler distance desired for proper positioning is defined by:

$$\text{DISTANCE TO FLOW VOLUME} = (V+Dw+F)/\sin(\alpha s) \quad \text{Eq. 38}$$

Figure 37:
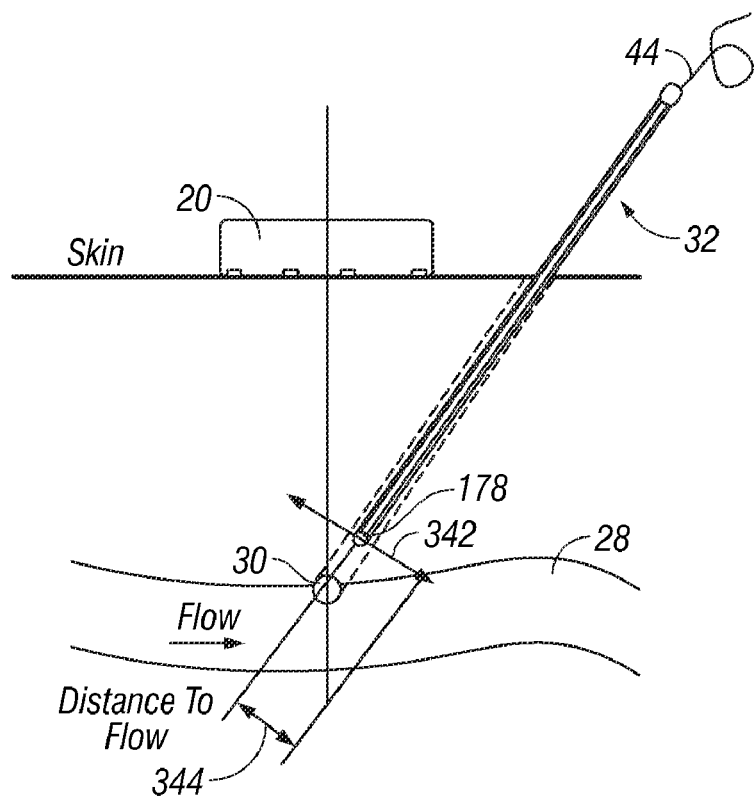
FIG. 37 is a schematic of a side looking Doppler arteriotomy locating sensor.

Side-looking Doppler—FIG. 37 illustrates another positioning alternative wherein pulsed wave Doppler transmitted in a beam 342 perpendicularly to the axis of the targeting catheter 32 locates the flow volume. In a manner similar to that employed in the forward looking Doppler technique, measurement of the distance to the flow volume 344 is made and is used as a parametric representation of the location of beacon 178 with respect to the Arteriotomy 30.

Figure 38:
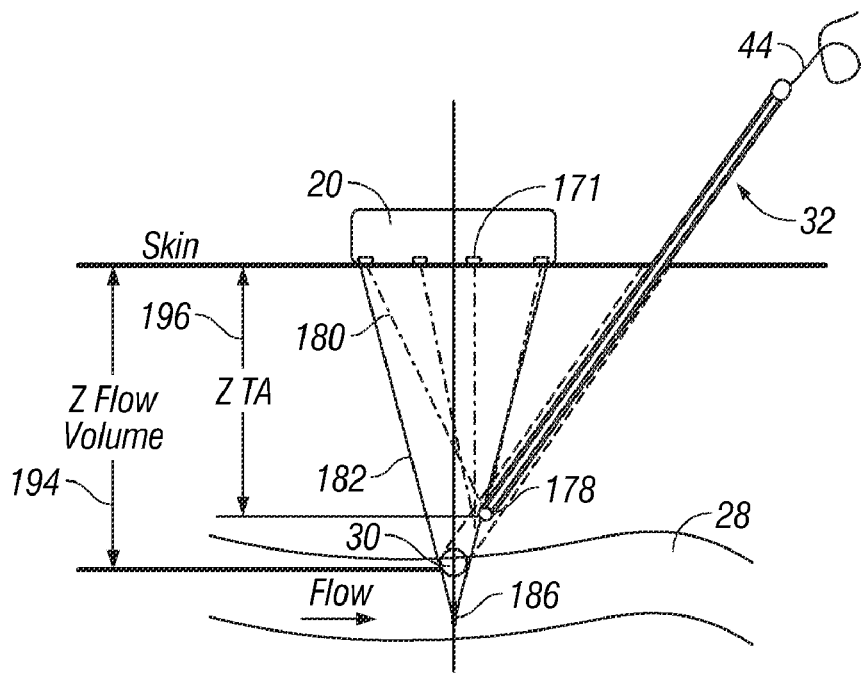
FIG. 38 is a schematic of a Z-matching arteriotomy locating sensor.

Z matching—In yet another alternative method illustrated in FIG. 38, a technique is used which locates the beacon 178 relative to the arteriotomy 30 by matching the z coordinate (depth from the applicator 20 surface positioned on the skin) of the beacon 178 to the z coordinate of the flow volume:

$$Z \text{ FLOW VOLUME} + \text{DELTA} = Z \text{ TA} \quad \text{Eq. 39}$$

where DELTA is an offset value representing the distance above the flow volume desired for beacon positioning.

In this approach, the z coordinate of the beacon 178 is measured by utilizing the ATOF triangulation system—TOF distances 180 between the beacon 178 and the receiving sensors 171 on the applicator 20. The z coordinate of the anterior surface of the flow volume (shallowest) is measured, as depicted in FIG. 38, by pulsed Doppler ranging with pulses transmitted by the therapeutic array in applicator 20 and received by beacon 178. Because the therapeutic transducer may normally operate at a small f/number, an interrogating Doppler line could be constructed from a number of transmit pulses having progressively varying focal positions. This method offers very high resolution location of the flow volume due to power available and the sharp focus.

In this technique, the applicator 20 would ideally be in targeted position when executing the Z matching because the artery 28 may be deep at various positions. An iterative method of positioning may be used wherein the applicator 20 is approximately positioned, beacon 178 is placed, and then the applicator 20 and beacon 178 are re-positioned for final targeting.

Those of skill in the art will appreciate several alternative approaches for utilizing a targeting catheter beacon 178 in combination with the sensors 171 on the therapeutic applicator 20. For example, in one embodiment, a separate Doppler transducer (one or more channels) may be integrated into the applicator 20 face and used to both send and receive.

Combination Methods—It is noted that the above methods may advantageously also be used in combinations with each other, for example, by combining forward looking and side-looking Doppler. Such combinations may be used to increase robustness of the positioning process. These methods may also be used in combination with thermal methods. It is noted that beacons on the targeting catheter may be used to make self-heated thermal measurement and associated position determinations inside or outside of flowing blood. In this method, the capacitance may be measured at an off resonant frequency of the piezoelectric material (e.g. PZT) to estimate temperature.

In some embodiments, the arteriotomy location sensor on the targeting catheter may be a thermistor based probe, used either alone or in combination with an ultrasound transducer. Use of self-heating thermistors is termed herein as Thermistor Detection via Targeting and Monitoring (TDTM). These probes contain thermistors as sensors to assist in locating the puncture site, monitoring leakage of fluids or bleeding (prior to and during treatment), confirming the targeted location of the therapeutic energy delivery, and measuring and monitoring at least a portion of the thermal dose delivered to the treatment field. In order to be inserted down the puncture track, and thus directly into the puncture wound at the vessel or body cavity, the TDTM probes may have physical structures, and sizes, similar to catheterization guidewires. They can be deployed as an integral portion of a therapeutic hemostasis procedure using either non-invasive or invasive therapeutic heating modalities, and have the advantage of requiring little additional effort or complexity in the puncture sealing or closure procedure.

The core sensor(s) deployed on the TDTM probes may be one or more thermistors (temperature sensors possessing the property of electrical resistance that varies with temperature). Both the electrical resistance variation with temperature of thermistors and their property of self-heating when supplied with adequate electrical power may be utilized. The latter property refers to the fact that when a thermistor is connected to an electrical circuit, power is dissipated in it as heat and, thus, the body temperature of the thermistor rises above the temperature of its immediate environment. An energy balance on the thermistor requires that the rate at which energy is supplied ($Q_s$) must equal the rate at which energy is lost, plus the rate at which energy is absorbed (energy storage). The rate of thermal energy delivered to the thermistor is equivalent to its electrical power dissipation, i.e., $Q_s=P=I^2R=VI$. The rate at which a thermistor's thermal energy is lost to its surroundings ($Q_L$) is proportional to the temperature difference between it and its surroundings, i.e., $Q_L=\delta(T-T_a)$, where $\delta$ is the "dissipation coefficient." The dissipation coefficient is defined as the ratio, at a specified temperature, of a change in the power dissipation of the thermistor to the resultant thermistor body temperature change. The dissipation constant depends on the thermal environment around the thermistor, so naturally, the coefficient depends on the thermal conductivity of the medium surrounding it, convection (forced or free convection) influences, as may result from relative motion between the surrounding medium and the thermistor, and thermal conduction through leads and surfaces upon which the thermistor is mounted, etc. The dissipation coefficient is also naturally dependent upon the physical geometry of the thermistor, especially its surface area and mass. For example, a larger surface area will result in a larger dissipation coefficient for a given thermal environment. This in turn requires more input power for a larger thermistor than a smaller one in order to achieve an equivalent temperature difference between the thermistor and its surroundings. The additional power requirement effectively reduces the sensitivity of the device. Furthermore, a small thermistor device will have low thermal mass, which will allow it to cool and re-heat relatively quickly. This relatively fast thermal response makes the smaller device more sensitive to rapid changes in the dissipation coefficient.

It has been found that small self-heating thermistors, when placed in the human body in medical procedures, can be used to measure tissue temperature, thermal properties, blood temperatures and, when appropriately calibrated, even blood flow levels in organs and vessels. Similar principles may be applied in detecting and discriminating levels of blood flow at and surrounding the puncture wound site, and in discriminating conduction and convective energy dissipation levels in the tissues surrounding the probe. The TDTM probe may be positioned in the tissue such that its thermistor sensor(s) can travel to and be located in close proximity to the puncture site, typically through the puncture track created by the instrument producing the puncture wound and/or maintaining the wound portal open (e.g., a catheter or needle).

Figure 39:
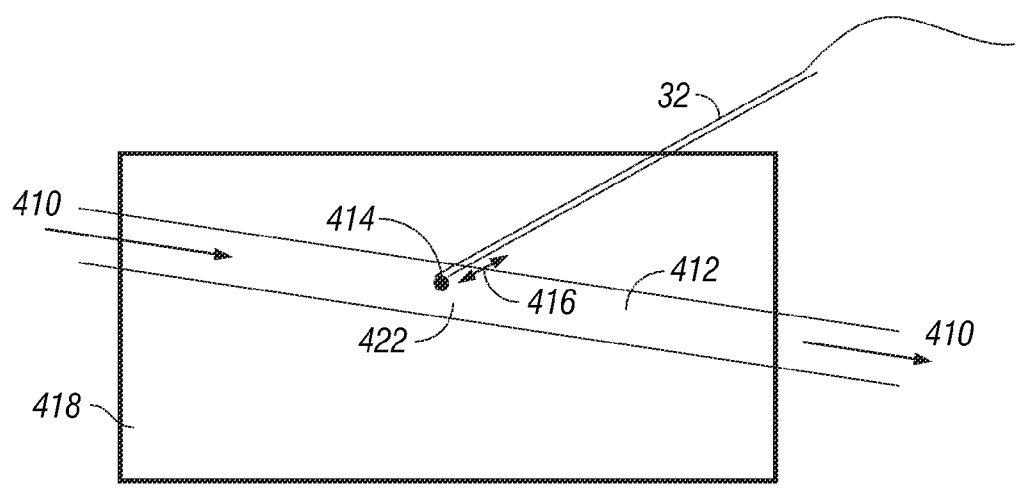
FIG. 39 is a schematic of a TDTM probe having a single thermistor at its tip.

FIG. 39 illustrates a TDTM probe having a single self-heating thermistor 414 at the tip of the targeting catheter 32 inserted into an agar tissue phantom 418 incorporating a "blood vessel" 412 (duct cast into the agar) perfused with a blood-mimicking fluid (e.g., water in thermal equilibrium with the agar) 410.

The probe 414 may be placed in the vessel 412 in a manner analogous to arterial catheterization, by creating a puncture track from the "skin" surface down to the vessel puncture site (intersection of the probe 414 with the vessel 412). By moving the probe 414 (probe 414 travel is indicated as by arrows 416) in the puncture track, such that the sensor 414 (e.g., the thermistor bead) can be alternatively placed a) in the track, b) at the anterior (upper) vessel wall (i.e., the puncture site) or c) in the lumen of the vessel 412, thermistor signals indicative of the bead location are provided as output to the data acquisition system.

Figure 40:
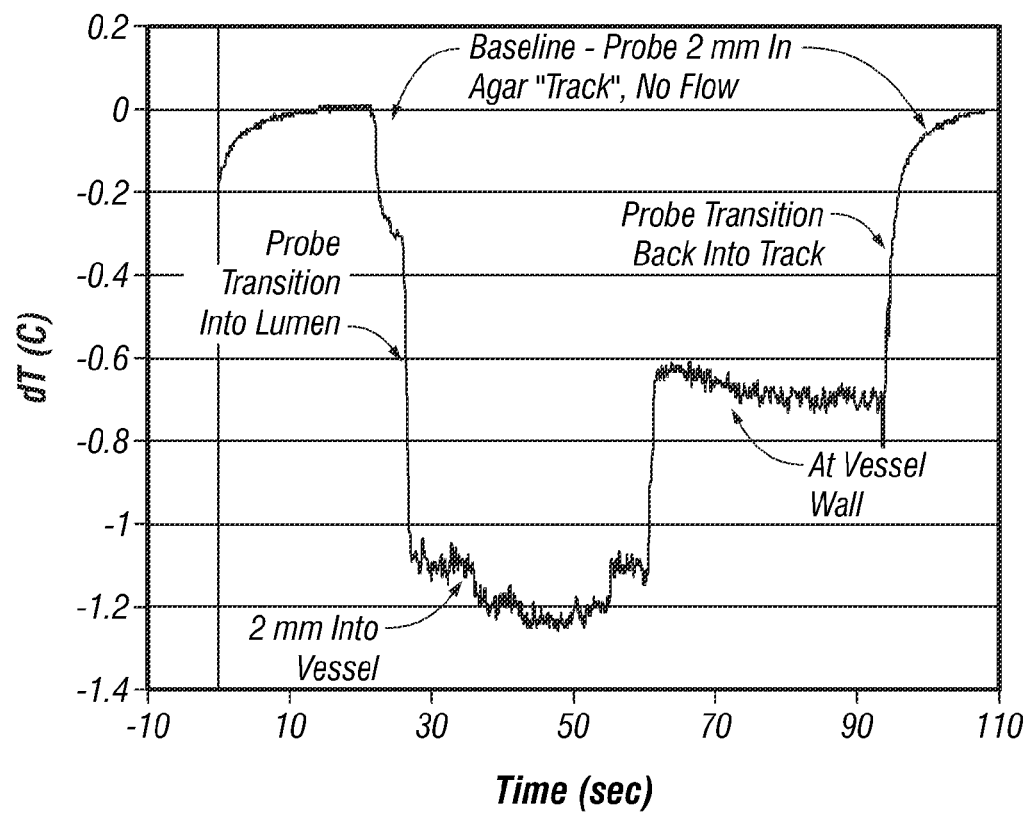
FIG. 40 is a graph of temperature signals from a thermistor bead on a TDTM probe.

FIG. 40 is a graph of temperature differential, show the variation of the differential for various locations of the probe. The thermistor may be first "zeroed" with the bead in the track (i.e., the equilibrium temperature whereby the self-heated thermistor is in the track and has no flow may be set as the baseline). After zeroing, maneuvering the probe in and out of the "vessel" will produce characteristic thermal signals indicative of the bead position. For example, as the probe bead is advanced into the lumen of the vessel, the sensor signal indicates the associated cooling signature due to heat dissipation into the blood flow (bead temperature decrease with characteristic flow-perturbation jitter in the temperature waveform). Subsequently, a withdrawal movement of the bead back toward the skin, pausing at the anterior (upper) wall, indicates an increased signal (higher temperature) associated with less efficient cooling due to the flow boundary layer at the vessel wall. In turn, as the probe is further withdrawn and the bead is returned to a position just in the track (2 mm out of the lumen), the characteristic relatively unperturbed temperature baseline waveform is again reproduced. Accordingly, the thermistor sensor has the ability to indicate when it is, alternatively, in the track (here above the vessel), in the lumen of the vessel, or at the wall of the vessel.

Figure 41:
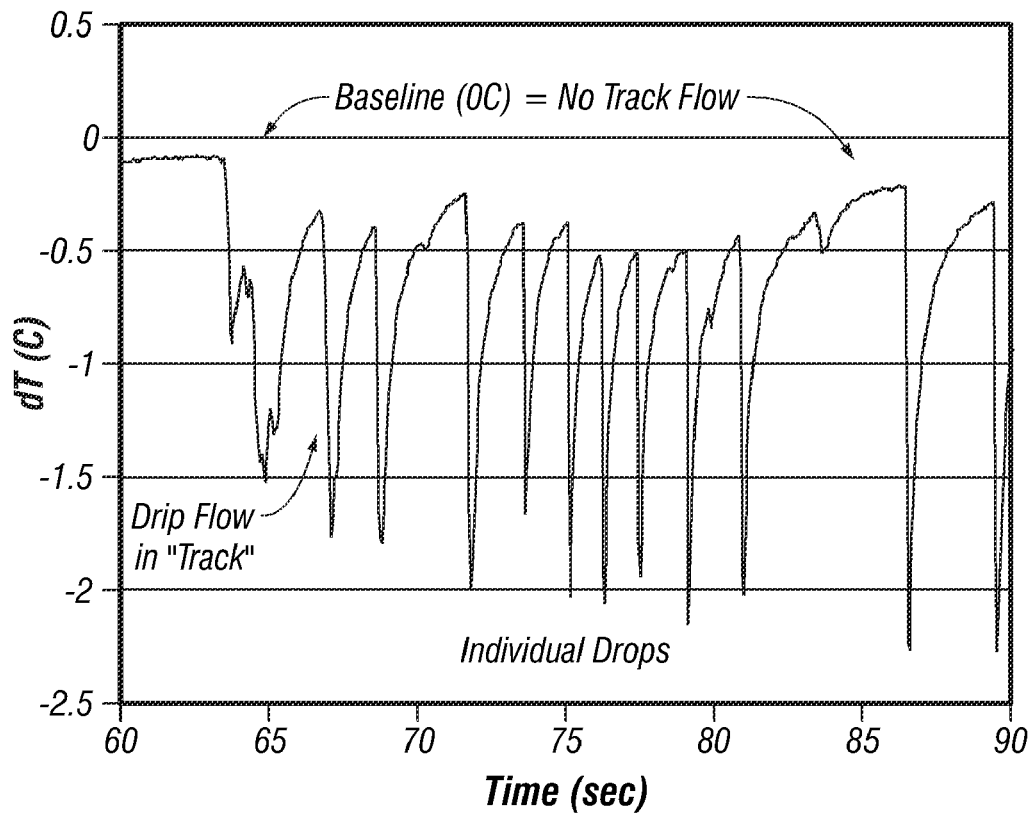
FIG. 41 is a graph of temperature signals from a thermistor bead on a TDTM probe while bleeding is simulated using dropwise flow pulses.

The thermistor also has the ability to indicate when bleeding in the track occurs. FIG. 41 depicts a graph where blood mimicking flow (using water) is produced over the thermistor one drop at a time while the bead is in a track (small duct in thermal equilibrium with the agar and the fluid). As can be seen, the thermistor signal is extremely sensitive to detecting even discrete drops flowing over it. Thus, in principle, a TDTM probe having a thermistor bead in its shaft in the puncture track should be sensitive enough to detect any thermally significant track bleeding, or bodily fluid leakage, from the puncture site.

Figure 42:
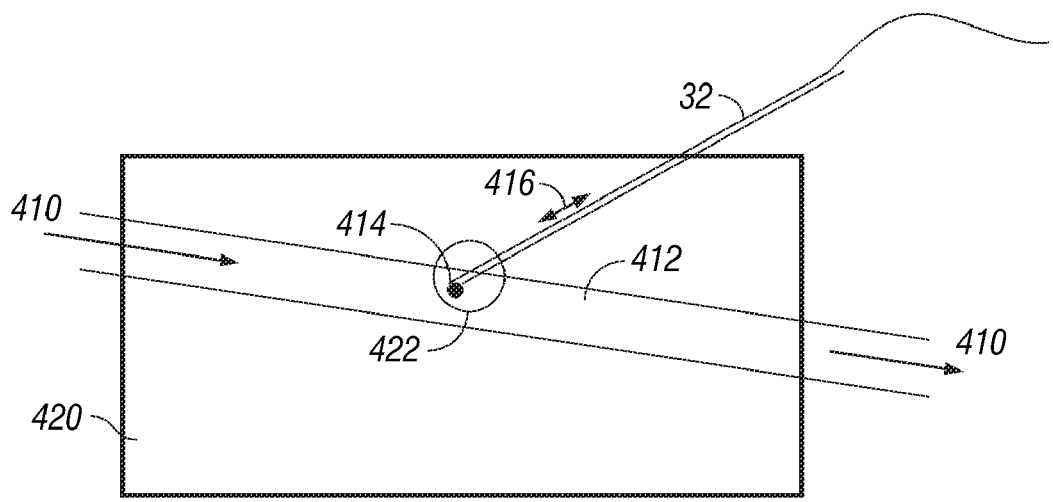
FIG. 42 is a schematic of a TDTM probe having a single thermistor at its tip under pulsatile flood flow.

When used in patients, the nature of the thermistor temperature signals will change relative to the above results in phantoms, in large part due to the pulsatile nature of blood flow in arteries and veins. To characterize TDTM probe behavior under such conditions, arterial catheterization wounds in pigs were studied. FIG. 42 shows the experimental setup with the artery 412 located in the pig tissue 420 and the vessel puncture site situated at 414, again using the single bead TDTM probe of FIGS. 39 through 41.

Figure 43A:
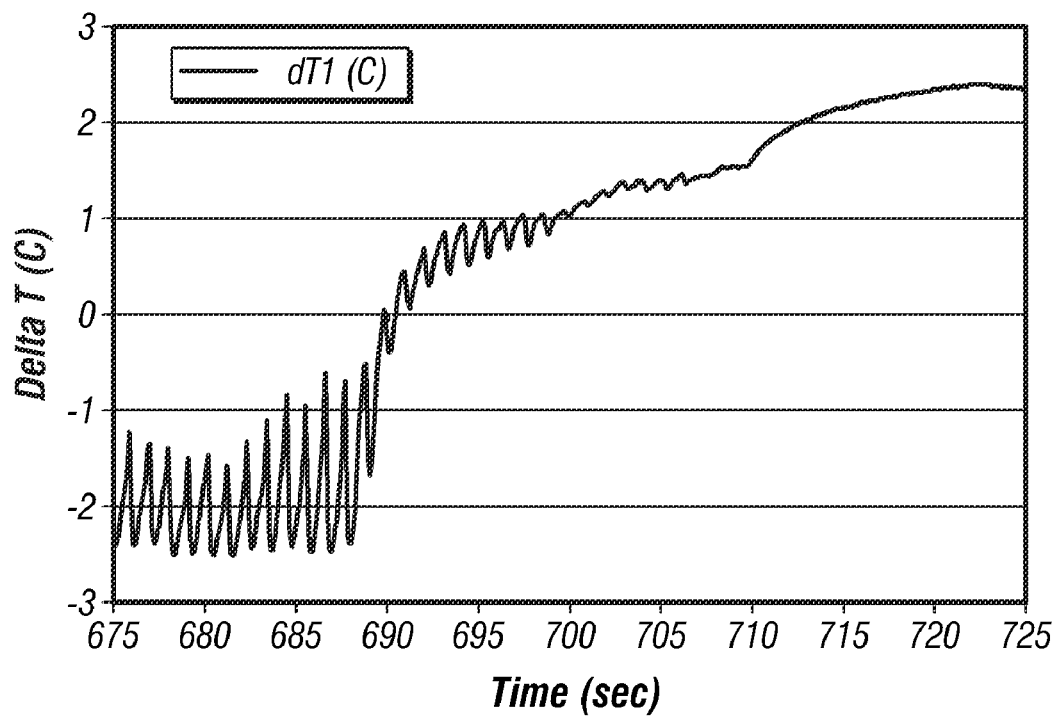
FIG. 43A is a graph of temperature differential measured from experimental setup of FIG. 42 while the TDTM probe bead is moved from the lumen of the femoral artery into the puncture track.
Figure 43B:
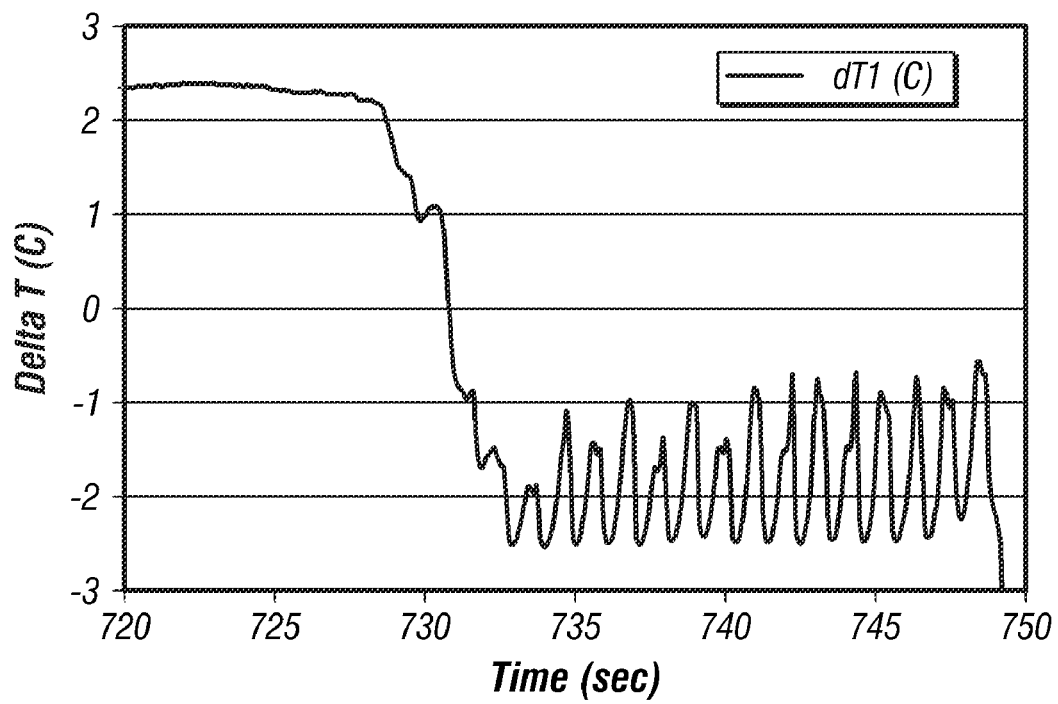
FIG. 43B is a graph of temperature differential measured from experimental setup of FIG. 42 while the TDTM probe bead is moved from the puncture track under maximal compression (no track bleeding) conditions directly to the lumen of the femoral artery.

As shown in the graphs depicted in FIGS. 43A and 43B, when a thermistor bead is fully in the artery luminal blood flow, an oscillatory thermal signal is produced of significant amplitude, indicative of the pulsatile change in convective cooling surrounding the bead, i.e., the stop-start nature of the vessel blood flow accompanying the heart cycle (systole to diastole) of the animal. As the tip of the probe is drawn up to the anterior (upper) vessel wall and into the puncture wound in the vessel, the magnitude of the signal increases (more heating occurs), but the oscillation amplitude is diminished, both trends associated with decreasing flow velocity next to the artery wall (poorer cooling due to the wall boundary layer flow, exhibiting less flow fluctuation from systole to diastole) (see FIG. 43A). While translating the probe tip up into the track just above the vessel wall, some pulsatile flow cooling is still present in the experiment, here due to only minimal tissue compression being applied at this time. FIG. 43A indicates, however, that the event of compressing the tissue maximally (to the point where no bleeding occurs in the track) can be faithfully reflected in the thermistor signal, as the equilibrium temperature rises to a maximum (conduction dominated thermal equilibrium normally associated with the baseline zero temperature) and pulsatile oscillations (due to track convection) are extinguished.

Thus, TDTM probe thermistor beads can provide signal information indicating when they reside either in the lumen of the vessel, near or at the vessel wall, or in the track, with either modest or significant compression (i.e., indicating the presence or absence of track bleeding). These properties can therefore be used to both place a TDTM probe in the track such that the probe would be in a known relationship to the puncture site, and in such a way that track bleeding could be monitored, providing user feedback on level of tissue compression, with such information also being used to confirm absence of track bleeding, avoiding potentially compromising the efficacy of the cautery thermal dose via heat carried away in blood from the treatment zone.

Figure 44:
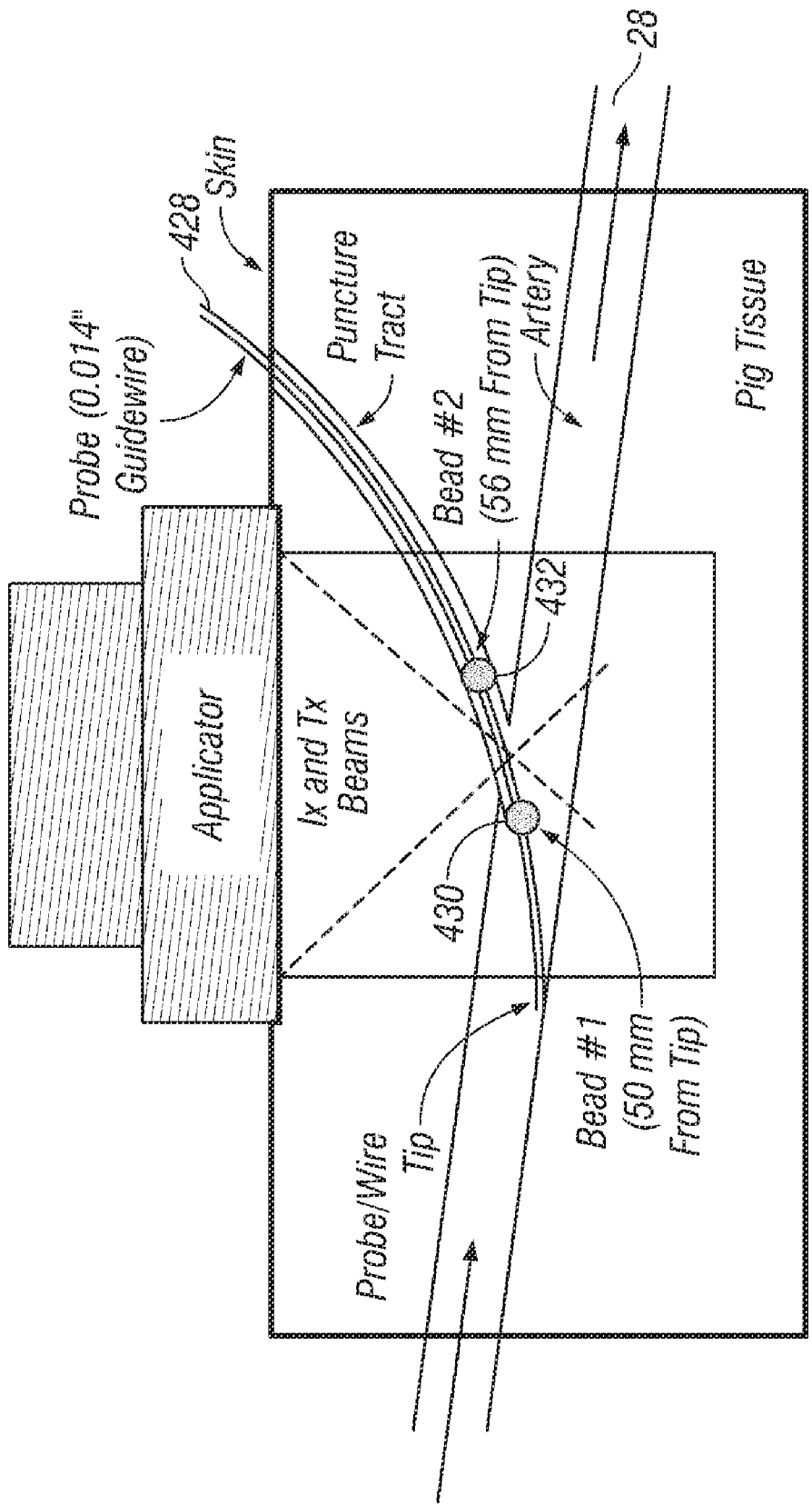
FIG. 44 is a schematic of a TDTM probe having dual thermistor beads near its tip under in vivo pulsatile blood flow conditions.

As will be described below, the ability of placing the TDTM probe 428 in fixed relationship to the puncture site can be useful in targeting the therapeutic energy from a device used for deep cautery. One method to place the probe at the puncture site is illustrated in FIG. 44 using a TDTM probe with two thermistor beads 430 and 432. Here the probe 428 is placed such that its distal end beads 430 and 432 (separated by a small distance optimized for the application) straddle the puncture hole. In this case, the distal sensor 430 resides in the lumen of the artery 28, whereas the proximal bead 432 is in the track just above the puncture. The signals from the thermistors can be such that they can guide the clinician in positioning the probe 428 in this arrangement at the puncture. The guidance in such positioning could be derived from either direct operator observation and interpretation of the waveforms, or through a more automated, yet simple, user interface (e.g., one employing an algorithm that translates the waveform information into automatically interpreted symbolic information providing positioning cues).

Figure 45:
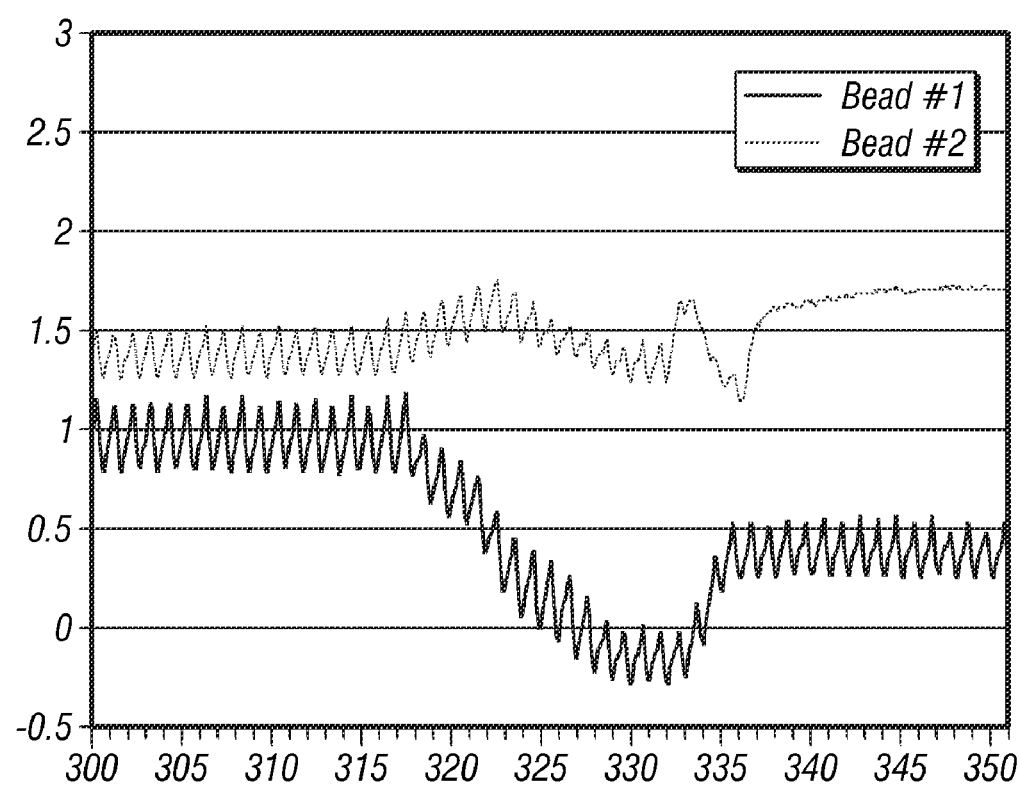
FIG. 45 is a graph of temperature signals from the TDTM probe of FIG. 44. The TDTM probe is moved from the positions of both beads located in the lumen to both beads in the puncture track.

FIG. 45 is a graph depicting sample temperature traces from an in vivo pig experiment in which successful placement of the thermistor bead portion of the probe was placed in the artery in the arrangement represented in FIG. 44, i.e., dual beads were positioned to straddle the femoral artery puncture.

Figure 46:
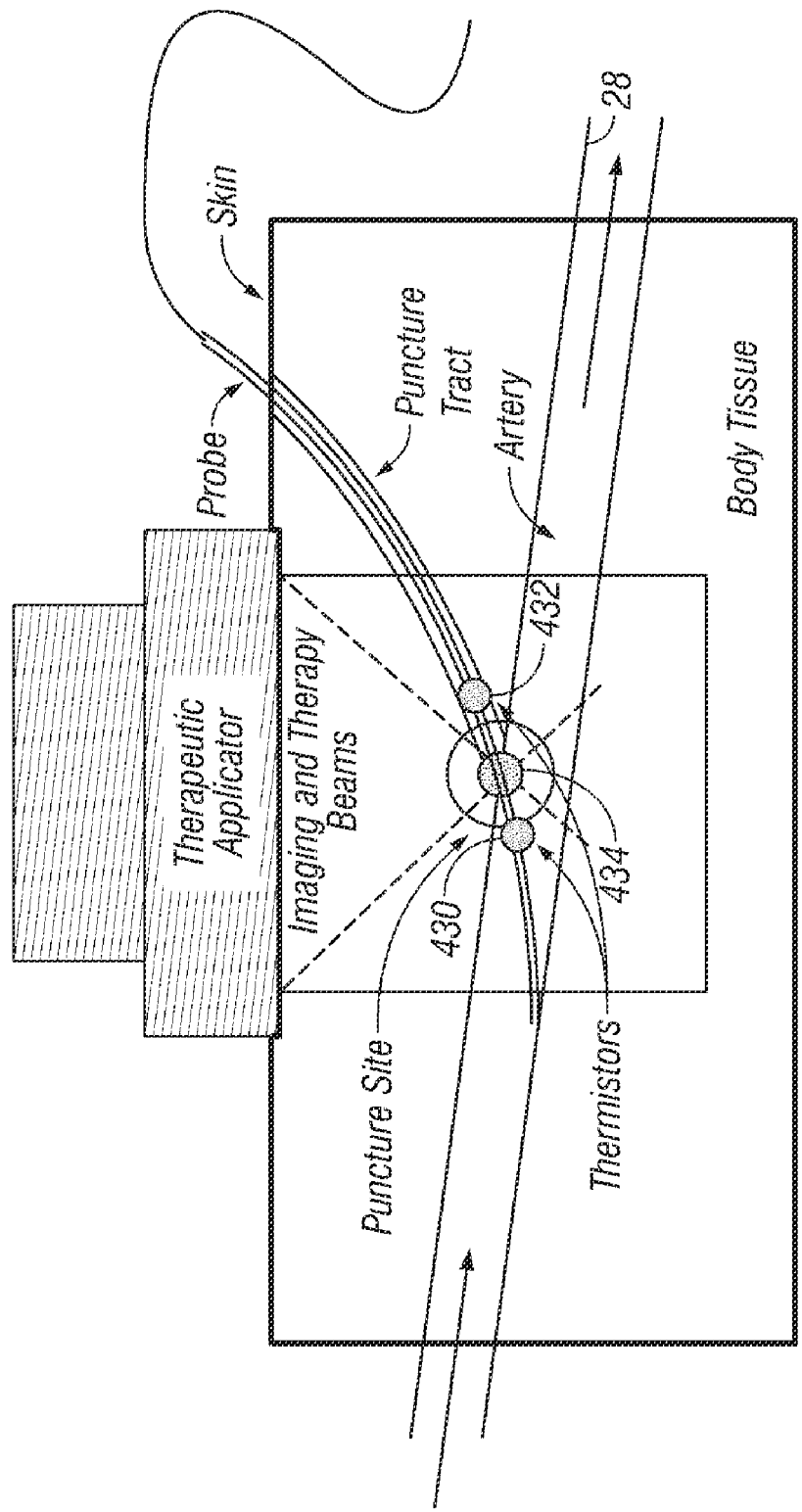
FIG. 46 is a schematic of a TDTM probe having three thermistor beads near its tip.

Another embodiment includes a triple bead TDTM probe, as shown in FIG. 46. In this embodiment, similar to FIG. 44, the distal bead 430 (nearest the tip) would be placed in the lumen of the punctured vessel 28, while the proximal bead 432 is placed in the puncture track, thus bracketing the puncture site. In this case, assuming bead separation distances optimized to the application, the third (center) bead 434 may be located approximately at the puncture site. Deployed in this fashion, the thermistor beads could be used for guiding and confirming the placement of the therapeutic energy dose, for example, by simply delivering test exposures (shots) of therapeutic energy at the appropriate depth and positioning the therapeutic beam using the feedback of the thermistor heating responses to maximize the heating response on the center bead. Those of skill in the art will appreciate that any number of thermistors may be employed to provide further precision in locating an arteriotomy.

Figure 47:
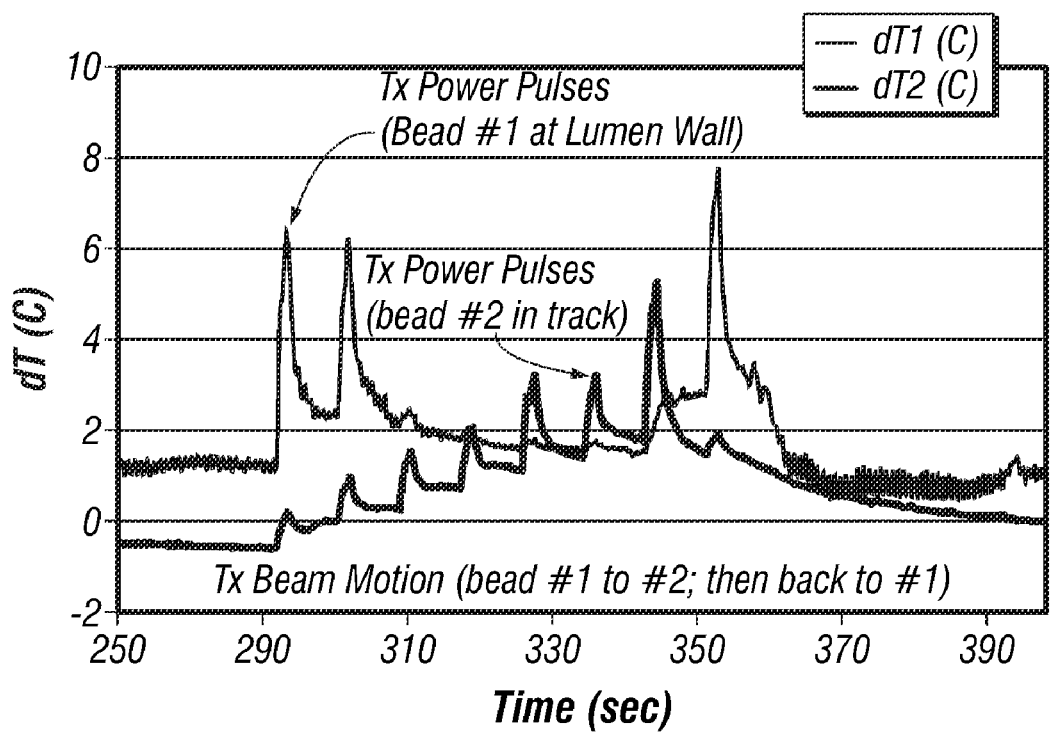
FIG. 47 is a graph of temperature differentials measured from a TDTM probe with dual beads in response to therapeutic energy test power pulses delivered from a focused ultrasound applicator.

To illustrate one method for guiding a therapeutic beam for targeting, FIG. 47 is graph showing the thermal responses from a dual bead TDTM probe placed at the puncture site as in the case shown in FIG. 44, here in a pig femoral artery subjected to pulsed test shots of therapeutic energy. The position of the beam focus and the probe thermistor beads are simultaneously monitored using gray scale B-mode (2D) ultrasound imaging. As shown, while using controlled movement of the hand-held therapeutic applicator, the position of the focus of the therapeutic beam passes (in the plane of the 2D image) from bead #1 to bead #2. The path of the therapeutic beam focus is reflected in changes in amplitude of the temperature spikes produced by the pulsed delivery of power as the applicator targeting orientation and position is moved. By maximizing the temperature spike at the bead designated as the target sensor, the energy can be appropriately targeted (while the TDTM probe is in place in the tissue puncture region).

In some embodiments, attempts to seal the puncture with the TDTM probe in place (i.e., deployed through the puncture) is contraindicated due to the tendency of the probe to either a) interfere with the sealing process during dosing, or b) disrupt a successful seal upon removal of the probe. Accordingly, in some embodiments, the probe is at least partially withdrawn until it is clear of the puncture prior to the delivery of the dose. This maneuver will not eliminate the advantages of the probe. While in situ (at the puncture), the TDTM probe can be used to position the therapeutic beam at the puncture, as described above. Further, the adequacy and level of the therapeutic dosing power can be assessed through the thermistor thermal signals in response to test power pulses (as illustrated in FIG. 47) while the probe is in place prior to dosing. Additionally, by withdrawing the TDTM probe just prior to dosing sufficiently to clear it from the puncture site, but with at least one thermistor remaining in the puncture track, the probe can be used to monitor and guide compression and confirm the absence of track bleeding.

Figure 48:
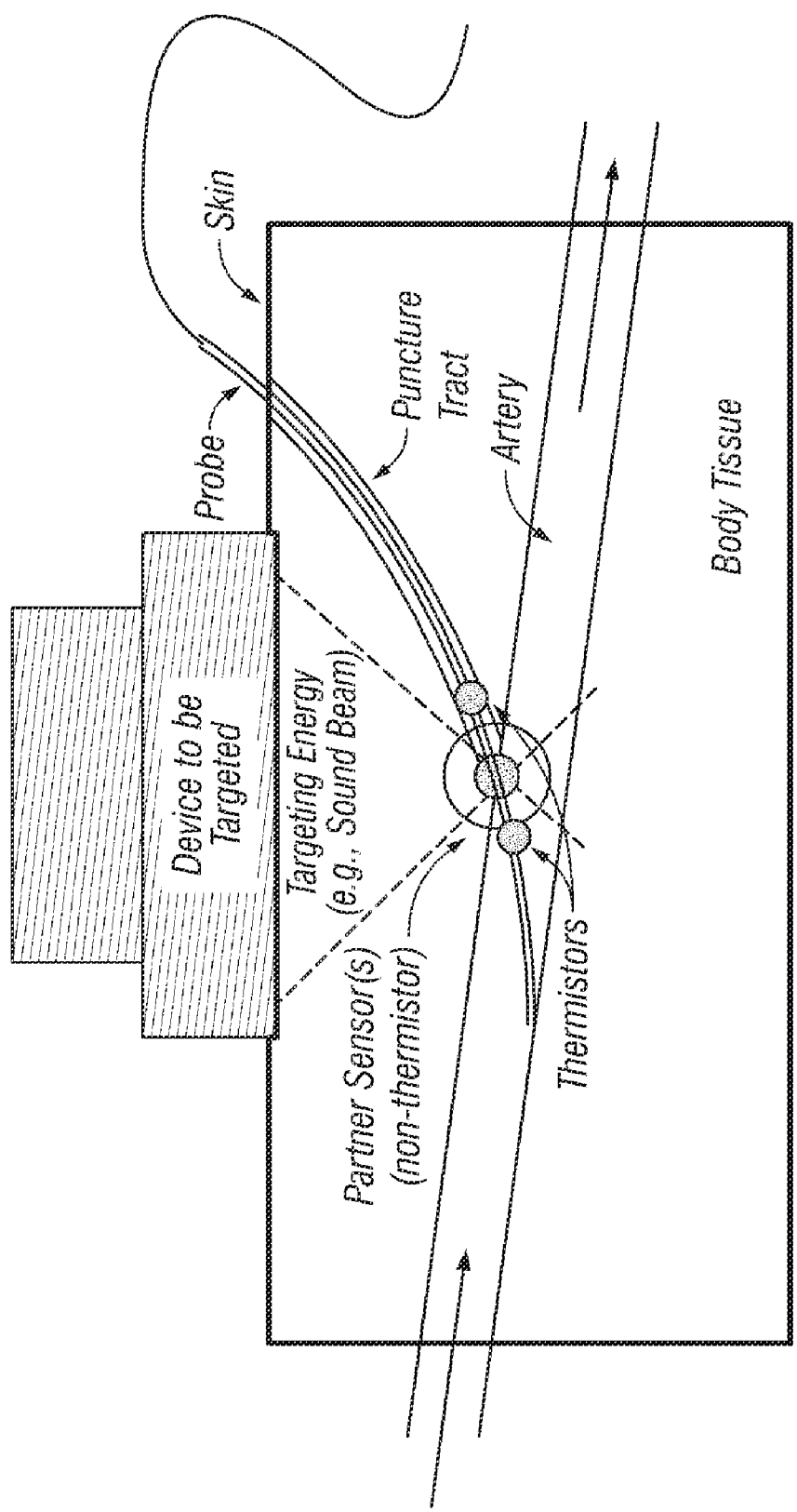
FIG. 48 is a schematic of a TDTM probe having two thermistors in conjunction with a non-thermistor partner sensor.

It is also possible to use TDTM probe thermistors in conjunction with other sensors (non-thermistor) for targeting and monitoring the puncture site. These "partner" sensors could be deployed on the shaft of the probe used in the puncture track, and could provide complementary, redundant or unique information for orienting and guiding a medical device of interest (e.g., a therapeutic device such as an ultrasound applicator used for sealing puncture wounds). FIG. 48 illustrates a system where the probe contains two thermisters and one non-thermister partner sensor positioned in between. An example of complementary information from the thermistor could include monitoring the state of bleeding of the puncture track, while the partner sensor broadcasts its location for 3D positioning (e.g., by a distance measurement-based or time-of-flight based triangulation method with appropriate receiver-transmitter pairs, such as the ATOF technique described in above). Such partner sensors could be based on a variety of energy forms, such as electrical, electromagnetic, magnetic, and acoustic energy, using appropriate transmission and receiver modules in the sensor and on the medical device being guided.

Figure 49:
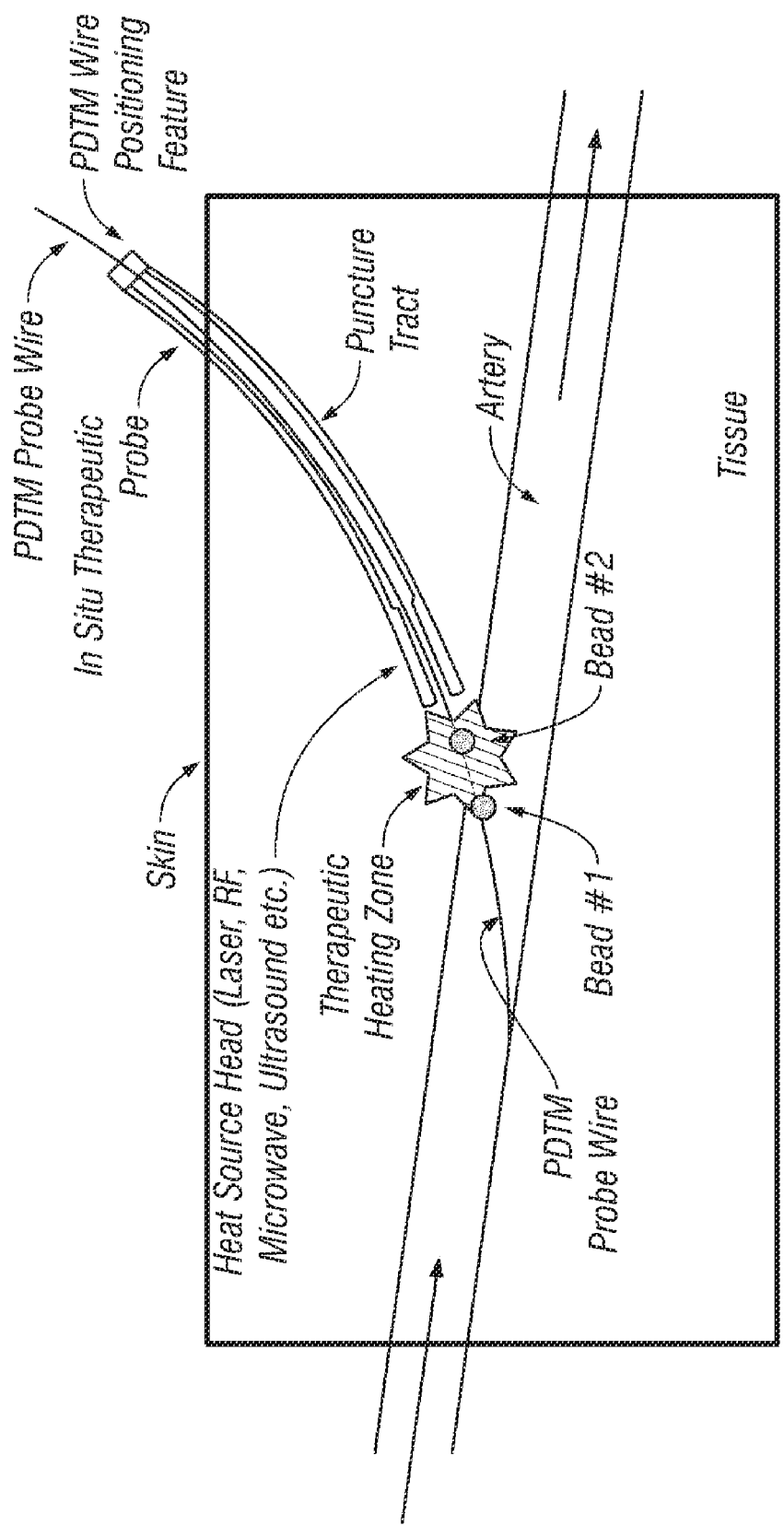
FIG. 49 is a schematic of a TDTM probe used in conjunction with an invasive cautery or puncture sealing device.

In some embodiments, a TDTM probe is used in conjunction with invasive therapeutic devices used for sealing puncture wounds. FIG. 49 illustrates a system where both thermister beads and a therapeutic heat source are introduced to the puncture site. Such therapeutic heating devices could be placed down the puncture track, deployed as catheter-like minimally invasive surgical (MIS) tools, and could have their sources of thermal energy delivery (therapeutic head) located at their distal tip. A variety of energy sources could be possible with such MIS tools (e.g., RF electrical heating devices, therapeutic laser energy delivered via fiber-optics or light wave-guides, microwave antennae, ultrasound transducers, and the like). As for non-invasive hemostasis applicators, the invasive therapeutic devices can be positioned in appropriate relation to the puncture site to effectively target and seal the wound. The TDTM probe could be used to locate the therapeutic head of the invasive sealing device at the puncture site by using the TDTM probe as a guide-wire structure. In this configuration, the thermistor beads of the TDTM probe would be placed at the puncture site, with the cautery device deployed over the TDTM probe and advanced toward the puncture site until it reached a position that corresponded to an appropriate separation distance between the therapeutic head and the puncture site. Prior to delivering the thermal dose, the TDTM probe could be withdrawn like a guidewire up into the inner channel of the cautery probe to remove the thermistor beads from the heated treatment zone before the thermal dose is delivered to the puncture site. As for the previously described TDTM probe concepts, the thermistor beads could also be used to confirm adequate compression at the treated site by monitoring bleeding up the track of the MIS cautery device. In addition, the thermistor beads could be used to monitor the level of the delivered dose through the thermal response of the thermistor to therapeutic test doses, as describe above.

In summary, the TDTM probe can be used in conjunction with both non-invasive and invasive thermal sealing or cautery therapeutic devices in halting bleeding or bodily fluid leakage at depth from penetration wounds associated with medical procedures. The TDTM probe can assist in: a) locating the puncture site (e.g., arteriotomy), and can be positioned in relationship to this site; b) confirming/guiding tissue compression levels adequate to eliminate track bleeding during application of the thermal dose; and c) targeting the therapeutic energy; d) assessing in situ the propriety of the therapeutic power In addition, the thermistor sensors can be used in combination and coordination with other types of sensors, and in different configurations and spatial arrangements. Further more, the thermistor sensors can also be used to guide invasive therapeutic devices (e.g., minimally invasive surgical type tools). Finally, TDTM probes with one, two, three or more sensors can be used, depending on the application and the procedural approach desired.

Although the invention has been described with reference to embodiments and examples, it should be understood that numerous and various modifications can be made without departing from the spirit of the invention. Accordingly, the invention is limited only by the following claims.

What is claimed is:

1. A method of treating an adventitia of a blood vessel within a patient, comprising:
   inserting a targeting catheter into a patient;
   positioning the targeting catheter proximate to the adventitia of the blood vessel;
   emitting at least one signal from the targeting catheter from within the patient;
   receiving the at least one signal with a plurality of receivers on a therapeutic applicator, wherein the plurality of receivers are spaced apart around an outer perimeter of one or more therapeutic ultrasound transducers on the therapeutic applicator;
   determining an acoustic time-of-flight from the targeting catheter to the therapeutic applicator based at least in part on the at least one signal;
   determining a location of a portion of the targeting catheter relative to the therapeutic ultrasound applicator based at least in part on the acoustic time-of-flight determination;
   adjusting a focus of the one or more therapeutic ultrasound transducers of the therapeutic ultrasound applicator based on the determined location of the portion of the targeting catheter, wherein the focus is adjusted to target the adventitia of the blood vessel; and
   emitting a dose of focused ultrasound from the therapeutic applicator to the adventitia of the blood vessel.

2. The method of claim 1, wherein determining the location of the portion of the targeting catheter relative to the therapeutic applicator comprises using triangulation of the at least one signal emitted from the targeting catheter.

3. The method of claim 1, wherein the at least one signal is emitted from a beacon disposed on the targeting catheter.

4. The method of claim 3, wherein the at least one signal comprises a tone burst of sound.

5. The method of claim 1, wherein the at least one signal is an ultrasound signal.

6. The method of claim 1, further comprising providing a user interface to assist a user in adjusting the focus of the therapeutic applicator.

7. The method of claim 6, further comprising displaying graphical elements on the user interface.

8. A method of treating an adventitia of a blood vessel within a patient, comprising:
   inserting a targeting catheter into a patient, the targeting catheter comprising a receiver;
   positioning the targeting catheter proximate to the adventitia of the blood vessel;
   emitting at least one signal from a therapeutic ultrasound applicator that is disposed external to the patient, the at least one signal being emitted from a plurality of transmitters spaced apart around an outer perimeter of one or more therapeutic ultrasound transducers;
   receiving the at least one signal with the receiver;
   determining an acoustic time-of-flight from the plurality of transmitters to the receiver based at least in part on the at least one signal;
   determining a location of a portion of the targeting catheter relative to the therapeutic applicator based at least in part on the acoustic time-of-flight determination;
   adjusting a focus of the one or more therapeutic ultrasound transducers of the therapeutic ultrasound applicator based on the determined location of the portion of the targeting catheter, wherein the focus is adjusted to target the adventitia of the blood vessel; and
   emitting a dose of focused ultrasound from the therapeutic applicator to the adventitia of the blood vessel.

9. The method of claim 8, wherein determining the location of the portion of the targeting catheter relative to the therapeutic applicator comprises using triangulation.

10. The method of claim 8, wherein the at least one signal comprises a tone burst of sound.

11. The method of claim 8, wherein the at least one signal is an ultrasound signal.

12. The method of claim 8, further comprising providing a user interface to assist a user in adjusting the focus of the therapeutic applicator.

13. The method of claim 12, further comprising displaying graphical elements on the user interface.

* * * * *